US006107104A

United States Patent [19]
Lockerbie et al.

[11] Patent Number: 6,107,104
[45] Date of Patent: Aug. 22, 2000

[54] MODULATORS OF ANCHORING PROTEIN FUNCTION

[75] Inventors: Robert Owen Lockerbie, Kirkland; Monique L. Howard, Seattle; W. Michael Gallatin, Mercer Island; Yvonne Lai, Seattle, all of Wash.

[73] Assignee: ICOS Corporation, Bothell, Wash.

[21] Appl. No.: 08/721,458

[22] Filed: Sep. 27, 1996

Related U.S. Application Data

[63] Continuation-in-part of application No. 08/503,226, Jul. 17, 1995, which is a continuation-in-part of application No. 08/404,731, Mar. 15, 1995, Pat. No. 5,744,354, which is a continuation-in-part of application No. 08/344,227, Nov. 23, 1994, Pat. No. 5,807,693.

[51] Int. Cl.⁷ .................................................. G01N 33/543
[52] U.S. Cl. .............................. 436/578; 435/4; 435/7.1; 435/7.2; 435/7.93
[58] Field of Search ................................. 435/4, 7.1, 7.2, 435/7.93; 436/501; 530/350, 780; 536/23.1, 23.5

[56] References Cited

U.S. PATENT DOCUMENTS

| | | | |
|---|---|---|---|
| 4,766,046 | 8/1988 | Abra et al. ............................... | 424/450 |
| 5,169,637 | 12/1992 | Lenk et al. ............................... | 424/450 |
| 5,180,713 | 1/1993 | Abra .......................................... | 514/31 |
| 5,185,154 | 2/1993 | Lasic et al. .............................. | 424/450 |
| 5,204,112 | 4/1993 | Hope et al. .............................. | 124/450 |
| 5,252,263 | 10/1993 | Hope et al. .............................. | 264/4.3 |

FOREIGN PATENT DOCUMENTS

WO 92/02244  2/1992  WIPO .

OTHER PUBLICATIONS

Kuno et al, "Evidence for a second isoform of the catalytic subunit of calmodulin–dependent protein phosphatase (Calcineurin A)", Biochem. Biophys. Res. Commun., vol. 165, No. 3, pp. 1352–1358, 12–29–8.

Giri et al, "Chromosomal mapping of the human genes for the calmodulin–dependent protein phosphatase (Calcineurin) catalytic subunit", Biochem. Biophys. Res. Commun., vol. 181, No. 1, pp. 252–258, 11–27–9.

Allen et al., "Cyclosporin: A Therapy for Wegner's Granulomatosis" in *ANCA—Associated Vasculitides: Immunological and Clinical Aspects*, Gross (ed.) New York: Plenum Press (1993), pp. 473–476.

Belldegrun et al., "Interferon–α Primed Tumor–Infiltrating Lymphocytes Combined with Interleukin–2 and Interferon–α as Therapy for Metastatic Renal Cell Carcinoma", *J. Urol.* 150:1384–1390 (1993).

Billingsley et al., "Identification of Calmodulin–Binding Proteins," *Meth. Enzymol.* 184:451–467 (1990).

Bougneres et al., "Limited Duration of Remission of Insulin Dependency in Children with Recent Overt Type I Diabetes Treated with Low–Dose Cyclosporin", *Diabetes* 39:1264–1272 (1990).

Bougneres et al., "Factors Associated With Early Remission Of Type I Diabetes In Children Treated With Cyclosporine", *N.Eng.J.Med.* 318:663–670 (1988).

Bruton and Koeller, "Recombinant Interleukin–2", *Pharmacotherapy* 14:635–656 (1994).

Brynskov, "Cyclosporin in Crohn's disease", *Dan.Med.Bull.* 41:332–344 (1994).

Carr et al., "Localization of the cAMP–dependent Protein Kinase to the Postsynaptic Densities of A–Kinase Anchoring Proteins", *J.Biol.Chem.* 267:16816–16823 (1992).

Carr et al., "Interaction of the Regulatory Subunit (RII) of cAMP–dependent Protein Kinase with RII–anchoring Proteins Occurs through an Amphipathic Helix Binding Motif*", *J.Biol.Chem.* 266:14188–14192 (1991).

Carr et al., "Association of the type II cAMP–dependent Protein Kinase with a Human Thyroid RII–anchoring Protein", *J.Biol.Chem.* 267:13376–13382 (1992).

Carr et al., "Follicle–stimulating Hormone Regulation of A–kinase Anchoring Proteins in Granulosa Cells*", *J.Biol.Chem.* 268:20729–20732 (1993).

Cheley et al., "Type II Regulatory Subunites of cAMP–dependent Protein Kinase and Their Binding Proteins in the Nervous System of *Aplysia californica*\*", *J.Biol.Chem.* 269:2911–2920 (1994).

Choi and Targan, "Immunomodulator Therapy in Inflammatory Bowel Disease", *Dig.Dis and Sci.* 39:1885–1892 (1994).

Clipstone and Crabtree, "Identification of calcineurin as a key signalling enzyme in T–lymphocyte activation", *Nature* 357:695–697 (1992).

Coghlan, V. et al., "Association of Protein Kinase A and Protein Phosphatase 2B with a Common Anchoring Protein", *Science* 267:108–111 (1995).

Coghlan et al., "Cloning and Characterization of AKAP 95, a Nuclear Protein That Associates with the Regulatory Subunit of Type II cAMP–dependent Protein Kinase*", *J.Biol.Chem.* 269:7658–7665 (1994).

Cooper et al., "Atopic Dermatitis: Recent Trends in Pathogenesis and Therapy", *J.Invest.Derm* 102:128–137 (1994).

(List continued on next page.)

*Primary Examiner*—James C. Housel
*Assistant Examiner*—Rodney P. Swartz
*Attorney, Agent, or Firm*—Marshall, O'Toole, Gerstein, Murray & Borun

[57] ABSTRACT

The present invention provides compositions and methods useful for isolating calcineurin as well as inhibiting calcineurin activity. The compositions are peptides that contain regions that are homologous to calcineurin-binding regions of AKAP 79. Also provided are methods for determining if a cell contains a calcineurin-binding and PKA-binding anchoring protein that are useful for identifying additional proteins that bind both calcineurin and PKA. Another aspect of the present invention is methods for enhancing expression of interleukin 2 by T cells. Further provided are methods to identify proteins which interact with AKAP 79, and methods to identify inhibitors of AKAP 79 interaction with other proteins.

1 Claim, 7 Drawing Sheets

OTHER PUBLICATIONS

Cuéllar et al., "Treatment of psoriatic arthritis", *Ballier's Clin.Rheum.* 8:483–498 (1994).

Cyert and Thorner, "Calcineurin–like Activity in Saccharomyces cerevisiae", *J.Cell.Biol.* 107:841a (1989).

de Groen et al., "Central Nervous System Toxicity After Liver Transplantation", *N.Eng.J.Med.* 317:861–866 (1987) [Page numbers cited as "861–566" on p. 72].

DeCamilli et al., "Heterogeneous Distribution of the cAMP Receptor Protein RII in the Nervous System: Evidence for Its Intracellular Accumulation of Microtubules, Microtubule–organizing Centers, and in the Area of the Golgi Complex", *J.Cell.Biol.* 103:189–203 (1986).

Deeg et al., "Cyclosporine as Prophylaxis for Graft–Versus–Host Disease: A Randomized Study in Patients Undergoing Marrow Transplantation for Acute Nonlymphoblastic Leukemia", *Blood* 65:1325–1334 (1985).

Dillman, "The Clinical Experience with Interleukin–2 in Cancer Therapy", *Cancer Biotherapy* 9:183–209 (1994).

Dougados and Torley, "Efficacy of Cyclosporin A in Rheumatoid Arthritis: Worldwide Experience", *Br.J.Rheum* 32(suppl 1):57–59 (1993).

Durfee et al., "The retinoblastoma protein associates with the protein phosphatase type 1 catalytic subunit", *Genes and Development* 7:555–567 (1993).

Eichholtz et al., "A Myristoylated Pseudosubstrate Peptide, a Novel Protein Kinase C Inhibitor*", *J.Biol.Chem* 268:1982–1986 (1993).

Eidelman et al., "Neurologic Complications of FK 506", *Transplant.Proc.* 23:3175–3178 (1991).

Elliot and Chase, "Prevention or delay of Type 1 (insulin–dependent) diabetes mellitus in children using nicotinamide", *Diabetologia* 34:362–365 (1991).

Ellis et al., "Cyclosporine Improves Psoriasis in a Double–blind Study", *JAMA* 256:3110–3116 (1986).

Feldt–Rasmussen et al., "Oral cyclosporine for severe chronic idiopathic urticaria and angioedema", *Diabetes Medicine* 7:429–433 (1990).

Feutren et al., "Cyclosporin Increases The Rate And Length Of Remissions In Insulin–Dependent Diabetes Of Recent Onset", *Lancet* 2:119–124 (1986).

Feutren, "Renal Morphology After Cyclosporin A Therapy In Rheumatoid Arthritis Patients," *Br.J.Rheum.* 32(suppl 1):65–71 (1993).

Førre et al., "An Open, Controlled, Randomized Comparison Of Cyclosporine And Azathioprine In The Treatment Of Rheumatoid Arthritis: A Preliminary Report", *Arthritis Reheum.* 30:88–92 (1987).

Fradin et al., "Oral cyclosporine for severe chronic idiopathic urticaria and angioedema", *J.Am.Acad.Derm.* 25:1065–1067 (1991).

Fung et al., "Adverse Effects Associated With the Use of FK 506", *Transplant.Proc.* 23:3105–3108 (1991).

Glantz et al., "Characterization of Distinct Tethering and Intracellular Targeting Domains in AKAP75 a Protein That Links cAMP–dependent Protein Kinase IIβ to the Cytoskeleton*", *J.Biol.Chem.* 268:12796–12804 (1993).

Glantz et al., "cAMP Signaling in Neurons: Patterns of Neuronal Expression and Intracellular Localization for a Novel Protein, AKAP 150, that Anchors the Regulatory Subunit of cAMP–Dependent Protein Kinase IIβ", *Mol. Cell.Biol.* 3:1215–1228 (1992).

Griffith et al., "X–Ray Structure of Calcineurin Inhibited by the Immunophilin–Immunosuppressant FKBP12–FK506 Complex," *Cell* 82:507–522 (1995).

Guerini and Klee, "Cloning of human calcineurin A: Evidence for two isozymes and identification of a polyproline structural domain", *Proc.Natl.Acad.Sci.* (*USA*) 86:9183–9187 (1989).

Haddy et al., "Inhibition of calcineurin by cyclosporin A–cyclophilin requires calcineurin B," *FEBS* 314:37–40 (1992).

Hafner et al., "Mechanism of Inhibition of Raf–1 by Protein Kinase A," *Mol. Cell Biol.* 14:6696–6703 (1994).

Harlow and Lane, "Immunoaffinity Purification of Antibodies on an Antigen Column", in *Antibodies: A Laboratory Manual*, Harlow and Lane (eds.) Cold Spring Harbor Laboratory:Cold Spring Harbor, NY (1988), pp. 313–318.

Hausken et al., "Type II Regulatory Subunit (RII) of the cAMP–dependent Protein Kinase Interaction with A–kinase Anchor Proteins Requires Isoleucines 3 and 5*", *J.Biol.Chem.* 269:24245–24251 (1994).

Haydon and Haynes, "New immunosuppressive treatment in transplantation medicine," *Ballier's Clin. Gastroentero.* 8:455–464 (1994).

Hirsch et al., "Cloning and Expression of an Intron–less Gene for AKAP 75, an Anchor Protein for the Regulatory Subunit of cAMP–dependent Protein Kinase IIβ*", *J.Biol.Chem.* 267:2131–2134 (1992).

Hollon and Yoshimura, "Variation in Enzymatic Transient Gene Expression Assays," *Anal. Biochem.* 182:411–418 (1989).

Ho et al., "Site–directed mutagenesis by overlap extension using the polymerase chain reaction," *Gene* 77:51–59 (1989).

Hulton et al., "Long–term cyclosporin A treatment of minimal–change nephrotic syndrome of childhood", *Pediatr.Nephrol.* 8:401–403 (1994).

Husi et al., "Mapping of the Immunophilin–Immunosuppressant Site of Interaction on Calcineurin," *J. Biol Chem.* 269:14199–14204 (1994).

International Kidney Biopsy Registry of Cyclosporin in Autoimmune Diseases, "Renal Morphology After Cyclosporin A Therapy In Rheumatoid Arthritis Patients," *Br. J. Rheum.* 32(suppl 1):65–71 (1993).

Jain et al., "The T–cell transcription factor $NFAT_p$ is a substrate for calcineurin and interacts with Fos and Jun", *Nature* 365:352–355 (1993).

Jenner et al., "Cyclosporin A treatment of young children with newly–diagnosed Type 1 (insulin–dependent) diabetic mellitus", *Diabetiologia* 35:884–888 (1992).

Kahan, "Cyclosporine", *N.Eng.J.Med.* 321:1725–1738 (1989).

Kahan et al., "Complications of Cyclosporine–Prednisone Immunosuppression in 402 Renal Allograft Recipients Exclusively Followed At A Single Center For From One To Five Years", *Transplantation* 43:197–204 (1987).

Kaplan, "Recent Advances in Cytokine Therapy in Leprosy", *J.Infect.Dis.* 167(suppl 1):S18–22 (1993).

Kawamura and Su, "Interaction of FKBP12–FK506 with Calcineurin A at the B Subunit–binding Domain," *J. Biol. Chem.* 270:15463–15466 (1995).

Keegan et al., "Separation of DNA Binding from the Transcription–Activating Function of a Eukaryotic Regulatory Protien", *Science* 231:699–704 (1986).

Keryer et al., "A High–Affinity Binding Protein for the Regulatory Subunit of cAMP–Dependent Protein Kinase II in the Centrosome of Human Cells", *Exp.Cell Res.* 204:230–240 (1993).

Klauck et al., "Coordination of Three Signaling Enzymes by AKAP79, a Mammalian Scaffold Protein," *Science* 271:1589–1592 (1996).

Klee et al., "Calcineurin", *Adv.Enzymol.* 61:149–200 (1984).

Kunkel et al., "Rapid and Efficient Site–Specific Mutagenesis without Phenotypic Selection," *Methods in Enzymology* 54:367 (1987).

Kunkel, "Rapid and efficient site–specific mutagenesis without phenotypic selection," *Proc. Natl. Acad. Sci. (USA)* 82:488 (1985).

Lange and Reiderer, "Glutamatergic Drugs in Parkinson's Disease", *Life Sciences* 55:2067–2075 (1994).

LaVallie et al., "A Thioredoxin Gene Fusion Expression System That Circumvents Inclusion Body Formation in the *E.coli* Cytoplasm," *Bio/Technology* 11:187–193 (1993).

Leaker and Cairns, "Clinical aspects of cyclosporin nephrotoxicity", *Br.J.Hosp.Med.* 52:520–534 (1994).

Lester et al., "Cloning and Characterization of a Novel A–kinase Anchoring Protein," *J. Biol. Chem.* 271:9460–9465 (1996).

Ludwin and Alexopolulou, "Cyclosporin A Nephropathy in Patients with Rheumatoid Arthritis", *Br. J.Rheum.* 32(suppl 1):60–64 (1993).

Ma and Ptashne, "Deletion Analysis of GAL4 Defines Two Transcriptional Activating Segments", *Cell* 48:847–853 (1987).

MacFarlane et al., "The Hematologic Toxicity of Interleukin–2 in Patients with Metastatic Melanoma and Renal Cell Carcinoma", *Cancer* 75:1030–1037 (1995).

Manev et al., "Macrolide antibiotics protect neurons in culture against the N–methyl–D–aspartate (NMDA) receptor–mediated toxicity of glutamate", *Brain Res.* 624:331–335 (1993).

Martin et al., "Follow–up of cyclosporin A treatment in Type 1 (insulin–dependent) diabetes mellitus: lack of long–term effects", *Dibetologia* 34:429–434 (1991).

Mason, "Pharmacology of Cyclosporine (Sandimmune) VII. Pathophysiology and Toxicology of Cyclosporine in Humans and Animals", *Pharmacol.Rev.* 42:423–434 (1989).

McCartney et al., "Cloning and Characterization of A–kinase Anchor Protein 100 (AKAP100)", *J.Biol. Chem.* 270:9327–9333 (1995).

McCauley et al., "The nephrotoxicity of FK506 as compared with cyclosporine", *Curr.Opin.Nephrol.Hyperten.* 2:662–669 (1993).

Meldrum, "The role of glutamate in epilepsy and other CNS disorders", *Neurology* 44(suppl 8):S14–S23 (1994).

Merchant et al., "Immunotherapy for malignant glioma using human recombinant Interleukin–2 and activated autologous lymphocytes", *J.Neuro.* 8:173–188 (1990).

Meyrier, "Treatment of nephrotic syndrome with cyclosporin A. What remains in 1994?", *Nephrol.Dial. Transplant* 9:596–598 (1994).

Morris, "New Small Molecule Immunosuppressants for Transplantation: Review of Essential Concepts", *J.Heart and Lung Transplant.* (Nov./Dec.) pp. S275–S285 (1993).

Nairn et al., "Phosphorylation of Phosphatase Inhibitor–1 by ATPγ and Dephosphorylation of Thiophosphorylated Inhibitor–1 by Protein Phosphatases," *Neuroprotocols* 6:108–111 (1995).

Najarian et al., "A Single Institution, Randomized, Prospective Trial of Cyclosporine Versus Azathioprine–Antilymphocyte Globulin for Immunosuppression in Renal Allograft Recipients", *Ann.Surg.* 201:142–157 (1985).

Nussenblatt et al., Cyclosporin A Therapy in the Treatment of Intraocular Inflammatory Disease Resistant to Systemic Corticosteroids and Cytotoxic Agents, *Am.J.Ophthalmol.* 96:275–282 (1983).

O'Keefe et al., "FK–506– and CsA–sensitive activation of the interleukin–2 promoter by calcineurin", *Nature* 357:692–694 (1992).

Obar et al., "The RII Subunit of cAMP–Dependent Protein Kinase Binds to a Common Animo–Terminal Domain in Microtuble–Associated Proteins 2A, 2B, and 2C", *Neuron*, 3:639–645 (1989).

Olney, "Excitatory Transmitter Neurotoxicity", *Neurobiology of Aging* 15:259–260 (1994).

Owaki et al., "Raf–1 is required for T cell IL2 production," *EMBO J.* 12:4367–4373 (1993).

Oyer et al., "Cyclosporine in Cardiac Transplantation: A 2½ Year Follow–Up", *Transplant Proc.* 15:Supp 1:2546–2552 (1983).

Pacor et al., "Cyclosporin in Behcet's Disease: Results in 16 Patients after 24 Months of Therapy", *Clin Rheum.* 13:224–227 (1994).

Perrino et al., "Characterization of the Phosphatase Activity of a Baculovirus–expressed Calcineurin A Isoform*", *J.Biol.Chem.* 267:15965–15969 (1992).

Perrino et al., "Calcium Regulation of Calcineurin Phosphatase Activity by Its B Subunit and Calmodulin," *J. Biol. Chem.* in press.

Peters et al., "Tacrolimus A Review of its Pharmacology, and Therapeutic Potential in Hepatic and Renal Transplantation", *Drugs* 4:746–794 (1993).

Pierce et al., "Cellular Therapy: Scientific Rationale and Clinical Results in the Treatment of Metastatic Renal–Cell Carcinoma", *Sem. Oncol.* 22:74–80 (1995).

Platz et al., "Nephrotoxicity Following Orthotopic Liver Transplantation", *Transplantation* 58:170–178 (1994).

Reece et al., "Neurologic complications in allogeneic bone marrow transplant patients receiving cyclosporin", *Bone Marrow Transplant.* 8:393–401 (1991).

Reitamo and Granlund, "Cyclosporin A in the treatment of chronic dermatitis of the hands", *Br.J.Derm.* 130:75–78 (1994).

Rios et al., "Identification of a high affinity binding protein for the regulatory subunit RIIβ of cAMP–dependent protein kinase in Golgi enriched membranes of human lymphoblasts", *EMBO J.* 11:1723–1731 (1992).

Rosenmund et al., "Anchoring of protein kinase A is required for modulation of AMPA/kainate receptors on hippocampal neurons", *Nature* 368:853–856 (1994).

Rubino et al., "Localization and Characterization of the Binding Site for the Regulation Subunit of Type II cAMP–Dependent Protein Kinase on MAP2", *Neuron* 3:631–638 (1989).

Salek et al., "Cyclosporin greatly improves the quality of life of adults with severe atopic dermatitis. A randomized, double–blind, placebo–controlled trial", *Br.J.Derm.* 129:422–430 (1993).

Sánchez et al., "Immune Responsiveness and Lymphokine Production in Patients with Tuberculosis and Healthy Controls", *Inf.Immunol.* 62:5673–5678 (1994).

Schreiber and Crabtree, "The mechanism of action of cyclosporin A and FK506", *Immunol. Today* 13:136–142 (1992).

Schultz et al., "Cyclosporin A Therapy of Immune–Mediated Thrombocytopenia in Children" *Blood* 85:1406–1408 (1995).

Scott et al., "Identification of an inhibitory region of the heat–stable protein inhibitor of the cAMP–dependent protein kinase", *Proc.Natl.Acad.Sci. (USA)* 82:4379–4383 (1985).

Scott and McCartney, "Localization of A–kinase through Anchoring Proteins", *Mol.Endocrinol.* 8:5–11 (1994).

Shimizu et al., "Acute leucoencephalopathy during cyclosporin A therapy in a patient with nephrotic syndrome", *Pediatr.Nephrol.* 8:483–485 (1994).

Showstack et al., "The Effect of Cyclosporine of the Use of Hospital Resources for Kidney Transplantation", *N.Eng.J.Med.* 321:1086–1092 (1989).

Sinclair, "A Randomized Clinical Trial Of Cyclosporine In Cadaveric Renal Transplantation", *N.Eng.J.Med.* 314:1219–1225 (1986).

Stewart and Young, "Laboratory Techniques in Solid Phase Peptide Synthesis", *Solid Phase Peptide Synthesis*, 2nd Edition.

Stofko–Hahn, "A single step purification for recombinant proteins, Characterization of a microtubule associated protein (MAP 2) fragment which associates with the type II cAMP–dependent protein kinase", *F.E.B.S. Letts.* 302:274–278 (1992).

Sturrock et al., "Acute hemodynamic and renal effects of cyclosporin and indomethacin in man", *Nephrol.Diag.Transplant* 9:1149–1156 (1994).

Svarstad et al., "Renal effects of maintenance low–dose cyclosporin A treatment in psoriasis", *Nephrol.Dial.Transplant* 9:1462–1467 (1994).

Tam et al., "$S_N2$ Deprotection of Synthetic Peptides with a Low Concentration of HF in Dimethlyl Sulfide: Evidence and Application in Peptide Synthesis[1]", *J.Am.Chem.Soc.* 105:6442–6455 (1983).

Tejani et al., "Cyclosporine (CY) Induced Remission of Relapsing Nephrotic Syndrome (RNS) In Children", *Kidney Intl.* 29:206 (1986).

The Canadian Multicentre Transplant Study Group, "A Randomized Clinical Trial of Cyclosporin in Cadaveric Renal Transplantation," *N. Engl. J. Med.* 314:1219–1225 (1986).

Theurkauf and Vallee, "Molecular Characterization of the cAMP–dependent Protein Kinase Bound to Microtubule–associated Protein 2*", *J.Biol.Chem.* 257:3284–3290 (1982).

Thomason et al., "The Periodontal Problems and Management of the Renal Transplant Patient", *Renal Failure* 16:731–745 (1994).

Thomson and Starlz, "New Immunosuppressive Drugs: Mechanistic Insights and Potential Therapeutic Advances", *Immunol.Rev.* 136:71–98 (1993).

Tokuda et al., "Effect of Low–Dose Cyclosporin A on Systemic Lupus Erythematosus Disease Activity", *Arth.Rheumat.* 37:551–0558 (1994).

Toronto Lung Transplant, "Experience With Single–Lung Transplantation for Pulmonary Fibrosis", *JAMA* 259:2258–2262 (1988).

Van Joost et al., "Cyclosporin in atopic dermatitis", a multicentre placebo–controlled study, *Br.J.Derm.* 130:634–640 (1994).

Villafranca et al., "Crystal structures of human calcineurin and the human FKBP12–FK506–calcineurin complex," *Nature* 378:641–644 (1995).

Vogelzang et al., "Subcutaneous Interleukin–2 Plus Interferon Alfa–2a in Metastatic Renal Cancer: An Outpatient Multicenter Trial", *J.Clin.Oncol.* 11:1809–1816 (1993).

Vojtek et al., "Mammalian Ras Interacts Directly with the Serine/Threonine Kinase Raf", *Cell* 74:205–214 (1993).

Walsh et al., "An Adenosine 3',5'–Monophosphate–dependent Protein Kinase from Rabbit Skeletal Muscle*", *J.Biol.Chem.* 243:3763–3765 (1969).

Watanabe et al., "Identification in the Calcineurin A Subunit of the Domain That Binds the Regulatory B Subunit," *J. Biol. Chem.* 270:456–460 (1995).

Weiss and Littman, "Signal Transduction by Lymphocyte Antigen Receptors", *Cell* 76:263–274 (1994).

Wells and Tugwell, "Cyclosporin A in Rheumatoid Arthritis Overview of Efficacy", *Br.J.Rheum.* 32(suppl 1):51–56 (1993).

Whittington et al., "Interleukin–2 A Review of its Pharmacological Properties and Therapeutic Use in Patients with Cancer", *Drugs* 46(3):447–515.

Wilcox et al., "The nucleotide sequence of the araC regulatory gene in *Salmonella typhimurium* LT2," *Gene* 18:157–163 (1982).

Wilcox et al., "The araBAD operon of *Salmonella typhimurium* LT2 II. Nucleotide sequence of araA and primary structure of its product, L–arabinoise isomerase," *Gene* 34:123–128 (1985).

Wilson et al., "Sensorimotor neuropathy resembling CIDP in patients receiving FK506", *Muscle and Nerve* 17:528–532 (1994).

Woodgett et al., "Isolation and Characterization of Two District Forms of Protein Kinase C," *J. Biol. Chem.* 262:4836–4843 (1987).

Wu et al., "Inhibition of the EGF–Activated MAP Kinase Signaling Pathway by7 Adenosine 3',5'–Monophosphate," *Science* 262:1065–1072 (1993).

Young et al., "A prospective study of renal structure and function in psoriasis patients treated with cyclosporin", *Kidney International* 46:1216–1222 (1994).

| | | |
|---|---|---|
| Mu clone 11.1 | ---------- PPPPPPPPPP LGADRVVKAV PFPPTHRLTS EEVFDMDGIP | 40 |
| Hu Calcineurin A1 | MAAPEPARAA PPPPPPPPPP HGADRVVKAV PFPPTHRLTS EEVFDLDGIP | 50 |
| Mu clone 11.1 | RVDVLKNHLV KEGRVDEEIA LRIINEGAAI LRREKTMIEV EAPITVCGDI | 90 |
| Hu Calcineurin A1 | RVDVLKNHLV KEGRVDEEIA LRIINEGAAI LRREKTMIEV EAPITVCGDI | 100 |
| Mu clone 11.1 | HGQFFDLMKL FEVGGSPANT RYLFLGDYVD RGYFSIEVVL ---------- | 130 |
| Hu Calcineurin A1 | HGQFFDLMKL FEVGGSPANT RYLFLGDYVD RGYFSIEVVL GTEDISINPH | 150 |
| Mu clone 11.1 | -------YL WVLKILYPST LFLLRGNHEC RHLTEYFTFK QECKIKYSER | 172 |
| Hu Calcineurin A1 | NNINECVIYL WVLKILYPST LFLLRGNHEC RHLTEYFTFK QECKIKYSER | 200 |
| Mu clone 11.1 | VYEACMEAFD SLPLAALLNQ QFLCVHGGLS PEIHTLDDIR RLDRFKEPPA | 222 |
| Hu Calcineurin A1 | VYEACMEAFD SLPLAALLNQ QFLCVHGGLS PEIHTLDDIR RLDRFKEPPA | 250 |
| Mu clone 11.1 | FGPMCDLLWS DPSEDFGNEK SQEHFSHNTV RGCSYFYNYP AVCEFLQNNN | 272 |
| Hu Calcineurin A1 | FGPMCDLLWS DPSEDFGNEK SQEHFSHNTV RGCSYFYNYP AVCEFLQNNN | 300 |
| Mu clone 11.1 | LLSIIRAHEA QDAGYRMYRK SQTTGFPSLI TIFSAPNYLD VYNNKAAVLK | 322 |
| Hu Calcineurin A1 | LLSIIRAHEA QDAGYRMYRK SQTTGFPSLI TIFSAPNYLD VYNNKAAVLK | 350 |
| Mu clone 11.1 | YENNVMNIRQ FNCSPHPYWL PNFMDVFTWS LPFVGEKVTE MLVNVLSICS | 372 |
| Hu Calcineurin A1 | YENNVMNIRQ FNCSPHPYWL PNFMDVFTWS LPFVGEKVTE MLVNVLSICS | 400 |
| Mu clone 11.1 | DDELMTEGED QFDMGSAAAR KEIIRNKIRA IGKMARVFSV LREESESVLT | 422 |
| Hu Calcineurin A1 | DDELMTEGED QFDHGSAAAR KEIIRNKIRA IGKMARVFSV LREESESVLT | 449 |
| Mu clone 11.1 | LKGLTPTGML PSGVLAGGRQ TLQSGNDVMQ LAVPQMDWGT IHSFANNIHN | 472 |
| Hu Calcineurin A1 | LKGLTPTGML PSGVLAGGRQ TLQSGNDVMQ LAVPQMDWGT HHSFANNSHN | 499 |
| Mu clone 11.1 | ACREILLIFS SCLSS | 487 |
| Hu Calcineurin A1 | ACREFLLFFS SCLSS | 514 |

FIG. 3

MODULATORS OF ANCHORING PROTEIN FUNCTION

This application is a continuation-in-part of U.S. patent application Ser. No. 08/503,226, Filed Jul. 17, 1995, which, in turn, is a continuation-in-part of U.S. patent application Ser. No. 08/404,731, filed Mar. 15, 1995, now U.S. Pat. No. 5,744,354 which, in turn, is a continuation-in-part of U.S. patent application Ser. No. 08/344,227, filed Nov. 23, 1994, now U.S. Pat. No. 5,807,693.

FIELD OF THE INVENTION

The present invention relates generally to regulation of the phosphatase enzymatic activity of calcineurin and modulation of interleukin 2 expression by T cells. More particularly, the present invention relates to inhibition of calcineurin's phosphatase activity by certain peptides and enhancement of T cell expression of interleukin 2 by treatment of the cells with certain other peptides.

BACKGROUND OF THE INVENTION

Calcineurin is a $Ca^{2+}$/calmodulin-dependent protein phosphatase and is a participant in many intracellular signaling pathways. Guerini and Klee, *Proc. Natl. Acad. Sci. USA* 86:9183–9187 (1989). The enzyme has been identified in eukaryotic cells ranging from yeast to mammals. Cyert and Thorner, *J. Cell. Biol.*, 107:841a (1989) and Klee et al., *Adv. Enzymol.*, 61:149–200 (1984). Because calcineurin may participate in many signaling pathways in the same cell, some means of specific targeting of calcineurin's activity must exist. One cellular means for specifically targeting enzyme activity is by compartmentalization. Compartmentalization segregates signaling pathways and contributes to the specificity of cellular responses to different stimuli. Compartmentalization of certain enzymes occurs by interaction of the enzymes with specific anchoring proteins. For example, cAMP-dependent protein kinase (PKA) is anchored at specific intracellular sites by binding to A-Kinase Anchor Proteins (AKAPs). Because AKAPs have been demonstrated to bind proteins other than PKA, the family of proteins is generally referred to herein as anchoring proteins. Hirsch et al., *J. Biol. Chem.*, 267:2131–2134 (1992). cAMP activates PKA by binding to the regulatory subunits (R) of the dormant PKA holoenzyme and causes the release of the active catalytic subunit (C). Two classes of R subunit exist; RI and RII which form the type I and type II PKA holoenzymes, respectively. The subcellular distributions of these PKA isoforms appear to be distinct. The RI isoforms (RIα and RIβ) are reported to be predominantly cytoplasmic and are excluded from the nuclear compartment, whereas up to 75% of the RII isoforms (RIIα or RIIβ) are particulate and associated with either the plasma membrane, cytoskeletal components, secretory granules, the golgi apparatus, centrosomes or possibly nuclei.

Anchoring proteins have been identified in a variety of organisms. At least seven proteins that bind the regulatory subunit of PKA in *Aplysia californica*, a marine invertebrate have been identified. Cheley et al., *J. Biol. Chem.*, 269:2911–2920 (1994). One of these proteins is enriched in crude membrane fractions and taxol-stabilized microtubules and may thus anchor microtubules to the cell membrane as well as bind PKA. A mammalian anchoring protein has been identified that is related to microtubules; microtubule-associated protein 2 (MAP2) attaches PKA to the cytoskeleton. Threurkauf and Vallee, *J. Biol. Chem.*, 257:3284–3290 (1982) and DeCamilli et al., *J. Cell Biol.*, 103:189–203 (1986). The PKA-binding site on MAP2 is a 31-residue peptide in the amino-terminal region of the molecule. Rubino et al., *Neuron*, 3:631–638 (1989) and Obar et al., *Neuron*, 3:639–645 (1989).

Another anchoring protein that associates with microtubules, AKAP 150, accumulates in dendrites in close association with microtubules. Glantz et al., *Mol. Biol. Cell*, 3:1215–1228 (1992). AKAP 150 is present in several neuronal cell types and is a member of a family of anchoring proteins that are the principal anchoring proteins in mammalian brain. Other members of this family include AKAP 75 found in bovine brain and AKAP 79 found in human brain. Glantz et al., *J. Biol. Chem.*, 268:12796–12804 (1993). AKAP 75 apparently binds cytoskeletal elements through two non-contiguous regions near the N-terminus of AKAP 75. AKAP 79 is predominantly present in postsynaptic densities (PSDs) in the human forebrain. Carr et al., *J. Biol. Chem.*, 267:16816–16823 (1992).

Other anchoring proteins have also been characterized. Exposure of granulosa cells to follicle-stimulating hormone and estradiol has been demonstrated to up-regulate expression of an 80 kDa AKAP. Carr et al., *J. Biol. Chem.*, 268:20729–20732 (1993). Another AKAP, Ht31, has been cloned from a human thyroid cDNA library. Carr et al., *J. Biol. Chem.*, 267:13376–13382 (1992). Another anchoring protein, AKAP 95, changes its intracellular location during the cell cycle. AKAP 95 is an integral nuclear protein during interphase, but becomes associated with cytoplasmic PKA when the nuclear membrane breaks down during mitosis. This suggests that AKAP 95 could play a role in targeting activity of certain isoforms of PKA during cAMP-responsive events linked to the cell cycle. Coghlan et al., *J. Biol. Chem.*, 269:7658–7665 (1994). Other known anchoring proteins include an 85 kDa AKAP which links PKA to the Golgi apparatus (Rios et al., EMBO J., 11: 1723–1731 (1992)) and a 350 kDa AKAP that binds PKA to centromeres (Keryer et al., *Exp. Cell Res.*, 204:230–240 (1993)).

The known anchoring proteins bind PKA by a common mechanism. Although the primary structure of the anchoring proteins is not conserved, each has a secondary structure motif that includes an amphipathic helix region. Scott and McCartney, *Mol. Endo.*, 8:5–11 (1994). Binding of anchoring proteins to the regulatory subunit of PKA is blocked by a peptide that mimics this helical structure of the PKA binding region of anchoring proteins. Disruption of the peptide's helical structure by an amino acid substitution abolishes the PKA-anchoring protein binding block (Carr et al., *J. Biol. Chem.*, 266:14188–14192 (1991)), demonstrating that PKA binding occurs in the amphipathic helix of anchoring proteins and is governed by the secondary structure of the anchoring protein molecules. This intracellular binding and localization of PKA by anchoring proteins provides a means for segregation of a kinase that, like calcineurin, is common to many signaling pathways yet may act in a pathway-specific manner.

PKA functions in many intracellular pathways. For example, inhibition of binding between AKAP 79 and PKA in hippocampal neurons has been shown to inhibit alpha-amino-3-hydroxy-5-methyl-4-isoxazole propionic acid/kainate glutamate receptors. Rosenmund et al., *Nature*, 368:853–856 (1994). This indicates that PKA regulates these receptors. PKA also regulates the activity of glycogen phosphorylase by reversibly phosphorylating the enzyme in response to hormonally-induced increases in intracellular cAMP. Walsh et al., *J. Biol. Chem.*, 243:3763–3765 (1969). cAMP has also been shown to inhibit signaling through MAP Kinase pathways. Wu et al., *Science*, 262:1065–1072

(1993). This inhibition is mediated by activation of PKA that inhibits Raf-1 activation by Ras, thereby blocking the MAP Kinase pathway. Vojtek et al., *Cell,* 74:205–214 (1993) and Hafner et al., *Mol. Cell Biol.,* 14:6696–6703 (1994). These pathways are important in many cell types and have been implicated in many cell functions, such as the transcriptional activation of the interleukin 2 gene that is important in activation of T cells. Weiss and Littman, *Cell,* 76:263–274 (1994); Owaki et al., EMBO J., 12:4367–4373 (1993).

Like PKA, calcineurin is associated with T cell activation. Clipstone and Crabtree, *Nature,* 357:695–697 (1992); O'Keefe et al., *Nature,* 357:692–694 (1992). In T cells, calcineurin participates in regulation of IL-2 expression following T cell stimulation. Weiss and Littman, supra. Nuclear factor of activated T cells ($NFAT_p$) has been shown to be a substrate for calcineurin phosphatase activity. It has been suggested that, following T cell stimulation, calcineurin-mediated $NFAT_p$ dephosphorylation allows translocation of $NFAT_p$ from the cytoplasm to the nucleus where $NFAT_p$ interacts with Fos and Jun to induce expression of the IL-2 gene. Jain et al., *Nature,* 365:352–355 (1993).

Calcineurin's role in T cell activation provides a target for therapeutic intervention into T cell-mediated disorders and various medications have been developed that inhibit calcineurin. Two calcineurin-inhibiting drugs, cyclosporin A (cyclosporin) and FK506, have been used in the clinic. Thomson and Starzl, *Immunol. Rev.,* 136:71–98 (1993). Both cyclosporin and FK506 inhibit calcineurin only after binding to distinct intracellular proteins known as immunophilins (cyclophilin and FKBP 12, respectively). Schreiber and Crabtree, *Immunology Today,* 13:136–142 (1992). Thus, cyclosporin and FK506 act as prodrugs. Following binding to their respective immunophilins, the drug/immunophilin complexes bind calcineurin, thereby inhibiting the phosphatase activity.

Calcineurin inhibition has been most effectively exploited in the treatment of graft rejection following organ transplantation. Cyclosporin and FK506 have been employed following renal, hepatic, cardiac, lung, and bone marrow transplants. The Canadian Multicentre Transplant Study Group, *N. Engl. J. Med.,* 314:1219–1225 (1986); Oyer et al., *Transplant Proc.,* 15:Suppl 1:2546–2552 (1983); Starzl et al., *N. Engl. J. Med.,* 305:266–269 (1981); The Toronto Lung Transplant Group, *JAMA,* 259:2258–2262 (1988); and Deeg et al., *Blood,* 65:1325–1334 (1985). The use of these medications has significantly prolonged graft survival and lessened morbidity following transplant. Najarian et al., *Ann. Surg.,* 201:142–157 (1985) and Showstack et al., *N. Engl. J. Med.,* 321:1086–1092 (1989).

Cyclosporin also has been used in a variety of autoimmune-related diseases. Uveitis generally improves within a few weeks of therapy, but quickly relapses after cyclosporin is discontinued. Nussenblatt et al., *Am J. Ophthalmol.,* 96:275–282 (1983). Similarly, psoriasis generally improves with cyclosporin therapy, but quickly relapses after treatment. Ellis et al., JAMA, 256:3110–3116 (1986). "Honeymoon" periods of insulin independence may be induced and prolonged in both new onset Type I and Type II diabetes mellitus when cyclosporin is administered within two months of insulin therapy. Feutren et al., *Lancet,* 2:119–124 (1986) and Bougneres et al., *N. Engl. J. Med.,* 318:663–670 (1988). A variety of nephropathies, including minimal-change focal and segmental, membranous, and IgA-mediated nephropathies, may also be sensitive to cyclosporin, although observed reductions in proteinuria may be due to a decrease in the glomerular filtration rate and not healing of the basement membrane. Tejani et al., *Kidney Intl.,* 29:206 (1986). Cyclosporin administration also has a dose-dependent effect on rheumatoid arthritis, although such treatment is associated with a high incidence of nephrotoxicity. Førre et al., *Arthritis Rheum.,* 30:88–92 (1987).

As mentioned above, cyclosporin has been associated with nephrotoxicity. Mason, *Pharmacol. Rev.,* 42:423–434 (1989). Depressed renal function occurs in virtually all patients treated with cyclosporin. Kahan, *N. Engl. J. Med.,* 321:1725–1738 (1989). This can generally be reversed by cessation of cyclosporin therapy. Unfortunately, in organ graft recipients substitution of other commonly used immunosuppressives for cyclosporin carries a high risk of graft rejection. In renal transplant patients this can require reinstitution of dialysis. In patients that have received hearts, lungs, or livers, graft rejection can be fatal. Although less common than nephrotoxicity, neurotoxicity and hepatotoxicity are also associated with cyclosporin therapy. de Groen et al., *N. Engl. J. Med.,* 317:861–866 (1987) and Kahan et al., *Transplantation,* 43:197–204 (1987).

Significant toxicity has also become apparent in the use of FK506. Like cyclosporin, FK506 is associated with nephrotoxicity. Peters et al., *Drugs,* 4:746–794 (1993). The clinical presentation, lesion morphology, and incidence are approximately equivalent to those of cyclosporin. McCauley, *Curr. Op. Nephrol. Hyperten.,* 2:662–669 (1993). Neurotoxicity has also been associated with FK506. Eidelman et al., *Transplant. Proc.,* 23:3175–3178 (1991) and Fung et al., *Transplant. Proc.,* 23:3105–3108 (1991). In contrast to cyclosporin, FK506 has a hepatotrophic, rather than hepatotoxic, effect. Peters et al., supra.

In view of the significant potential toxicity of immunosuppressive agents, such as cyclosporin and FK506, it is clear that there is a need in the art for additional agents that inhibit calcineurin. These agents would preferably be associated with fewer toxic side effects than presently available agents and thus could provide an advance in immunosuppressive therapy. Additionally, there is a need for agents that inhibit PKA in T cells allowing enhanced expression of interleukin 2 by the cells.

SUMMARY OF THE INVENTION

The present invention is based, in part, on the discovery that calcineurin binds AKAP 79. By binding both PKA and calcineurin, AKAP 79 co-localizes a kinase and a phosphatase that may regulate flux through a specific signaling pathway. The present invention accordingly provides compositions and methods for isolating calcineurin as well as for inhibiting calcineurin activity in a cell. The isolation methods comprise contacting a cellular fraction with AKAP 79 or a calcineurin-binding fragment thereof which has been immobilized to a solid substrate and then eluting calcineurin therefrom. The calcineurin inhibiting methods comprise contacting the cell with AKAP 79 or a calcineurin-binding fragment peptide thereof. Preferably, the calcineurin-binding peptide does not also bind PKA. Preferred peptides comprise the following amino acid sequence:

Arg-Arg-Lys-Arg-Ser-Gln-Ser-Ser-Lys-Glu-Glu-Lys-Pro
(SEQ ID NO:1).

Alternative peptides useful in the practice of the calcineurin inhibiting methods of the present invention include:

```
Arg-Arg-Lys-Arg-Ser-Gln-Ser-Ser-Lys-Glu-Glu-Lys-Pro-Leu-Gln
                        (SEQ ID NO:2)

and

Arg-Arg-Lys-Arg-Ser-Gln-Ser-Ser-Lys-Glu-Glu-Lys-Pro-Phe-Lys
                        (SEQ ID NO:3).
```

These peptides are homologous to amino acid sequences of AKAP 79 that bind calcineurin. Although the peptides are similar to the calcineurin binding region of FKBP12, unlike calcineurin inhibition by the FK506/FKBP12 complex, the peptides inhibit calcineurin activity without requiring interaction with another molecule.

The peptides may be modified to facilitate passage into the cell, such as by conjugation to a lipid soluble moiety. For example, the peptides may be conjugated to myristic acid. Alternatively, the peptides may be packaged in liposomes that may fuse with cell membranes and release the peptides into the cells.

Another aspect of the present invention are methods for determining if a cell contains a calcineurin-binding and PKA-binding anchoring protein. The methods generally comprise lysing the cell to form a lysate; incubating the lysate with a solid support, which solid support has calcineurin molecules immobilized thereon; washing the lysate from the solid support; contacting the solid support with a labeled PKA regulatory subunit, washing unbound regulatory subunit from the solid support; detecting label remaining on the solid support; and determining therefrom the presence of a calcineurin-binding and PKA-binding anchoring protein in the cell. Alternatively, the PKA regulatory subunit may be immobilized on the solid support and calcineurin may be the labeled molecule. Generally, the PKA regulatory subunit will be an RII subunit.

These methods are useful for identifying additional proteins that bind both PKA and calcineurin. Identification of other such proteins may provide tissue specific targets for therapeutic intervention.

Also comprehended by the present invention are methods for identifying compounds that modulate binding between calcineurin and a calcineurin anchoring protein. Either calcineurin or the anchoring protein may be bound to a solid substrate. The unbound binding partner is detectably labeled with, for example, a radio-label, a fluorophore, or by biotinylation. The binding partners are incubated in the presence of a test compound. The effect of the test compound on binding between calcineurin and the calcineurin anchoring protein is determined by observing the amount of label bound to the immobilized binding partner. When the binding partner is biotinylated, the amount of bound binding partner can be effected using fluorophore-labeled streptavidin. A reduction in the amount of label bound in the presence of the test compound compared to the amount of label bound in the absence of the test compound indicates that the test compound is an inhibitor of binding between calcineurin and the calcineurin anchoring protein. Other assays, such as scintillation proximity assays may also be employed.

An additional aspect of the present invention includes methods for enhancing expression of interleukin 2 by T cells. Inhibition of the kinase activity of PKA or localization of PKA in T cells enhances the expression of proteins under the control of the promoter elements that regulate transcription of the interleukin 2 gene. These methods generally comprise contacting the T lymphocyte with one of the following amino acid sequences:

```
          Gly-Arg-Arg-Asn-Ala-Ile-His-Asp-Ile
                    (SEQ ID NO:5), or

Asp-Leu-Ile-Glu-Glu-Ala-Ala-Ser-Arg-Ile-Val-Asp-Ala-Val-Ile-Glu-
              Gln-Val-Lys-Ala-Ala-Gly-Ala-Tyr
                       (SEQ ID NO:9).
```

The peptide of SEQ ID NO:5 is a peptide that inhibits the kinase activity of PKA. The peptide of SEQ ID NO:9 is a peptide that is homologous to a PKA binding region of the Ht31 anchoring protein. These peptides may be modified to facilitate passage into cells or packaged into liposomes as described above. The invention contemplates a variety of uses for the methods employing the peptides. For example, the methods may be employed to stimulate the immune response, to stimulate activated T cells for selected clonal expansion, or to enhance T cell responses to experimental stimuli for evaluation of early events in T cell biology and activation of the immune response.

BRIEF DESCRIPTION OF THE FIGURES

FIG. 3 illustrates homology between clone 11.1 and human calcineurin isoform 11.1.

DETAILED DESCRIPTION OF THE INVENTION

Figure 1A:
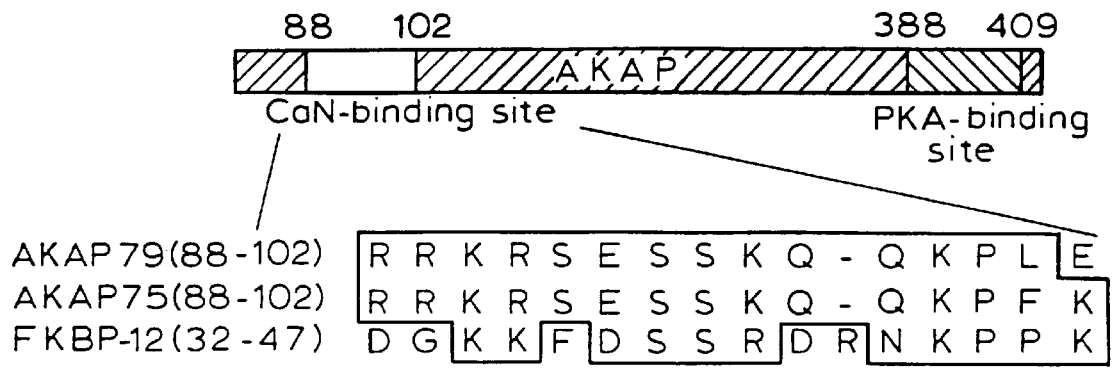
FIGS. 1A–1C illustrate inhibition of calcineurin phosphatase activity by full-length AKAP 79 and a calcineurin-binding fragment of AKAP 79.

The peptides employed in the methods of the present invention may be synthesized in solution or on a solid support in accordance with conventional techniques as described in Stewart and Young, *Solid Phase Peptide Synthesis*, 2nd ed., Pierce Chemical Company, (1984) or Tam et al., *J. Am. Chem. Soc.*, 105:6442 (1983), both of which are incorporated herein by reference. The peptides may be myristoylated by standard techniques as described in Eichholtz et al., *J. Biol. Chem.*, 268:1982–1986 (1993), incorporated herein by reference. Encapsulation of the peptides in liposomes may also be performed by standard techniques as generally described in U.S. Pat. Nos. 4,766,046; 5,169,637; 5,180,713; 5,185,154; 5,204,112; and 5,252,263 and PCT Patent Application No. 92/02244, each of which is incorporated herein by reference.

The following examples are offered by way of illustration and not of limitation. Example 1 describes association of calcineurin with AKAP 79 and PKA. Example 2 relates to inhibition of calcineurin activity using peptides derived from AKAP 79 amino acid sequences. Example 3 addresses subcellular distribution of type II PKA and calcineurin. Example 4 describes a di-hybrid assay that demonstrates physiological binding between AKAP 79 and calcineurin. Example 5 addresses analysis of AKAP 79 and calcineurin binding. Example 6 describes use of calcineurin mutants to define an AKAP 79 binding site. Example 7 relates to interaction between AKAP 79 and PKA RI subunit. Example 8 describes a method to screen for inhibitors of PKA compartmentalization. Example 9 describes anchoring protein participation in modulation of IL-2 expression. Example 10 relates to identification of other AKAP 79 binding proteins. Example 11 describes interaction between AKAP 79 and PKC. Example 12 addresses a high throughput screening assay to identify inhibitors of AKAP 79 RII binding. Example 13 relates to secondary screening techniques for AKAP 79/RII binding inhibitors. Example 14 relates to tertiary screening assay for inhibitors of AKAP 79/RII binding. Example 15 described specificity of AKAP 79 binding to calcineurin. Example 16 describes identification of an AKAP 79 binding site on calcineurin. Example 17 relates to identification of RI and calcineurin binding sites on AKAP 79. Example 18 relates to potential therapeutic application of anchoring proteins.

EXAMPLE 1

This example demonstrates the naturally-occurring association of calcineurin with AKAP 79 and PKA. AKAP 79 thus functions to co-localize both a ubiquitous kinase and ubiquitous phosphatase. This co-localization may provide for specific regulation of enzymes in signaling pathways through phosphorylation or dephosphorylation of the enzymes.

Immunoprecipitation of calcineurin (CaN) from a calmodulin-agarose purified bovine brain extract was achieved using affinity-purified antibodies specific for either CaN A or CaN B subunits as generally described in Harlowe and Lane, *Antibodies: A Laboratory Manual*, Cold Spring Harbor Press, Cold Spring Harbor, N.Y. (1988), except a final wash using buffer A (10 mM HEPES pH 7.9, 1.5 mM MgCl, 10 mM KCl, 1 mM PMSF and 10 $\mu$M IBMX) wherein 0.4 M NaCl was included. PKA activity was measured as described in Scott et al., *Proc. Natl. Acad. Sci. USA*, 82:4379–4383 (1985), incorporated herein by reference, after elution of the immunoprecipitate with 0.1 mM cAMP. Phosphorylation of immunoprecipitated proteins was initiated by addition of 0.1 mM $^{32}$P-ATP ($1.5 \times 10^5$ cpm/nmol) and, after 30 min at 30° C., reactions were terminated by addition of SDS-loading buffer and subjected to SDS-PAGE. PKA R-subunit was purified from the 30–60% $(NH_4)_2SO_4$ fraction of brain extract using cAMP-agarose by the methods described in Coghlan et al., *J. Biol. Chem.*, 269:7658–7665 (1994) (incorporated herein by reference), except protein was eluted with 0.5 mM Ht31 peptide (SEQ ID NO:4). Western blots and PKA RII overlays were performed as described in Coghlan et al., supra.

Kinase activity was detected in the calmodulin purified extract, was enriched 123±3.6 fold (±standard deviation; n=3) in the CaN immunoprecipitate, and was specifically inhibited by a peptide that inhibits PKA kinase activity, PKI peptide (SEQ ID NO:5), indicating that the catalytic (C) subunit of PKA was a component of the isolated complex. The bovine homologue of AKAP 79 (AKAP 75) and RII, both substrates for the C subunit, were also present in the immunoprecipitate and were phosphorylated upon addition of cAMP and $^{32}$P-ATP. In complementary experiments, R subunits of PKA were isolated from crude extracts of bovine brain by affinity chromatography on cAMP-agarose. Treatment of the affinity column with Ht31 peptide specifically eluted AKAP 75 from the cAMP-bound RII and also released both CaN A and B subunits. Approximately 5% of the total CaN present in the lysate was found to be associated with AKAP 75 and RII as detected on Western blots. Combined, these results suggest simultaneous association of PKA and CaN with the anchoring protein.

EXAMPLE 2

This example demonstrates inhibition of the phosphatase activity of calcineurin by peptides from AKAP 79.

To determine whether AKAP 79 peptide binding inhibits CaN activity, CaN phosphatase activity was assayed in the presence of recombinant AKAP 79. Briefly, recombinant AKAP 79 was expressed in *E. coli* as described in Carr et al., *J. Biol. Chem.*, 267:16816–16823 (1992), incorporated herein by reference. CaN and the constitutively active truncation mutant CaN$_{420}$ (a truncated, Ca$^{2+}$/calmodulin independent constitutively active form of CaN (Perrino et al., *J. Biol. Chem.*, in press)) were expressed in Sf9 cells and purified on calmodulin-Sepharose as described in Perrino et al., *J. Biol Chem.*, 267:15965–15969 (1992), incorporated herein by reference. Phosphatase activity toward $^{32}$P RII peptide substrate was measured as described in Perrino et al., supra. CaN (30 nM), calmodulin (100 nM) and $^{32}$P RII peptide (22 $\mu$M) were incubated with AKAP 79 protein and AKAP 79 peptide (SEQ ID NO:1-amino acids 81–102) over the range of concentrations indicated in FIG. 1B. Calmodulin was omitted from CaN$_{420}$ assays. $^{32}$P released from the substrate was measured in triplicate samples in three separate experiments by scintillation counting. The inhibition constant (K$_i$) of recombinant AKAP 79 for CaN was determined by linear regression analysis of data. K$_i$ values for AKAP 79 peptide were estimated by determining the IC$_{50}$ using a fixed substrate concentration at K$_m$ (42 $\mu$M).

Figure 1B:
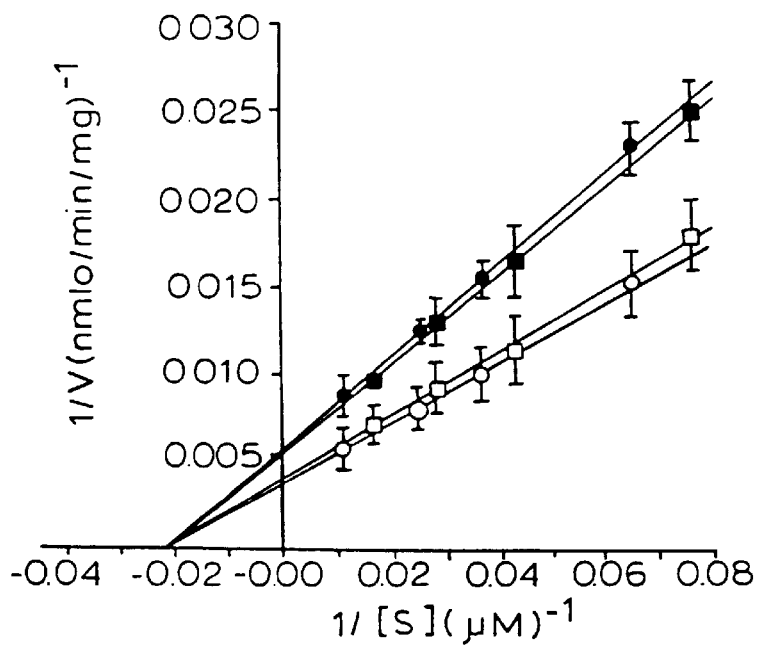
Figure 1C:
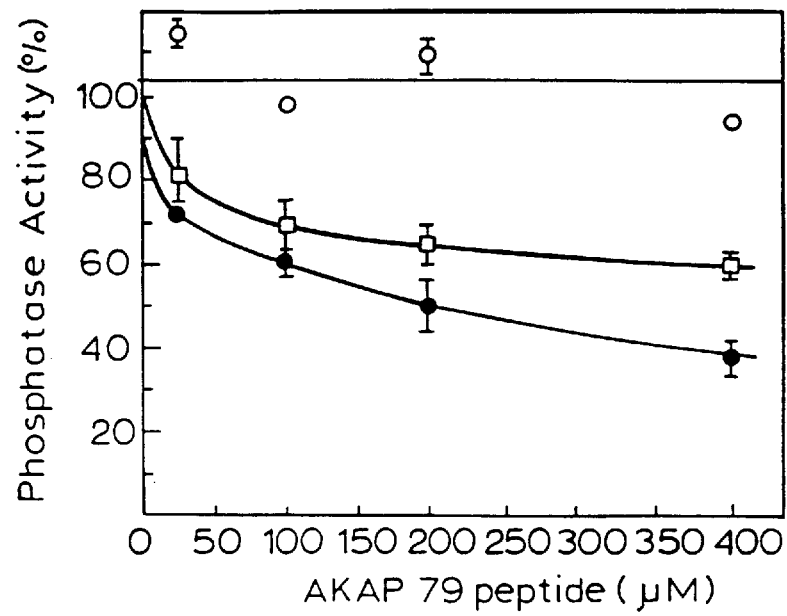

FIG. 1B illustrates a Lineweaver-Burk plot of AKAP 79 inhibition of both full-length CaN (Ca$^{2+}$/calmodulin dependent) (circles) and CaN$_{420}$ (squares) in a non-competitive manner with respect to phosphorylated RII peptide substrate. The open symbols represent phosphatase activity in the absence of AKAP 79 and the filled symbols represent phosphatase activity in the presence of AKAP 79. The synthetic peptide corresponding to the AKAP 79 peptide inhibited both full-length CaN (filled circles) and CaN$_{420}$, whereas the Ht31 peptide was not an inhibitor of CaN (FIG. 1b). The observed inhibition was specific for calcineurin; the AKAP 79 peptide did not significantly affect the activity of protein phosphatases 1 (open diamonds) or 2A (crosses) at peptide concentrations as high as 0.4 mM. Although CaN-binding sites on AKAP 79 and FKBP-12 are similar, their differences may have functional significance: FK506 (2 $\mu$M) did not affect the potency of inhibition and recombinant AKAP 79 did not display peptidyl propyl isomerase activity toward a fluorescent peptide substrate. Further, the CaN B subunit which is required for FK506/FKBP interaction with the CaN A subunit is not required for interaction of AKAP 79 with the CaN A subunit. Also, while the FK506/FKBP interaction with CaN A is calcium/calmodulin dependent, the AKAP 79 inhibition of calcineurin activity is calcium/calmodulin independent. Collectively, these findings suggest that CaN in its inactive state is localized by AKAP 79 in a manner analogous to anchoring protein-bound PKA.

EXAMPLE 3

This example demonstrates subcellular distribution of type II PKA and calcineurin in various tissue.

The subcellular location of many protein kinases and protein phosphatases is defined by association with targeting subunits. AKAP 79 represents a novel member of this class of regulatory proteins as it serves a bifunctional role in localizing both PKA and CaN.

Cells were cultured, formalin-fixed, and immunostained as described in Rosenmund et al., Nature, 368:853–856 (1994). FITC-conjugated anti-goat secondary antisera was used for RII staining. Biotinylated anti-rabbit secondary antisera and streptavidin-Texas-Red (Jackson) were used in staining for CaN. Images were obtained using a Biorad MRC-600 confocal laser scanning system (A1 and A2 filters) with a Nikon optiphot 2 microscope equipped with 60×planappo chromat (1.6 NA) oil immersion lens. Confocal sections were between 1.5 and 2 µm absolute thickness.

Figure 2A:
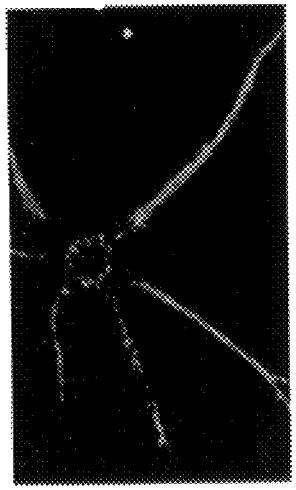
FIGS. 2A–2C illustrate subcellular localization of type II PKA and calcineurin as well as the co-localization of type II PKA and calcineurin.
Figure 2B:
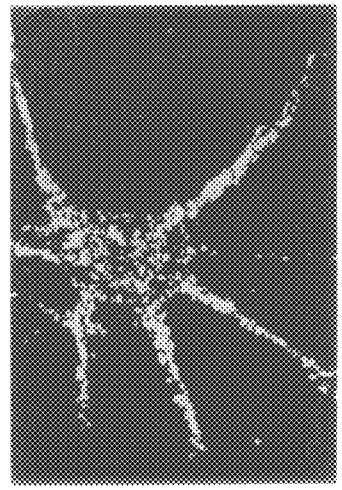
Figure 2C:
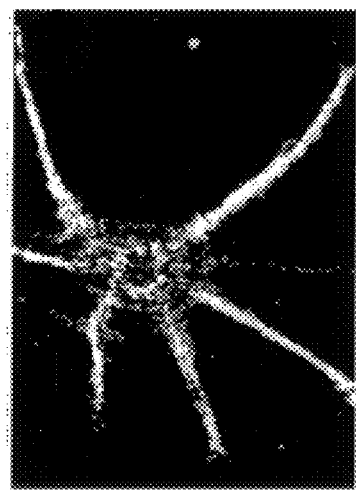

AKAP 79 homologues were observed in bovine, porcine, rabbit, and murine brain. This indicates that co-localization of PKA and CaN may be a universal phenomenon that adapts neurons for specific signal transduction events. Using immunocytochemical methods, the subcellular distribution of type II PKA and CaN was examined in cultured hippocampal neurons. The staining patterns for RII (green label in FIG. 2A) and CaN (red label in FIG. 2B) were regionally dispersed and overlapped in the neurites (RII is red and CaN is green in FIG. 2C). These findings are consistent with co-localization of type II PKA and CaN by the anchoring protein and suggest a role for the ternary complex in regulating synaptic transmission. This observation is consistent with experiments demonstrating co-localization of RII and AKAP 79 in these cells, and studies showing that AKAP 79, type II PKA and CaN are components of postsynaptic densities. Potential substrates for the localized ternary transduction complex may include AMPA/kainate receptors, which are modulated by anchoring protein-targeted PKA.

EXAMPLE 4

This example demonstrates interaction between AKAP 79 and calcineurin in a yeast dihybrid assay. Employing AKAP 79 as the "bait", calcineurin encoded by cDNA from a murine T cell library was found to bind to AKAP 79.

The assay was performed as generally described in Durfee, et al., Genes and Development 7:555–567 (1993), incorporated herein by reference. The "target" and "bait" were two plasmids, each containing part of the Gal-4 transcription factor. The "bait" plasmid (pAS1) was a 2 micron based plasmid with an alcohol dehydrogenase (ADH) promoter linked to the Gal-4 DNA binding subunit [amino acids 1–147 as described in Keegan et al., Science, 231:699–704 (1986), incorporated herein by reference], followed by a hemagglutin (HA) tag, polyclonal site and an ADH terminator. Selection was maintained using SC-Trp media. The "target" construct was a leu2, 2 micron based plasmid containing an ADH promoter and terminator with the Gal-4 transcription activation domain II [amino acids 768–881 as described in Ma and Ptashne, Cell, 48:847–853 (1987), incorporated herein by reference] followed by a multiple cloning site. This vector, pACT, was utilized in the construction of a mouse T cell cDNA fusion library. Saccharomyces cerevisiae y190 used in the screening was designed with two reporter genes integrated into its genome. The reporter genes are under control of a Gal-1 promoter containing Gal-4 binding sites. If the proteins encoded by the bait plasmid and the target plasmid associate, the Gal-4 transcription factor subunits are brought together and function to initiate transcription of the reporter genes.

A 1.3 kb NcoI/BamHI fragment containing the coding region of AKAP 79 was isolated from a pET11d backbone vector band ligated to pAS1 to act as "bait" for the screen. One µg of this construct was transformed into y190 MATa and y190 MATE using a standard lithium acetate-PEG transformation protocol. Four isolates of each mating type (y190A pASI AKAP 79 1–4 and y190α pASI AKAP 79 1–4) were tested for their ability to interact with a fusion construct pACT-RII which contains the regulatory subunit (RII amino acids 1–89) of PKA. This was achieved by mating the strains on YEPD (1% Bacto-yeast extract, 2% Bacto-peptone, 2% dextrose, and 2% Bacto agar) overnight at 30° C. and then selecting for diploids on SC-Leu-Trp plates. The E. coli lac Z gene acting as the reporter could then be assayed for β-galactosidase activity. The mated strains were replicated to SC-Leu-Trp plates that had been overlaid with Hybond-N filters (Amersham) and grown overnight. The filters were placed in liquid nitrogen for one minute to crack open the yeast. A 3 MM paper disc was saturated with approximately 3 ml 0.1% X-gal in 60 mM $Na_2HPO_4$, 40 mM $NaH_2PO_4$, 10 mM KCl and 10 mM $MgSO_4$. The lysed yeast filter was placed on top of the disc and allowed to develop at 30° C. for approximately 1–2 hours. Diploid strains containing both pAS 1 AKAP 79 and pACT RII fusions that were positive for β-gal activity were indicated by turning the yeast patch a blue color. As a control, the bait AKAP 79 plasmid remained white when mated with an empty pACT control.

Detection of the Gal-4 AKAP 79 fusion protein was achieved by growing y190A AKAP 79 (isolates 1 and 2) and y190a AKAP 79 (isolates 1 and 2) to a density of $2 \times 10^7$ cells/ml in 50 ml SC-Trp media. Cells were pelleted at 3000×g for 10 minutes and lysed with 200 µl glass beads (size 425–600 microns) in 25 mM Tris pH8, 5 mM EDTA, 5 mM EGTA, 2 mM O-phenanthroline, 1 mM DTT, 25 µM 4-(2-aminoethyl)-benzenesulfonyl fluoride-HCl, molecular weight 239.5 (AEBSF), 1 mM benzanidine, 1 µg/ml PLACC (pepstatin, leupeptin, aprotinin, calpain I and II), and 20 µg/ml bestantin lysis buffer. Cells were alternately vortexed for one minute and iced for one minute for a total of 24 minutes (12 cycles). Protein concentrations were determined and 30 µg of total protein was loaded onto 10% SDS-PAGE gel. The gel was wet transferred to Immobilon-P (Millipore) and detected by standard procedures using an anti-HA monoclonal antibody 12CA5 (Bab Co., Berkeley, Calif.) and goat anti-mouse IgG alkaline phosphatase conjugated secondary antiserum (Biorad, Hercules, Calif.). A Gal-4 AKAP 79 fusion protein of approximately 100 kDa was readily detectable indicating the correct size product was present within these strains.

The y190A pAS1 AKAP 79 isolate 1 was chosen to screen a pACT murine T cell cDNA library. A 500 ml SC-Trp culture ($OD_{600}$=0.6–0.8) was harvested, washed with 100 ml distilled water, and repelleted. The pellet was brought up in 50 ml LiSORB (100 mM lithium acetate, 10 mM Tris, pH 8, 1 mM EDTA, pH 8, and 1 M Sorbitol), transferred to a 1 liter flask and shaken at 220 RPM for an incubation of 30 min at 30° C. The cells were then pelleted and resuspended with 625 µl LiSORB, and held on ice while preparing the DNA.

The DNA was prepared for transformation by boiling 400 μl 10 mg/ml salmon sperm DNA for 10 min after which 500 μl LiSORB was added and allowed to slowly cool to room temperature. DNA from the mouse T cell library was added (40–50 μg) from a 1 mg/ml stock. The iced yeast culture was dispensed into 10 Eppendorf tubes with 120 μl of prepared DNA. The tubes were incubated at 30° C. at 220 RPM. After 30 minutes, 900 μl of 40% $PEG_{3350}$ in 100 mM Li acetate, 10 mM Tris pH 8 and 1 mM EDTA pH 8 was mixed with each culture and returned to incubate for an additional 30 min. The samples were then pooled and a small aliquot (5 μl) was removed to test for transformation efficiency and plated on SC-Leu-Trp plates. The remainder of the cells were added to 100 ml SC-Leu-Trp-His media and grown for 1 hr at 30° C. with shaking at 220 RPMS. Harvested cells were resuspended in 5.5 ml SC-Leu-Trp-His+50 mM 3AT (3-amino triazole) media and 300 μl aliquots plated on 150 mm SC-Leu-Trp-His+50 mM 3AT and left to grow for 1 week at 30° C.

After four days, titer plates were counted and $1.1 \times 10^5$ colonies were screened. Large scale β-gal assays were performed on library plates and ten positive clones were isolated for single colonies. One of these colonies grew substantially larger than the rest, and was termed clone 11.1. Total yeast DNA was prepared from these strains and leu2 plasmid DNA was isolated. The "rescued" plasmid was used to retransform the original y190A pAS1 AKAP 79 bait strain and y190a. Only clone 11.1 remained positive for β-galactosidase activity in y190A pAS1 AKAP 79. The y190a cells containing only pACT clone 11.1 remained white serving as a negative control.

Restriction digestion with endonuclease XhoI released a 2.3 kb insert and the plasmid was sequenced in the forward and reverse directions. Reactions from the Dye Deoxy Terminator Cycle Sequencing Kit (Applied Biosystems, Inc. Foster City, Calif.) using symmetric polymerase chain reaction (PCR) on double stranded templates were analyzed on an ABI 373A automated sequencer (Applied Biosystems, Inc.). Sequence from clone 11.1 revealed an open reading frame 487 amino acids long (SEQ ID NO:6) which was correctly fused to the Gal-4 activation domain of pACT. The NIH sequence database was searched and the sequence was found to be closely homologous to the human calmodulin dependent protein phosphatase, calcineurin. Computer analysis between clone 11.1 and the human calcineurin isoform A1 showed an 80% identity on the nucleic acid level and 93% identity on the amino acid level (FIG. 3). The first 10 amino acids and an 18 amino acid insert in the human sequence are not present in the mouse 11.1 sequence. Clone 11.1 is closely related to the mouse calcineurin A β sequence, but is distinctly dissimilar at the carboxy-terminus. Likewise the human calcineurin A1 and human calcineurin A2 isoforms are closely homologous but are distinct from each other at their 3' ends.

Specificity of the AKAP 79-calcineurin interaction was demonstrated by mating the calcineurin pACT containing strain with other unrelated bait strains. Crosses were performed as described above with strains containing pAS1 fused to RII (1–89), casein kinase 1, phosphodiesterase 32 (HDUN2) and AKAP Ht31. β-galactosidase activity was negative in all of these diploid strains.

EXAMPLE 5

In order to further evaluate the nature of AKAP 79 interaction with clone 11.1, a series of genes encoding calcineurin 11.1 deletion mutants was constructed, subcloned, and tested in the dihybrid system.

Using the same 5' oligo (MH47) and four 3' oligos (MH48, MH49, MH50 and MH51), PCR reactions were set up to amplify regions of calcineurin 11.1 encoding amino acids 1–104, 1–204, 1–312 and 1–400 respectively. These fragments were digested with BglII and cloned into pACT. Orientation was confirmed by restriction digest mapping and PCR errors determined by automated sequencing. Plasmids determined to properly encode the desired deletion mutant were transformed into y190MATa and y190MATα. Yeast strains were mated with y190apAS1 and y190apAS1 AKAP 79 along with the original clone pACT 11.1 encoding amino acids 1–487 in SEQ ID NO: 6. The resultant mating plate was filter assayed as described above, and it was observed that only fusions protein encoding either amino acids 1–400 or amino acids 1–487 were able to initiate transcription of the reporter gene. The observation that a fusion protein containing amino acids 1–312 was unable to initiate transcription indicated that AKAP 79 binding requires residues between amino acids 313–400. This region has previously been demonstrated to include the FKBP/FK506 binding domain as well as the calcineurin B binding region [Husi, et al., *J.Biol. Chem.*, 269:14199–14204 (1994)].

In order to more precisely defme calcineurin amino acid sequences required for AKAP 79 binding, further deletion mutants were constructed and assayed for AKAP 79 binding. Expression constructs were generated using pACT encoding calcineurin 11.1 domains 332–441, 332–487 and 442–487. As before, each construct was sequenced and determined to express the correct mutant before transformation into the pAS1 AKAP 79 yeast strain.

Upon transformation, however, no reporter gene expression was detected indicating that the mutants were unable to interact with AKAP 79. One possible explanation for the lack of AKAP 79 binding is that secondary protein structure necessary for binding was lost with these truncated clones, or that some amino terminal sequence may also be required for binding.

Previous observations have indicated that interaction between immunophilin complex FKBP/FK506 with calcineurin A requires calcineurin B [Haddy, et al., FEBS 314:37–40 (1992)]. In order to determine if calcineurin B endogenously expressed in yeast strain y190 participated in the observed AKAP 79/calcineurin A binding, a calcineurin B⁻ strain designated y153b (Mat a ga114 ga180 his3 trp1–901 ade2–101 ura3–52 leu2–3–112+URA:: GAL-->lacZ, LYS2::GAL-->HIS3 cnb1Δ1::ADE2) was utilized to eliminate the possibility of calcineurin B participation in calcineurin A/AKAP 79 binding. Initially y153b was transformed with pAS1 and pAS1 AKAP 79 and assayed for β-gal activity in the absence of a prey plasmid. No reporter gene expression was detected indicating that reporter gene expression following transformation with clone 11.1 would necessarily result from AKAP 79/11.1 binding. Plasmids pACT calcineurin 11.1 and pACT calcineurin 1–400 were then separately introduced into y153b1 pAS1 AKAP 79 through standard procedures. β-gal activity was observed in strains transformed with each plasmid indicating that the interaction between AKAP 79 and calcineurin A does not require calcineurin B. This result further suggests that binding of the immunophilin complex FKBP/FK506 to calcineurin A is distinct from AKAP 79 binding.

EXAMPLE 6

In order to attempt to more precisely define the region of AKAP 79 binding on calcineurin 11.1, an additional series of plasmids encoding deletion mutations, unique from those described above, or point mutations was constructed.

A. Terminal Deletions

This example demonstrates the interaction between AKAP 79 and calcineurin 11.1 requires residues 30–336 of calcineurin. Briefly, primers were designed to various regions of calcineurin 11.1 for use in PCR reactions to create specific N-terminal and C-terminal deletions as described in Table 1. PCR products were generated by mixing 1 μg of each 3' and 5' primer with 200 μg each dNTPs and 1 ng of plasmid template with PCR buffer #2 (containing 20 mM Tris-HCl, pH 8.75, 10 mM KCl 10 mM $(NH_4)_2SO_4$, 2 mM $MgSO_4$, 0.1% Triton X-100, and 100 μg/ml BSA) (Stratagene) and 2.5 units *Pyrococus furiosus* (Pfu) DNA polymerase (Stratagene) in a 100 μl reaction volume. Thirty cycles were carried out, each one minute at 95° C., two minutes at 50° C. and four minutes at 72° C. Amplification products were purified and cloned in a BglII site of pACT. Resultant constructs were analyzed for PCR errors and orientation by sequencing as previously described.

Each construct was individually transformed into y190α, y190 a pASI APAK79 and y153b pASI AKAP 79 yeast strains, each described above in Example 4, and β-galactosidase filter assays were performed also as previously described. Results using a first set of vectors encoding C-terminal deletions defined an area between amino acid 312–400 required for AKAP 79 binding. Positive filter assays from the y153b pASI APAK 79 transformants also confirmed that calcineurin B was not required for AKAP 79 binding.

Previous studies have indicated that binding of calcineurin B requires amino acids 348, 349, 355 and 356 [Watanabe, et al., *J.Biol. Chem.* 270:456–460 (1995)], the calcineurin autoinhibitory domain includes amino acids 442–487 [Klee, supra], and FKBP/FK506 binding requires amino acids 350, 353 and 359 [Kawamura and Su, *J.Biol. Chem.* 270:15463–15466 (1995)]. Additional calcineurin 11.1 constructs encoding further C-terminal deletions indicated that the calcineurin 11.1/AKAP 79 binding required amino acids 1–336. These deletions demonstrate the calmodulin binding domain, the autoinhibitory domain and the calcineurin B binding domain are not required for AKAP 79 and calcineurin A to form a complex.

Binding results for all deletions are presented in Table 1. Amino deletions indicated that at least one area required for AKAP 79 binding lies between residues 30–99. As before, y153b pASl AKAP 79 transformants expressing N-terninal deletions did not require calcineurin B for-binding.

TABLE 1

| AKAP 79/Immunophilin Binding to Calcineurin Deletion Mutants | | | |
|---|---|---|---|
| Calcineurin Deletion (designation by primers* used to construct expression plasmid) | Amino Acid Sequence | AKAP 79 Binding | Immunophilin Binding |
| MH52-MH58 | 1-487 | + | N.D. |
| MH52-MH48 | 1-400 | + | N.D. |
| MH52-MH49 | 1-312 | - | N.D. |
| MH52-MH50 | 1-204 | - | N.D. |
| MH52-MH51 | 1-104 | - | N.D. |
| MH66-MH58 | 332-487 | - | N.D. |
| MH59-MH58 | 441-487 | - | N.D. |
| MH66-MH57 | 332-441 | - | N.D. |
| MH52-MH75 | 1-375 | + | + |
| MH52-MH74 | 1-354 | + | - |
| MH76-MH75 | 30-375 | + | + |
| MH77-MH75 | 98-375 | - | - |
| MH52-MH93 | 1-347 | + | N.D. |
| MH52-MH94 | 1-340 | + | N.D. |
| MH52-MH95 | 1-330 | - | N.D. |
| MH52-MH96 | 1-320 | - | N.D. |
| MH52-MH107 | 1-338 | + | N.D. |
| MH52-MH108 | 1-336 | + | N.D. |
| MH52-MH109 | 1-334 | - | N.D. |

TABLE 1-continued

| | | | | |
|---|---|---|---|---|
| MH52-MH110 | 1-332 | - | N.D. | |
| MH52-MH111 | 1-335 | - | N.D. | |

*Primers used to construct expression plasmids
```
MR48  (SEQ ID NO: 10) 5'-GTATTAGCAGGAGATCTTCCTACTTC-3'
MH49  (SEQ ID NO: 11) 5'-GTGTGTGTAGATCTGGTGAAAGTCC-3'
MH50  (SEQ ID NO: 12) 5'-ATTGTAGAGATCTAAGTAATTAGGTGCCG-3'
MH51  (SEQ ID NO: 13) 5'-GCCAATTGCTCAGATCTTGTTTCTTATG-3'
MH52  (SEQ ID NO: 14) 5'-GGAATTCGGATCCTCGAGAGATCTCGCCG-3'
MH57  (SEQ ID NO: 15) 5'-CCACTTTGAGATCTCTACCGTCCTCCAGCC-3'
MH58  (SEQ ID NO: 16) 5'-CCCTGAGATCTTCAGCTGCTAAGAC-3'
MH59  (SEQ ID NO: 17) 5'-GGCTGAGATCTGGCAGACCTTGCAAAGTGG-3'
MH66  (SEQ ID NO: 18) 5'-GTGATGAAGATCTTACAGTTTAATTGCTCTCC-3'
MH74  (SEQ ID NO: 19) 5'-TTCTCCAGATCTTGGTAAGGACCATG-3'
MH75  (SEQ ID NO: 20) 5'-CACCTTCTGTAGATCTTTCATCATCAGAAC-3'
MH76  (SEQ ID NO: 21) 5'-CATCGGCAGATCTCTGAAGAAGTG-3'
MH77  (SEQ ID NO: 22) 5'-CCATGGCCAATTTTAGATCTCGATGAAAC-3'
MH93  (SEQ ID NO: 23) 5'-GGACCATGAGATCTAATCCATAAAATTGGG-3'
MH94  (SEQ ID NO: 24) 5'-AAATGGGAGATCTAATAAGGATGTGGAGAGC-3'
MH95  (SEQ ID NO: 25) 5'-GGAGAGCAATTAAAGATCTAAATGTTCATCAC-3'
MH96  (SEQ ID NO: 26) 5'-TTTTCATAGATCTATACAAGCAGCTTT-3'
MH107 (SEQ ID NO: 27) 5'-CAACCAGATCTAATGTGGAGAGCAATTAAACTGTCG-3'
MH108 (SEQ ID NO: 28) 5'-CCAATAAGAGATCTAAGAGCAATTAAACTGTCG-3'
MH109 (SEQ ID NO: 29) 5'-TGTGAGATCTAATTAAACTGTCGAATGTTCATCAC-3'
MH110 (SEQ ID NO: 30) 5'-GGAGAGCAGATCTACTGTCGAATGTTCATCAC-3'
MH111 (SEQ ID NO: 31) 5'-AAGGATAGATCTAGCAATTAAACTGTCGAATGTTCATCAC
```

B. Point Mutations

In order to evaluate precisely which amino acids participate in AKAP 79 binding, calcineurin 11.1 point mutations were created using a PCR based strategy. Three alanine mutants, $Cys^{335} \rightarrow Ala$, $Ser^{336} \rightarrow Ala$, and $Pro^{339} \rightarrow Ala$, were generated and assayed for modulation of AKAP 79 binding in the dihybrid system. None of these mutants prevented AKAP 79 binding to calcineurin indicating that modification of these residues alone is insufficient to disrupt AKAP 79 binding.

EXAMPLE 7

Additional screening using pACT the mouse Mu T-cell library DNA and the pASI AKAP 79 bait strain was performed in order to identify other AKAP 79 binding proteins by the protocol described above. Results from screening approximately 211,000 colonies gave one positive clone designated pACT 2-1 which remained positive following rescue and retransformation. The library sequence was removed from the plasmid with XhoI digestion and shown to be a 1200 bp insert. Sequencing and a subsequent data base search indicated that the clone had 91% identity with rat type 1α regulatory subunit of protein kinase A (RI).

The library was rescreened using the same AKAP 79 bait and fifteen positives were detected from approximately 520,000 transformnants. Of these fifteen, eleven were found to be homologous to the rat regulatory subunit type I of PKA. Each of these isolates were fused to the 5' untranslated region of RI and remained open through the initiating methionine. Based on restriction digest analysis and sequencing data, nine individual clones were isolated, including the original pACT 2-1 isolate.

These results are the first demonstration of an anchoring protein which binds both RII and RI regulatory subunits of PKA, which is unexpected in view of structurally dissimilar primary structures between the two subunits.

In order to attempt to further defme the sequence of interaction between RI and AKAP 79, and to determine if the interaction is unique to AKAP 79, new yeast strains were developed. Utilizing a BglII site within the first 400 base pairs of RI, a fragment encoding amino acids 1–80 was isolated from pACT72 and ligated to pAS1 and pACT. Orientation was confirmed by restriction digest analysis. Using standard yeast transformation procedures, plasmid DNA was introduced into y190 MAT a and the transformed yeast assayed for β-gal activity. The truncated RI fusion product was determined to be unable to promote expression of the reporter gene. The transformed strains were subsequently utilized in a series of experiments to determine if the truncated RI form would interact with AKAP 79.

Reporter gene expression was observed in the doubly transform yeast strain indicating that RI/AKAP 79 binding was effected via the first 80 amino acids of RI.

Finally, in an effort to determine if the ability to bind both RI and RII subunits was unique to AKAP 79, a human thyroid AKAP [Carr, et al., *J.Biol. Chem.* 267:133376–133382 (1992)], the gene product of pACT Ht31, was assayed by the dihybrid screen with the above described truncated RI peptide containing amino acids 1–80 and encoded on plasmid pASI(1–80). The observed Ht31/RI binding, in combination with a previous observation that Ht31 binds RII indicated that anchoring protein binding with both RI and RII is not unique to AKAP 79.

EXAMPLE 8

In view of the fact that AKAP 79 was shown to bind both RI and RII subunits of PKA, a scintillation proximity screening technique was developed to identify specific inhibitors that disrupt localization of PKA by interfering with AKAP 79 binding to PKA.

Initially, a thioredoxin TRX-AKAP 79 fusion protein expression plasmid was constructed. See, generally, LaVallie, et al., BIO/TECHNOLOGY 11:187–193 (1993). Briefly, a XhaI/HindIII thioredoxin fragment was subcloned into pUC 19 containing a lac Z gene and a tacZ promoter. The resulting plasmid was designated TRX F/S pUC19. In order to insert an AKAP 79 encoding sequence into TRX F/S pUC19, an NcoI site was created with an oligonucleotide (SEQ ID NO:32) having terminal SpeI and HindIII sequences. Following SpeI/HindIII digestion, the oligonucleotide was inserted into the vector and an NcoI/XhoI fragment encoding AKAP 79 was ligated in frame with the thioredoxin gene. The fusion protein was expressed in *E. coli* and immobilized on 96-well ScintiStrip plates (Wallac, Turbu, Finland) which contained a scintillator embedded in the solid support. The plates were precoated with a rabbit anti-mouse antibody which was used to immobilize a mouse monoclonal antibody immunospecific for TRX. The TRX-AKAP 79 fusion protein was then captured on the plates via the anti-TRX antibody, and $^3$H-RII was added to the plates in the presence or absence of a reference inhibitor, for example, unlabeled RII. When $^3$H-RII bound to AKAP 79, the label was brought sufficiently close to the support-embedded scintillator, resulting in emission detected in a MicroBeta scintillation counter.

Results from this assay indicated that unlabeled RII and the Ht31 peptide, described above, were able to inhibit AKAP 79/RII binding with an $IC_{50}$ of 1 nM and 50 nM, respectively. These results are similar to the reported values of other anchoring proteins [Carr, et al., *J.Biol. Chem.* 267:13376–13382 (1992)]. The proline-substituted Ht31 peptide, also described above, did not block AKAP 79/RII binding. Because these results were consistent with those observed in previous Western blotting and overlay assays, it is presumed that this technique will permit rapid screening of potential inhibitors of AKAP 79/RII binding, as well as inhibitors of AKAP 79 binding to other known physiological partners, for example calcineurin and protein kinase C.

EXAMPLE 9

This example demonstrates that association of PKA with an anchoring protein in T cells modulates the activity of PKA on NFAT activation thus modulating interleukin 2 production.

The expression of the IL-2 gene is tightly linked to T cell activation. IL- 2 transcription was studied following activation with PMA and ionomycin. These two agents are known respectively to potentiate protein kinase C and calcium second messenger responses (including activation of CaN). Protein kinase C activates the Ras-Raf-1-Mek-MAP Kinase pathway that participates in induction of the nuclear component of NFAT. The increased calcium concentration activates calcineurin which, in turn, activates the cytoplasmic component of NFAT and allows translocation to the nucleus. This activation of the NFAT components induces IL-2 gene expression. To quantitate transcription, a Jurkat T cell line (NFATZ) was stably transfected with a vector containing 3 tandem copies of the NFAT-binding site, and the minimal IL-2 promoter fused to the lacZ gene encoding β-galactosidase (β-gal). Quantitation of IL-2 transcription was achieved through fluorescence-activated cell sorter (FACS) analysis of β-gal activity.

Typically, 1×10$^6$ NFATZ cells in 1 ml of culture medium were pre-incubated for 60 min at 37° C. with varying concentrations of cyclosporin, and myristilated peptides including amino acids 81–108 of AKAP 75 (SEQ ID NO:8; described in Glantz et al., *J. Biol. Chem.,* 268:12796–12804 (1993), incorporated herein by reference), PKI (a PKA inhibitor peptide (GRRNAIHDI-SEQ ID NO:5)), and a peptide of Ht31 (SEQ ID NO:9; amino acids 493–515 of the full length Ht31 protein described in Carr et al., *J. Biol. Chem.,* 267:13376–13382 (1992), incorporated herein by reference, that blocks anchoring protein interaction with the RII subunit of PKA). Each of the peptides was myristilated as described in Eichholtz et al., *J. Biol. Chem.,* 268:1982–1986 (1993).

Figure 4:
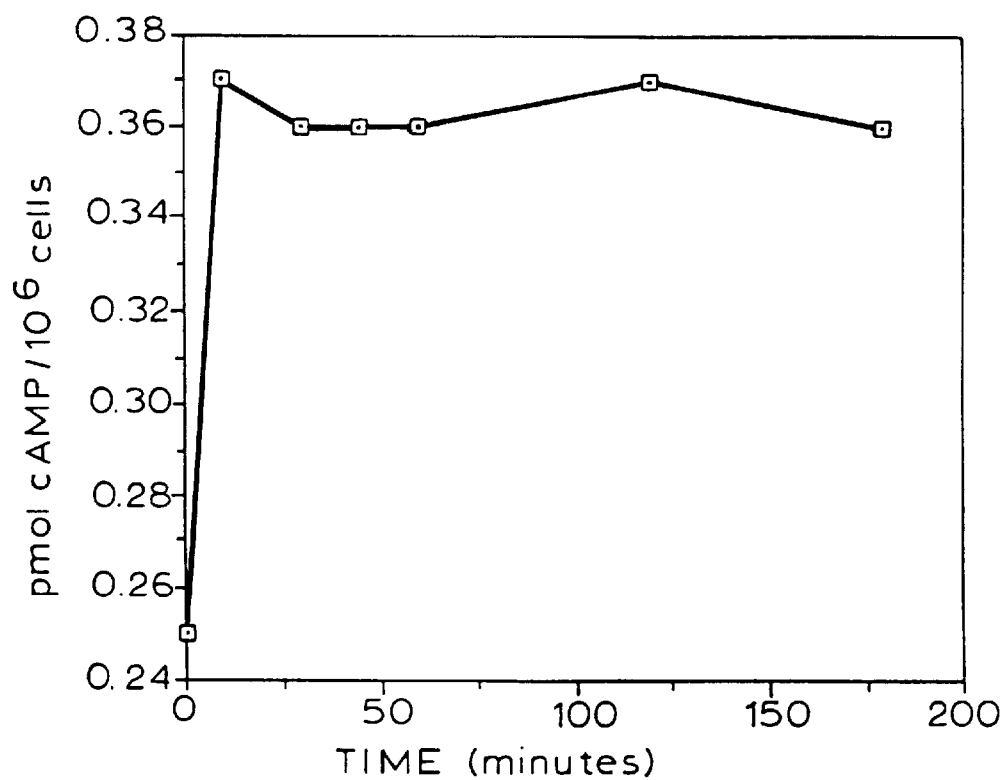
FIG. 4 illustrates the increase in intracellular cAMP concentration induced by treatment of Jurkat cells with forskolin and IBMX.

In the experiments with cyclosporin, PKI (SEQ ID NO:5), and an Ht31 peptide (SEQ ID NO:9), incubation with cyclosporin or the respective peptides was followed by a further 30 min incubation with 25 μM forskolin and 0.1 mM iso-butyl-methyl-xanthine (IBMX). Incubation with forskolin/IBMX elevates intracellular cAMP concentrations (FIG. 4), thereby activating PKA. Finally, phorbol 12-myristate 13-acetate (PMA) (10 ng/ml) and ionomycin (2 μM) were added and incubations continued for 4 hr. Controls were incubated with PMA/ionomycin alone or forskolin/IBMX and PMA/ionomycin under conditions as described above. During the last 20 min of the PMA/ionomycin incubation, chloroquine (300 μM) was added to inhibit endogenous lysosomal β-gal activity. The cells were spun out and resuspended in 50 μl of culture medium to which 50 μl of fluorescein di-β-D-galactopyranoside (FDG) was added (0.1 mM final concentration; Molecular Probes). This osmotic shock procedure continued for 75 seconds before returning the cells to isotonic conditions by the addition of 1 ml cold FACS buffer (including chloroquine). The lacZ β-gal activity was measured by flow cytometry configured for fluorescence analysis.

Figure 5A:
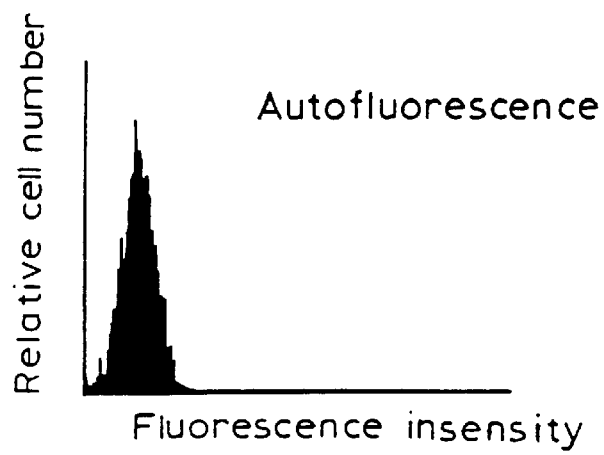
FIGS. 5A–5H illustrate FACS plots that demonstrate the effect of PKA inhibition and delocalization on transcription of proteins controlled by the interleukin 2 promoter.
Figure 5B:
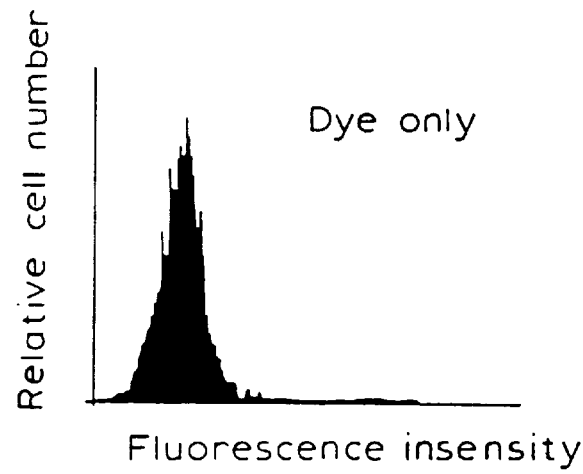
Figure 5C:
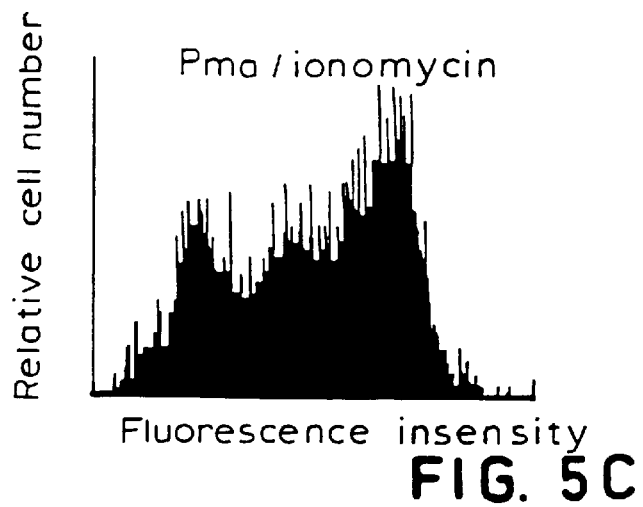
Figure 5D:
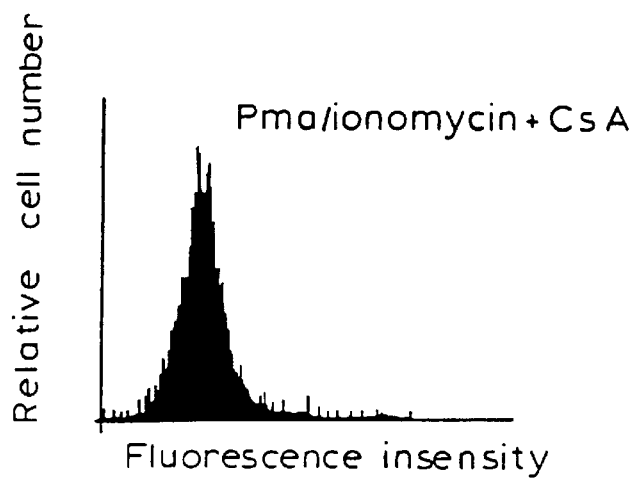

FIGS. 5A–5H illustrated the results of this experiment. FIGS. 5A and 5B are FACS plots showing the background fluorescence of the assay with and without added dye. FIG. 5C shows that PMA/ionomycin treatment of NFATZ Jurkat cells induced a 6–7 fold increase in β-gal activity. Cyclosporin (CsA) completely abolished this activity as would be expected for the important signaling role of CaN in IL-2 transcription (FIG. 5D). The myristilated AKAP 75 peptide (SEQ ID NO:8) when used at 10 μM in the medium was found to reduce PMA/ionomycin induced β-gal activity by 40–50%.

Figure 5E:
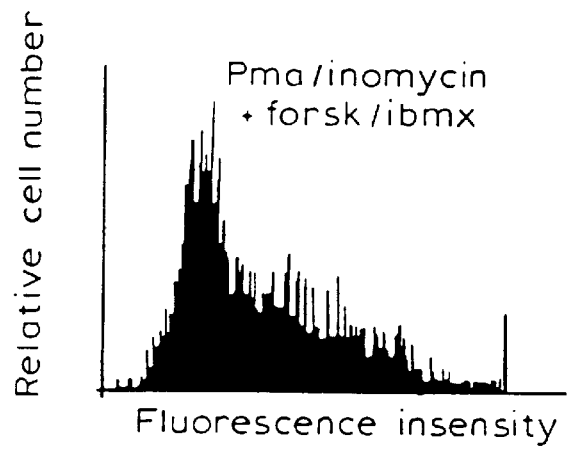
Figure 5F:
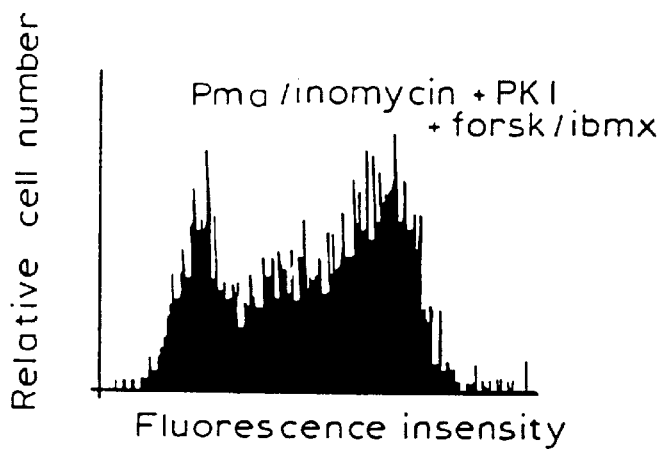
Figure 5G:
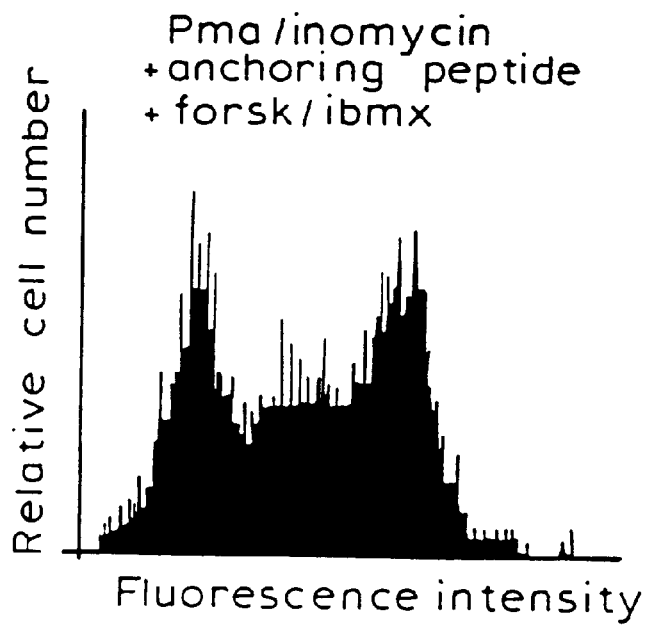
Figure 5H:
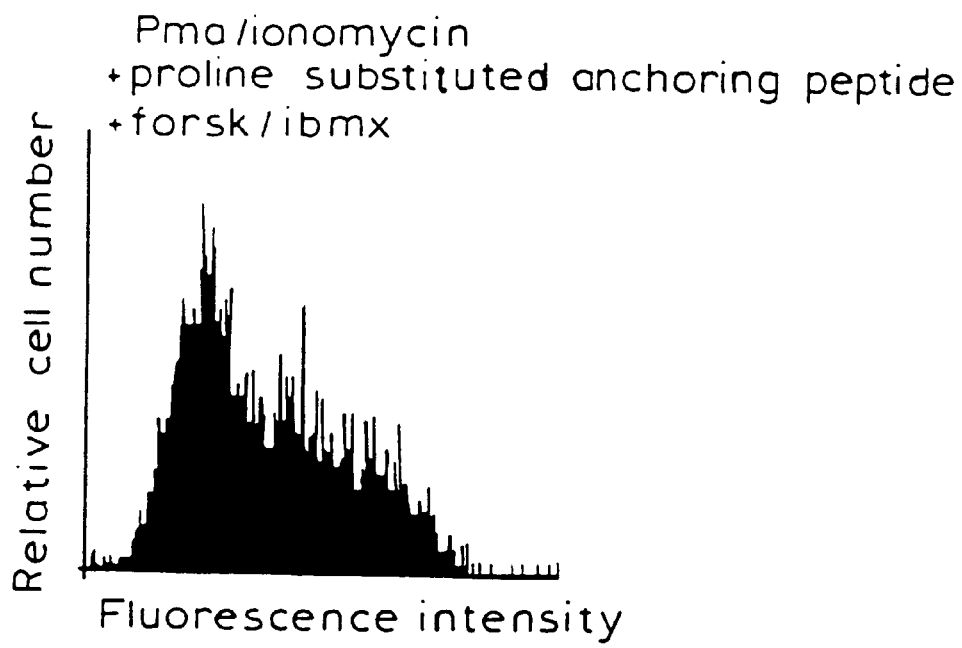

FIG. 5E shows that forskolin and IBMX reduced PMA/ionomycin induced β-gal activity by approximately 50%. This blockade was completely reversed by both 100 μM myristilated PKI peptide (SEQ ID NO:5) and 100 μM myristilated Ht31 peptide (SEQ ID NO:9) (FIGS. 5F and 5G). FIG. 5H shows that a myristilated Ht31 peptide with a proline substitution which is known to render the peptide inactive in blocking PKA anchoring did not affect the forskolin/IBMX blockade. These results demonstrate the importance of PKA and its localization through an anchoring protein in regulating IL-2 gene expression. As described above, interfering with PKA activity or localization may be used for enhancing the immune response, activating T cells for selective clonal expansion or investigation of early events of T cell activation.

EXAMPLE 10

In addition to the AKAP binding proteins identified in Examples 4 and 7, two other unique isolates, designated pACT 59 and pACT 74, were identified which encoded for the same region for another protein. The sequences for these clones are set out in SEQ ID NOs: 33 and 34, respectively. Blast search results indicated significant amino acid homology with three genes products of unknown function: *C. elegans* (a 319 amino acid protein, designated No. U00032 in the data base listing), human fetal brain expressed sequence tag (a 97 amino acid protein, designated T08697), and HL60 expressed sequence tag (a 90 amino acid protein, designated D20731). Homology was also found between an *S. pombe* gene product designated PAD 1$^+$ (a 308 amino acid protein, designated D31731) which has been shown to be a positive regulator of PAP1+, an AP-1 like transcription factor.

In addition, two other positive clones were detected in this screen; pACT 36, which encoded a 143 amino acid open reading frame correctly fused to Ga14, and pACT 60, which encoded a slightly shorter region resulting from an apparent deletion. Sequences for these clones are set out in SEQ ID NOs: 35 and 36, respectively. The two isolates were unique from each other and showed no identity with any known sequence in the NIH database.

EXAMPLE 11

Previous work (see Examples 4 and 7) suggests that AKAP 79 is a multifunctional anchoring protein which is able to associate with at least two signaling enzymes; PKA and the $Ca^{2+}$/calmodulin-dependent phosphatase calcineurin (CaN). Each signaling enzyme binds to a distinct region of the anchoring protein and each enzyme is inhibited when anchored. In addition, it has been demonstrated that $Ca^{2+}$/phospholipid-dependent protein kinase C (PKC) binds to AKAP 79 as well, in a region distinct from that of PKA and CaN. Like PKA and CaN, activity of PKC is inhibited by its association with the anchoring protein. The PKC-binding site is contained within the first 75 residues of the anchoring protein and peptide studies have shown that a fragment containing residues 31–52 of AKAP 79 inhibits PKC activity. Furthermore, evidence suggests calmodulin (CaM) binding to the anchoring protein may release PKC activity suggesting competition for an AKAP 79 sequence. In order to more fully characterize PKC interaction with AKAP 79, experiments were undertaken to characterize the PKC-binding site, isolate the PKC/AKAP complex from bovine brain and determine if CaM is a physiological regulator of PKC/AKAP 79 interaction.

A PKC overlay was initially performed on bovine brain lysates using rabbit brain PKC as a probe. PKC-binding was detected with a monoclonal antibody (M7) which recognizes the PKC$\alpha$ and $\beta$ isoforms. Several PKC-binding proteins were detected ranging in size from 50–300 kDa and included a protein that migrated with a similar mobility as a prominent 75 kDa RII-binding protein. Control experiments confirmed that PKC-binding was specific and could be detected only in the presence of 1.2 mM $CaCl_2$ and 20 µg/ml phosphatidylserine, and when PKC was added to the reaction mixture.

In order to determine if the 75 kDa protein identified may be the bovine homolog of AKAP 79, the PKC overlay assay was used to probe AKAP 79 and related fragments. Briefly, proteins were separated by SDS-polyacrylamide electrophoresis (SDS-PAGE) and blotted to nitrocellulose following standard protocols. Samples were blocked in Blotto [1 mg/ml bovine serum albumin (BSA), 5% dry milk in Tris-buffered saline (TBS)] and incubated for one hour at room temperature in assay buffer [TBS containing 1 mg/ml BSA, 1.2 mM calcium, 1 mM EGTA, 20 µg/ml phosphatidylserine (PS), 2 µg/ml leupeptin, 2 µg/ml pepstatin and 3 µg/ml of partially purified rabbit brain PKC]. Bound PKC was detected with monoclonal antibody M7, which recognizes both PKC$\alpha$ and $\beta$, following standard chemiluminescent detection methods.

PKC bound to the full-length recombinant AKAP 79 protein, and recombinant fragments encompassing the first 75 residues of the protein bound PKC, but C-terminal fragments covering the CaN and RII-binding regions did not. Control experiments demonstrated that $^{32}$P-radiolabeled RII bound to both full-length AKAP 79 and the C-terminal fragments. These results showed that AKAP 79 is a PKC-binding protein and that the principle binding site resides within the first 75 amino acids of the protein.

Previous studies on PKC-binding proteins have suggested that basic and hydrophobic regions from PKC-binding sites participate in formation of a phospholipid bridge with the enzyme. The first 75 residues of AKAP 79 contain a basic and hydrophobic region between positions 31–52 and several lines of evidence suggest that this region is a principle site of contact with PKC. A synthetic peptide to residues 31–52 blocked PKC/AKAP 79 interaction as assessed by the overlay assay.

In order to asses the ability of these peptides to modulate PKC activity, the following assay was performed in the presence and absence of AKAP 79 peptide fragments. PKC [50 nM dissolved in 50 mM tris-HCl (pH 7.4), 5 mM $MgCl_2$ 1.2 mM $CaCl_2$, 1 mM DTT, 1 mM EGTA and 100 µg/ml PS] was incubated with EGF receptor peptide substrate (5 µM) at 30° C. for five minutes. Phosphorylation reaction was initiated by addition of 100 µM $^{32}$P-ATP (500 cpm/pmol) and the reaction allowed to proceed for ten minutes at 30° C. Aliquots of reaction mixture were removed and spotted into P81 filter paper and the reaction terminated by washing the filter paper with excess 75 mM phosphoric acid (three washes for three minutes each). After a final wash in ethanol, the p81 filters were dried and radioactivity was measured by liquid scintillation counting.

The peptide containing residues 31–52, as well as a recombinant fragment to the first 75 amino acids of AKAP 79, were potent inhibitors of PKC activity with $IC_{50}$ of 2 µM and 25 nM, respectively. More detailed kinetic analysis showed that the AKAP 79 31–52 peptide exhibited mixed inhibition of PKC activity with a $K_i$ of 1.411±0.28 µM using the epidermal growth factor (EGF) receptor peptide as a substrate. In addition, this region also resembles a CaM-binding domain, and incubation of the recombinant 1–75 fragment or the 31–52 peptide with CaM (15 µM) prevented inhibition of PKC in the presence of excess $Ca^{2+}$. Since AKAP 79 is a CaM-binding protein, these findings suggest that $Ca^{2+}$/CaM may regulate PKC binding to the anchoring protein.

Combined, these results suggest that PKC associates AKAP 79 in vitro, the PKC-binding site is contained within the first 75 residues of AKAP 79, and peptides encompassing residues 31–52 inhibit PKC activity. Results also suggest that PKC/AKAP 79 interaction may be regulated by CaM as incubation with excess $Ca^{2+}$/CaM prevents inhibition of PKC by the 31–52 peptide (FIG. 3). In order to more fully understand the nature of AKAP 79/PKC interaction, experiments were designed to 1) identify residues important for PKC binding to AKAP 79, 2) isolate a PKC/AKAP 79 complex from cells and 3) establish whether CaM regulates PKC/AKAP 79 interaction.

Sequence analysis of several PKC-binding proteins has suggested that a highly positive surface charge may be required for association with the PKC. Consistent with this hypothesis are previous results wherein a peptide fragment of AKAP 79 amino acids 31–52 which encompasses a cluster of basic and hydrophobic residues inhibits PKC activity ($K_i$ of 1.4±0.28 µM) and a recombinant fragment to this region is an even more potent inhibitor of the kinase ($IC_{50}=25\pm5$ nM). In order to assess the role of basic side-chains located between residues 31–52 of AKAP 79 as determinants for PKC inhibition, a family of AKAP 79 mutants are generated in a recombinant AKAP 79 polypeptide containing amino acids 1–75, and PKC binding properties of each mutant assayed by the overlay method and for changes in inhibitory potency toward PKC βI.

Five AKAP 79 mutants are constructed in which clusters of basic residues are replaced with alanine. Given the high density of positive charge, it is likely that simultaneous substitution of several basic side chains will be necessary before significant changes in PKC-binding affinity are recorded. Therefore, multiple basic residues are substituted. Point mutants in the AKAP 79 sequence are created by alanine scanning mutagenesis using the methods described by Hausken, et al. [*J.Biol. Chem.* 269:24245–24251 (1994)] Each AKAP 79 protein is expressed as a poly-histidine tag fusion protein and purified to homogeneity by nickel affinity chromatography. The alanine mutant peptides are shown below. SEQ ID NO: 37 is the native AKAP 79 sequence.

```
AKAP 79 (37-50)   FXRRKKAAKALAPK   (SEQ ID NO: 38)

AKAP 79 AA38,39   FAARKKAAKALAPK   (SEQ ID NO: 39)

AKAP 79 AAA40-42  FKRAAAAAKALAPK   (SEQ ID NO: 40)

AKAP 79 4A38-42   FAAAAAAAKALAPK    SEQ ID NO: 41)

AKAP 79 AA45,50   FKRRKKAAAALAPA   (SEQ ID NO: 42)

AKAP 79 A37-50    FAAAAAAAAALAPA   (SEQ ID NO: 43)
```

Each mutant AKAP 79 fragment mutant is assayed for its ability to inhibit PKC by the method described above. The PKC βI protein is expressed in baculovirus and monoclonal antibodies M4 and M7 are used to detect PCK α and β isoforms by the following method.

Because preliminary data suggests that PKC and AKAP 79 associate in vitro, it should be possible to isolate the AKAP 79/PKC complex from cells if the same or similar binding occurs in vivo. In order to attempt to isolate PKC/AKAP 79 binary complex, or a PCK/AKAP 79/CaN ternary complex from bovine brain, two independent biochemical approaches are employed that previously were successful for isolating an in vivo AKAP 79/CaN complex. The techniques are briefly described below.

Initial studies involve immunoprecipitation of the APAK 79 homolog, AKAP 75, from bovine brain, using monoclonal antibody MC16 generated against AKAP 79. Co-purification of PKC in the immunoprecipitates is detected by Western blot with rabbit polyclonal antisera that recognizes the predominant brain PKC isoforms α βI, βIII, and γ. Alternatively, PKC is immunoprecipitated from bovine brain extracts with the monoclonal antibody M7 which recognizes the brain PKCα and β isoforms and co-purifying AKAP 75 is detected by RII overlay or Western blot. Finally, identical samples immunoprecipitated with anti-PKC antibodies are probed for CaN with monoclonal antibody C24 that recognizes the bovine CaN A subunit. These experiments may establish whether a ternary complex of APAK 79/PKC and CaN is formed.

Alternatively, affinity purification is performed in order to isolate a ternary complex of RII, AKAP 79 and PKC from bovine brain. The R subunit of PKA is purified by affinity chromatography on cAMP-agarose and the eluate screened for the presence of PKC and AKAP by Western blots with the M7 and MC16 monoclonal antibodies, respectively. Since recombinant AKAP 79 and PKC do not bind cAMP-agarose, detection of either protein in the cAMP eluate confirms the formation of a complex between both kinases and the anchoring protein. Confirmation of a ternary complex is achieved by elution of PKC and AKAP 79 from cAMP-agarose with excess anchoring inhibitor peptide. This peptide has previously ben shown to displace the AKAP/CaN complex from RII immobilized on cAMP-agarose.

EXAMPLE 12

Primary Screening Methods For Compounds Which Inhibit AKAP 79/RII Binding

The scintillation proximity assay (SPA) screening protocol described in Example 8 was employed to determine the ability of various chemicals to inhibit binding between AKAP 79 and $^3$H-RII. In two rounds of tests, approximately 31,000 chemicals were screened in pools of twenty-two chemicals per assay. Test chemicals assayed were not pre-selected based on any known properties and there was no overlap between chemicals in individual groups. In analysis of the results, a positive observation, or a "hit," was defined as a single chemical capable of inhibiting 50% AKAP 79/RII binding at a concentration of 50 μM or less. In the screening method, AKAP 79 was first captured in individual wells followed by sequential addition of the test chemical pool and labeled $^3$H-RII. Percent binding was determined by the measuring the amount of radioactivity in each well compared to the amount of radioactivity in wells wherein only AKAP 79 and $^3$H-RII were introduced.

Sixty-seven of the individual pools showed greater than 50% inhibition of AKAP 79/RII binding and, in order to determine which component in the pool was responsible for the observed inhibition, chemicals in each pool were subsequently assayed individually. At a concentration of 25 μM, twenty-one chemicals showed binding inhibition greater than or equal to 50%.

For each of the twenty-one chemicals, $IC_{50}$ values were determined by repeating the assay in the presence of increasing concentrations of each chemical. Fourteen of the twenty-one resulted in fifty percent inhibition at a concentration of 50 μM or less. A total of nine of the fourteen chemicals were selected for secondary screening as described below, the first three designated IC1062, IC4273, and IC4234.

EXAMPLE 13

Secondary Screening Methods

Secondary screening included a variety of assays to examine specificity and selectivity of identified inhibitory compounds, including: (1) an SPA based on a different capture method, streptavidin-capture of biotinylated AKAP 79, to determine if the test chemicals affected antibody capture rather than AKAP 79/RII binding; (2) an SPA using AKAP Ht31 to examine specificity of AKAP 79 binding inhibition; and (3) a slot blot assay to measure in vitro binding of $^{32}$P-RII to a variety of other AKAPs and specificity of inhibition by the compounds. In view of the observation that, in addition to RII, AKAP 79 binds PKC [Klauck, et al., Science 271:1589–1592 (1996)], CaN [Coghlan, et al., Science 267:108–111 (1995)], and RI (Example 7), chemicals which significantly inhibited AKAP 79/RII binding are also assayed for the ability to inhibit AKAP 79 binding to PKC, CaN, and RI. Each of the chemicals identified in Example 12 are used in assays to further characterize the inhibition of AKAP 79/RII binding. Various forms of AKAP 79, including full length and amino terminal truncations, are utilized in the screening techniques to determine the effect of the modified AKAP polypeptide.

Plasmid araCB was further modified by insertion of an alternative polylinker sequence (SEQ ID NO: 46) which added BglII and XhoI restriction sites. Two oligonucleotides were synthesized, a sense ara7 oligonucleotide and an anti-sense ara8 oligonucleotide (SEQ ID NOs: 47 and 48, respectively), annealed, digested with XbaI and HindIII, and subdloned into plasmid araCB previously digested with the same two enzymes. The resulting plasmid was designated araCB-1.

```
araCB-1 polylinker TCTAGACCATGGTCGACCTGCAGGCATGCAGATCTCTCGAGAAGCTT  SEQ ID NO: 46 ara7               5'-CTAGACCATGGTCGACCTGCAGGCATGCAGATCTCTCGAGA-3'   SEQ ID NO: 47 ara8               5'-AGCTTCTCGAGAGATCTGCATGCCTGCAGGTCGACCATGGT-3'   SEQ ID NO: 48
```

A. Expression of Biotinylated Proteins

A modified Pinpoint expression vector (Promega, Madison, Wis.) was constructed encoding a desired protein as a fusion product adjacent sequences encoding biotin transferase encoding sequences. When bacteria are transfected with this vector and grown in the presence of biotin, the expressed protein is endogenously biotinylated as a result of the biotin transferase tag. Various vectors were constructed for expression of AKAP 79, truncations thereof, AKAP Ht31 and CaN A.

1. AKAP 79 Vector Construction

The plasmid pUC19 was modified to include an arabinose promoter and to also include AKAP 79 encoding sequences. The arabinose promoter [Wilcox et al., Gene 34:123–128 (1985); Wilcox, et al., Gene 18:157–163 (1982)] and the araC gene were amplified by PCR from the arabinose operon BAD of Salmonella typhimurium as an EcoRI/XbaI fragment with the primers araC-2 (SEQ ID NO: 43) and arab-1 (SEQ ID NO: 44).

```
araC-2   TACAGAATTCTTATTCACATCCGGCCCTG       SEQ ID
                                             NO: 43 arab-1   TACATCTAGACTCCATCCAGAAAAACAGGTATGG  SEQ ID
                                             NO: 44
```

Primer araC-2 includes an EcoRI site (underlined) and a termination codon (italics) for the araC gene product. Primer arab-1 includes a putative ribosome binding domain (italics) and an XbaI restriction site (underlined). PCR with these primers produced a 1.2 kb fragment which was digested with EcoRI and XbaI and subcloned into pUC19 (New England Biolabs, Beverly, Mass.) previously digested with the same two enzymes. The resulting plasmid was designated araCB and contained a polylinker region (SEQ ID NO: 45) flanked at the 5' end with a XbaI restriction site (underlined) and at the 3' end with a HindIII site (italics).

A cDNA encoding AKAP 79 was inserted into plasmid araCB-1 to provide a plasmid designated araAKAP 79. A 1.3 kb NcoI/XhoI AKAP 79 encoding fragment from plasmid AKAP 79/ADH2 was subcloned into araCB-1 previously digested with the same two enzymes. Briefly, AKAP 79 was subcloned into a yeast shuttle vector ADH2/sk⁻ using a three-way ligation: a 360 bp NcoI/XbaI fragment encoding the amino terminus of AKAP 79, an approximately 1.0 kb XbaI/BamHI fragment encoding the carboxy terminus of AKAP 79, and plasmid ADH2/sk⁻ previously digested with NcoIBamHI. The resulting ligation product, designated plasmid ADH2/sk⁻AKAP 79 contained the alcohol dehydrogenase (ADH) promoter 5' to AKAP 79 encoding sequences. The resulting plasmid was then digested with SacI (SstI) and BamHI and the AKAP encoding sequence subcloned into the yeast expression vector yepC/ADH2 previously digested with the same two enzymes. The resulting plasmid araAKAP 79 served as template DNA for generating other AKAP 79 and AKAP 79 truncation expression plasmids discussed below.

2. Construction of a Biotin Expression Plasmid Plasmid araCB-1 was further modified to express a gene encoding biotin transferase as follows. Biotin transferase was amplified using PCR from a Pinpoint expression plasmid (Promega) as a XbaI/BglII fragment and inserted into araCB-1 previously digested with the same two enzymes. Two oligo primers were used to amplify the gene: sense primer BIOTIN 1b (SEQ ID NO: 49) included a XbaI site (underlined in the sequence presented below) and the initiating methionine codon for biotin transferase, and anti-sense primer BIOTIN 2 (SEQ ID NO: 50) encoded a factor Xa cleavage site (underlined, the complement of which encodes the amino acid sequence Ile-Glu-Gly-Arg, SEQ ID NO: 51) and added restriction sites recognized by enzymes NcoI (CCATGG), SphI (GCATGC), and BglII (AGATCT) to the amplification product for subcloning purposes.

```
araCB polylinker   TCTAGAGTCGACCTGCAGGCATGCAAGCTT   SEQ ID NO: 45
```

```
BIOTIN 1b 5'-TACATCTAGAATTATGAAACTGAAGGTAACAGTCAACGGC-3' SEQ ID NO: 49

BIOTIN 2  5'TACAAGATCTGCATGCCATGGTGCGACCTTCGATGAGCTCG3'    SEQ ID NO: 50
```

As template in the PCR amplification, 1 μl of a Pinpoint plasmid Xa-1 solution was diluted in 49 μl water to a final concentration of approximately 100 ng/50 μl. Primers (SEQ ID NOs: 49 and 50) were dissolved water to provide a 10× stock solution with a concentration of 100 μg/ml. The amplification reaction was carried out in a mixture containing 30 μl water, 5 μl 10× PCR buffer (0.5 M KCl, 50 mM Tris, pH 8.3, and 15 mM $MgCl^2$), 5 μl 2 mM dNTPs, 5 μl of each oligo primer solution, 1 μl template solution and 0.5 μl TAQ polymerase (Boehringer Mannheim Biochemicals, Bloomington, Ind.) in a 50 μl reaction overlaid with 100 μl of mineral oil. Amplification was carried out after an initial 4 minute incubation at 94° C., with 30 cycles of 94° C. for 1 minute, 60° C. for 2 minutes, and 72° C. for 4 minutes.

Following PCR, the amplification product was purified over a CL6B column, and 10 μl of the purified material digested with enzymes XbaI and BglII. The digestion reaction was loaded onto an 0.8% low melting point agarose (LMA) gel and a 400 bp fragment was isolated. The 400 bp fragment was ligated into araCB plasmid previously digested with XbaI and BglII and purified on a LMA gel. The resulting expression vector was transformed into XL-1 Blue cells (Stratagene, San Diego, Calif.) and transformants were selected on LB/agarose plates containing 100 μg/ml carbenicillin. Transformants were grown up in 2.0 ml of LB broth containing 100 μg/ml carbenicillin and plasmid DNA was isolated using Promega's (Madison, Wis.) Wizard miniprep kit according to the manufacturer's suggested protocol. Isolated plasmid DNA was digested with XbaI and NcoI to confirm the presence of a 400 bp band. Preparations containing the appropriate insert were sequenced and verified correct. One miniprep designated arabio 1b was selected and used to clone AKAP Ht31, AKAP 79, and various AKAP 79 truncations described below.

3. Preparation of Biotinylated-AKAP 79 Expression Plasmid

A full length cDNA encoding AKAP 79 was subcloned into arabio1b as follows. Plasmid araAKAP 79 was digested with NcoI and HindIII and the isolated AKAP 79 encoding fragment ligated into plasmid arabio1B previously digested with the same enzymes. The resulting AKAP 79-encoding plasmid was transformed into E.coli, the transformed bacteria grown in the presence of biotin, and the endogenously biotinylated AKAP 79 polypeptide isolated as described below.

4. Preparation of AKAP 79 Truncation Expression Plasmids a. AKAP 79/Met108

An expression plasmid was constructed which encoded an AKAP 79 truncation having the first 108 amino terminal residues deleted (designated AKAP 79/Met108) and the protein product expressed as a biotin transferase fusion polypeptide. Two primers, 79-MET 108 and ara2 (SEQ ID NOs: 51 and 52, respectively) were used in PCR to amplify the truncated version of AKAP 79 from araAKAP 79 template DNA.

```
79-MET 108       5'TACAACCATGGCAATAAATGCTGAGGC3'  SEQ ID NO: 51 ara2 (pUC19 RP)  5'CACAGGAAACAGCTATGACC3'         SEQ ID NO: 52
```

Primer 79-MET 108 was designed to encode a methionine residue immediately upstream from AKAP 79 amino acid 108 and to add an NcoI restriction site. Antisense primer ara2 was designed to introduce several unique 3' restriction sites, including XhoI, HindIII, and BamHI.

A standard PCR reaction was used to amplify the AKAP 79/Met108 truncation using the primers described above (SEQ ID NOs: 51 and 52). Template DNA was prepared by first diluting plasmid araAKAP79 1:50 (final concentration 100 ng/μl) in TE buffer containing 10 mM Tris, pH 8.0, and 0.1 mM EDTA. A 50 μl reaction mixture containing 5 μl 10× PCR buffer (described above), 5 μl 5 mM dNTPs, primers 79-Met108 and ara2 to a final concentrations of 100 μg/ml, 30 μl water, 1 μl template DNA, and 0.5 μl Taq polymerase (Boehringer Mannheim). The amplification reaction was carried out under the following conditions: incubation at 94° C. for 4 minutes, followed by 30 cycles of 94° C. for one minute, 60° C. for two minutes, and 72° C. for four minutes. The resulting amplification product was purified over a CL6B column and the purified product digested with NcoI and HindIII. The NcoI/HindIII fragment was purified on a 0.8% LMA gel and ligated into plasmid arabio1b previously digested with the same enzymes. Six transformants were grown for minipreps and plasmid DNA was isolated using a Promega Wizard kit. Plasmid DNA with the correct insert was identified by restriction analysis with NcoI and HindIII, and one preparation was chosen to transform arabinose-deleted E. coli strain E104E for production of the AKAP 79/Met108 truncation. The resulting plasmid was designated bioAK79Met108.

b. AKAP 79/Met159 and AKAP 79/Met247

Plasmids separately encoding two additional AKAP 79 truncation mutants, AKAP 79/Met159 and AKAP 79/Met247, wherein the first 159 or the first 247 amino terminal amino acids were deleted were constructed as follows.

DNAs encoding the two truncations were separately amplified by PCR using the anti-sense primer ara2 (SEQ ID NO: 52), used to amplify AKAP 79/Met108 truncation but in combination with 5' primer 79-MET159 (SEQ ID NO: 53) to amplify AKAP 79/Met159 or 5' primer 79-MET247 (SEQ ID NO: 54) to amplify AKAP 79/Met247.

```
79-MET159   5'TACAACCATGGCTGAAATTTTGGATATAC3'  SEQ ID NO: 53

79-MET247   5'TACAACCATGGCAAGCCCACTTGAAACTTC3' SEQ ID NO: 54
```

Primers 79-MET159 and 79-MET247 each introduced an NcoI restriction site and a methionine residue amino terminal to residues 159 and 247, respectively. (Underlining in both sequences indicates an initiating methionine codon, bold in SEQ ID NO: 53 indicates the codon for amino acid 159, and bold in SEQ ID NO: 54 indicates the codon for amino acid 247.) The resulting amplification products were purified as described above, digested with enzymes NcoI and HindIII, and ligated into arabio1b previously digested with the same two enzymes. The resulting plasmids were designated bioAK79Met159 and bioAK79Met247, respectively.

5. Preparation of AKAP Ht31 Expression Plasmid

Vector pET11d (Novagen, Madison, Wis.) was modified to encode AKAP Ht31 and transformed into XL-1 Blue cells by the method previously described [Softko-Hahn, et al., FEBS Letters 301:274–278 (1992)]. Briefly, approximately 10 ng plasmid pET11d was transformed into 100 μl CaCl$_2$-prepared competent bacterial cells previously incubated on ice for 30 minutes. The cells mixed with the plasmid were heat shocked for 2 minutes at 42° C. and plated on agarose. Blue/white selection was used to identify positive clones.

Plasmid DNA from positive clones was isolated using Promega's Wizard Miniprep kit according to manufacturer's suggested protocol and was digested with NcoI and HindIII. The resulting fragments were separated on a 0.8% LMA gel from which a 1.4 kb fragment was isolated and cloned into plasmid arabio1b previously digested with NcoI and HindIII. The resulting plasmid encoding AKAP Ht31 as a fusion protein with biotin transferase was designated bioHT31.

6. Construction of a Biotinylated-CaN A Expression Plasmid a. Preparation of Vector arabio-Spe #2

Because of difficulties associated with subcloning a CaN A encoding DNA into plasmid arabio1b by the methods utilized above for AKAP 79 and its truncations, (CaN A DNA includes an internal NcoI restriction site) it was necessary to further modify plasmid arabio1b to allow subcloning with requiring NcoI digestion. As an alternative to NcoI, an SpeI site was introduced into the arabio1b polylinker region as follows.

The gene encoding biotin transferase was amplified from plasmid arabio1b by PCR as an XbaI/BglII fragment with primers ara1 (SEQ ID NO: 55) and biotin speI (SEQ ID NO: 56).

Primer ara1 corresponded to a region 5' to the unique XbaI site and the initiating methionine codon for biotin transferase, while primer biotin-speI, encoding the 3' region of biotin transferase and the factor Xa cleavage site, generated a new SpeI restriction site (underlined above). The resulting fragment was subcloned into plasmid araCB as an XbaI/BglII fragment and the new plasmid designated arabio-Spe #2.

b. Construction of a CaN A Expression Vector

A rat cDNA encoding CaN A was PCR amplified from vector RAT CaN-A/pVL21392 (Vollum Institute, Portland Oreg.) with primers CaN A-sense and CaN A-antisense (SEQ ID NO: 57 and 58, respectively).

```
CaN A-sense     5'-ACAACTAGTATGTCCGAGCCCAAGGCGATTGATCCC-3'      (SEQ ID NO: 57)

CaN A-antisense 5'-ATGTAGATCTTCACTGAATATTGCTGCTATTACTGCCGTTGCT-3' (SEQ ID NO: 58)
```

The resulting 1.6 kb amplification product included a unique SpeI restriction site 5' to the initiating methionine codon, and a unique BglII site adjacent the termination codon. The amplified fragment was digested with SpeI/BglII and subcloned into plasmid arabio-Spe #2 previously digested with the same two enzymes. The resulting plasmid was designated bioCaN-A #3.

The CaN A encoding plasmid was transfected into E. coli and clones bearing plasmids with the correct insert were selected for expression of a 69 kD biotin-calcineurin recombinant protein. Proper plasmid construction was further confirmed by the presence of the approximately 1.6 kb insert following digesting with SpeI and BglII. A single positive clone, designated bioCaN-A #3 was used for further CaN A expression.

B. Alternative Capture Method

In a first screening method, the ability of the chemicals identified in Example 12 to inhibit $^3$H-RII binding to AKAP 79 was tested using a different capture method. Scintillation proximity assays (SPA) were performed as described above in Example 8 except that AKAP 79 was first biotinylated and immobilized in wells precoated with streptavidin. Immobilizing AKAP 79 by this method eliminated the possibility that the test chemical might release immobilized AKAP 79 from the well by interfering with its binding to the anti-TRX antibody.

The soluble fraction from a centrifuged cell lysate containing biotinylated AKAP 79/Met108 was used for capture on a ScintiStrip plate precoated with streptavidin (Wallac, Turbu, Finland) and the assay continued as described in Example 8.

Results indicated that each of the three chemicals inhibited $^3$H-RII binding to biotinylated AKAP 79/Met108 as effectively as it inhibited TRX-AKAP 79/$^3$H-RII binding.

```
ara1        5'-GCGACTCTCTACTGTTTCTC-3'                      (SEQ ID NO: 55)

biotin-speI 5'-TACAAGATCTGCATGCCTGCAGGTCGAC-
               ACTAGTGCGTACCTTCGATGAGCTCGAGACTAAGG-3'       (SEQ ID NO: 56)
```

C. Specificity of AKAP 79/RII Binding Interaction

In another screening assay, each chemical was tested for its ability to specifically inhibit AKAP 79/RII binding in vitro by comparing inhibition to that in a parallel control assay wherein the immobilized anchoring protein was AKAP Ht31. The Ht31/$^3$H-RII binding assay was performed exactly as described for the AKAP 79/Met108-$^3$H-RII assay. Biotinylated Ht31 protein was produced in vivo after subcloning Ht31 encoding DNA into the modified pinpoint vector (described above), the vector transfected into E. Coli, and the bacteria grown in the presence of biotin. As with AKAP 79, biotinylated Ht31 was captured on plates precoated with streptavidin, and $^3$H-RII showed specific and saturable binding to each of the immobilized proteins.

All three inhibitors of AKAP 79/RII interaction failed to inhibit the binding of $^3$H-RII to biotinylated AKAP Ht31, suggesting that the inhibitors are selective in their inhibition of AKAP 79 and RII interaction.

D. Inhibition of RII Binding To Other AKAPs

In addition to testing the effect of the chemicals on AKAP Ht31/RII binding in an SPA format, the effect of the chemicals on the in vitro binding of $^{32}$P-RII to other AKAPs is examined using various AKAPs in a slot blot assay [Hauskin, et al., *J. Biol. Chem.* 269:24245–24251 (1994)]. The AKAPs include AKAP 95 [Coghlan, et al., *J. Biol. Chem.* 269:7658–7665 (1994)], AKAP 100 [McCartney, et al., *J. Biol. Chem.* 270:9327–9333 (1995)], and AKAP 220 [Lester, et al., *J. Biol. Chem.* 271:9460–9465 (1996)].

E. Inhibition of AKAP 79/PKC Binding

In a fourth screening method, each of the chemicals is assayed for its ability to inhibit binding between PKC and AKAP 79 in a PKC overlay assay described in Klauck et al., *Science* 271:1589–1592 (1996). Since AKAP 79 has been shown to complex with PKC and CaN [Coghlan, supra, and Examples 5 wand 11] in addition to RII of cAMP-dependent protein kinase, it is important to examine the effect the identified chemicals have on the interaction between AKAP 79 and PKC.

F. Inhibition of CaN/AKAP 79 Binding

In a fifth screening method, each of the chemicals is examined in vitro binding assays to detect inhibition of AKAP 79 and CaN binding in a method as described in Example 15 below and Coghlan, V. et al [*Science* 267:108–111 (1995)].

G. Inhibition of RI/AKAP 79 Binding

In a sixth screening method, each of the chemicals is examined in assays to determine the ability to inhibit AKAP 79/RI binding. The binding assay of RI and AKAP 79 is similar to that of CaN/AKAP 79 described below. Preliminary analyses indicate that RI can be passively captured on Immunlon plates and still maintain the ability to bind biotinylated AKAP 79 as described below in Example 15.

EXAMPLE 14

Tertiary Screening Methods

Tertiary screening on the chemicals identified above included (1) cellular toxicity assays; (2) in vitro enzyme inhibition assays using CaN, PKA, or PKC; and (3) functional assays to assess in vivo inhibition of RII localization and modulation of cytokine expression. Each of the screening techniques is separately discussed below.

A. Toxicity Assays

In order to provide an initial assessment of the toxicity of compounds IC1062, IC4273, and IC4234, 200 μl containing $10^5$ Jurkat 77 cells were plated into wells of a 96 well Corning flat bottom plate containing one of the anchoring protein modulating drugs at different concentrations. Appropriate solvent controls were set up for each drug, and incubation was at 37° C. in 5% $CO_2$.

On each day of the assay, 100 μl of cells were removed from each well and added to a new plate for assaying toxicity. A hundred microliters of fresh media containing drug or solvent were added to the original plate, which was returned to the incubator. Toxicity assays were performed using Promega's MTS based toxicity assay kit according to manufacturer's instructions.

Compound IC4273 was tested at 50, 10 and 5 μM. By day 1, cell viability was reduced by 70% at 50 μl. No toxicity was observed at the other tested concentrations. By day 2, all cells were dead at 50 μM. Cell viability was reduced by 20% at 10 μM and no toxicity observed at 5 μM. By day 3, the last day of assay, all cells were dead at 10 μM and cell viability reduced by 10% at 5 μM.

Compound IC1062 was tested at 50, 10 and 5 μM. By day 1, cell viability was reduced by 70–75% at all concentrations. By day 2, all cells were dead at all tested concentrations. The toxicity of this drug was not attributable to the drug solvent.

B. Enzyme Inhibition Assays

1. CaN Inhibition

The activity of CaN is measured by the $Ca^{2+}$—and calmodulin-dependent release of $^{32}P_i$ from $^{32}$P-inhibitor 1, using the method of Nairn, et al. [*Neuroprotocols* 6:108–111 (1995)]. Identified chemicals are pre-incubated with 4 or 30 nM CaN before initiation of the reaction with $^{32}$P-inhibitor 1 (Chemicon). Inhibitor 1 (50 μg) was phosphorylated using the catalytic subunit of PKA and purified according to the procedure described in Nairn, et al., [supra]. Phosphatase activity in the absence of chemicals is defined as 100%.

2. PKA Inhibition

In order to assess the ability of compounds IC4273, IC4234, and IC1062 to modulate PKA activity in vitro, each compound was tested at 10 μM to determine its affect on the ability of recombinant PKA catalytic subunit to phosphorylate the PKA substrate Kemptide (Sigma).

Kinase reactions were carried out plus or minus 10 μM each chemical in 100 mM HEPES, pH 7.4, containing 33 μM Kemptide, 15 ng recombinant PKA catalytic (rC) subunit, 100 μM ATP, 4 μCiγ$^{32}$PATP, 150 mM NaCl, 12 mM $MgCl_2$. Reactions were incubated at 30° C. for 10 minutes, stopped by addition of 50% acetic acid, and spotted onto phosphocellulose P81 paper. The paper was allowed to air dry and washed four times (5 minutes each) at room temperature in 150 mM phosphoric acid. The paper was allowed to air dry and Cerenkov counted.

Results indicated that none of the three chemicals had an effect on PKA ability to phosphorylate the exogenous substrate Kemptide.

3. PKC Inhibition

In order to assess the ability of compounds IC4273, IC4234, and IC1062 to modulate PKC activity in vitro, each compound was tested at 10 μM in a PKC enzyme assay kit (Amersham) to determine the effect of each compound on the PKC activity. PKC was previously purified from rat brain by the method of Woodgett, et al., *J. Biol. Chem.* 262:4836–4843 (1987). Assays were performed according to manufacturer's suggested protocol with or without 10 μM of each of the assay chemicals. The reaction was terminated with the stop reagent, and a reaction aliquot spotted onto phosphocellulose P81 paper. The paper was air dried and washed four times for five minutes each wash at room temperature in 150 mM phosphoric acid. The paper was allowed to air dry again and Cerenkov counted.

Results indicated that none of the chemicals had an effect on the ability of PKC to phosphorylate the peptide provided in the kit.

C. Functional Assays

1. Inhibition of RII Localization

The inhibitory chemicals identified in the AKAP/RII screening assays (IC4273, IC4234 and IC1062) were tested in a human T-cell functional assay for their effects on induced interleukin-2 (IL-2) transcription. Initial assays were completed using the human T-cell line Jurkat-77 that had been stably transfected with the NFATZH construct (Fred Hutchinson Cancer Research Center, Seattle, Wash.) containing three tandem copies of the NFAT binding site from the IL-2 promoter to direct transcription of the lacZ gene. Hygromycin resistant clones were maintained in complete RPMI 1640 media (Gibco, Grand Island, N.Y.) supplemented with 10% (v/v) fetal bovine serum and periodically cycled in this media with 300 μg/ml hygromycin B (Boehringer Mannheim, Indianapolis, Ind.).

Jurkat-77-NFATZH cells were suspended at $10^6$ cells in 1 ml of RPMI complete with or without compounds IC4273, IC4234 or IC1062 at 10, 5 or 1 μM. Cells were incubated for 1 hour at 37° C. Control samples were incubated with 25 μM forskolin (Sigma St Louis, Mo.) and 0.1 mM isobutyl-1-methyl xanthine (IBMX, Sigma) for 30 minutes at 37° C. Cells were activated for 4 hours at 37° C. with 10 ng/ml PMA (Sigma) and a calcium ionophore A23187 (400 ng/ml, Sigma), and washed in PBS and lysed in 20 μl 250 mM Tris, pH 7.8. Samples were vortexed, subjected to five freeze-thaw cycles, and centrifuged at 14000 rpm in a Beckman GS-6R rotor for 15 minutes at 4° C. Supernatants were assayed by β-gal activity according to methods described by Hollon and Yoshimura [*Anal. Biochem.* 182:411–418 (1989)].

Briefly, 20 μl cell lysate was transferred to a 96 well Immulon-4 assay plate (Dynatech Laboratories, Inc., Chantilly, Va.) and 70 μl of Z buffer (0.06 M $Na_2HPO_4.7H_2O$, 0.04 M $NaH_2PO_4.H_2O$, 0.01 M KCL, 1 mM β-mercaptoethannol, pH 7.0) plus 10 μl 50 mM chlorophenol red β-D-galactopyranoside (CPRG), (Boehringer Mannheim) was added. Following incubation for 30 to 60 minutes at 37° C. to permit color development, the plates were read on a Dynatech MR500 at 570 nm. Data from several experiments were pooled after normalizing to PMA and A23187 induced control.

Results indicated that PMA and A23187 induced β-gal expression from 10 to 100 fold over uninduced control cells, however, the signal was blocked by 66% with forskolin and IBMX. Pretreatment with IC4273 at 10 μM and 5 μM resulted in β-gal expression enhanced by 63% and 65%, respectively, but no effect was observed with IC4273 at 1 μM. When IC4273 was introduced at the above mentioned doses either before or after introduction of forskolin and IBMX, no effect was observed on the forskolin and IBMX inhibition of induced β-gal.

IC4234 and IC1062 both blocked the induction of β-gal when assayed at 10 μM (57 and 93%, respectively) and 5 μM (46 and 64%). Only IC1062 blocked at 1 μM by 44%.

2. Cytokine Induction

Compounds IC4273, IC4234, and IC1062 were assayed for their ability to modulate induction of cytokines IL-2, IL-4, IL-10 and INFγ in normal human peripheral blood mononuclear cells (PBMC). Briefly, PBMC were isolated from heparinized peripheral blood from adult volunteers. Blood was diluted 1:1 with calcium/magnesium free phosphate buffered saline (CMF-PBS) and centrifuged over Histopaque (Sigma) at a density of 1.095 g.cm$^{-3}$ for 30 minutes at 400×g. Cells at the interface were collected, washed in CMF-PBS, and resuspended in RPMI complete media. Cells were transferred to a 96 well round bottom tissue culture plate (CoStar Corporation, Cambridge, Mass.) at a density of $5 \times 10^5$ cells/well in 200 μl RPMI complete media, with or without the above mentioned compounds at 5 μM, and incubated for 1 hour at 37° C. Control assays were conducted with cells incubated with 25 μM forskolin and 0.1 mM IBMX for 30 minutes or with 50 ng/ml cyclosporin A for 10 minutes at 37° C. Following each incubation, an additional 50 μl RPMI complete was added to each well, with or without phytohemagglutinin (PRA) (Sigma) at a final concentration of 5 μg/ml and the cells incubated overnight at 37° C. The following day, culture supernatants were assayed for cytokine release using a Cytoscreen Immunoassay Kit (BioSource International, Camarillo, Calif.) according to manufacture's instructions.

PHA elevated expression of cytokines IL-2, IL-4, IL-10 and INFγ 24 hours after treatment, while cyclosporin A and forskolin with IBMX inhibited induction of all four cytokines. The effects of pretreatment with the compounds IC4273, IC4234, and IC1062 were variable, but the strongest effects were observed on INFγ secretion. IC4273 enhanced INFγ induction by 165%, while IC4234 and IC1062 blocked induction by 93% and 78%, respectively. IC4234 and IC1062 also strongly inhibited IL-2, IL-4 and IL-10 induction, while IC4273 modestly induced IL-2 and IL-4 secretion by 22% and 14%, respectively. The effect of IC4273 on IL-10 induction was inconclusive.

EXAMPLE 15

Specificity of AKAP 79 Binding To Calcineurin

AKAP 79 binding to calcineurin has been demonstrated both in the yeast two di-hybrid system and in co-purification techniques using rat brain extract [Coughlin, et al., *Science* 267:108–111 (1995)]. See Examples 1 through 4. In order to confirm the specificity of the interaction between AKAP 79 and calcineurin, a number of different, but complimentary, approaches were employed.

A. Co-immunoprecipitation

In a first technique, interaction between recombinant AKAP 79 and the catalytic A subunit of CaN, CaN A, (in the absence of the regulatory B subunit, CaN B) was demonstrated with co-immunoprecipitation.

AKAP 79 was expressed either as a full length TRX fusion protein in *E. coli* as described above in Example 8, or as a truncated biotinylated fusion protein in the modified pinpoint system as described in Example 13. Three truncated variations were expressed with either 108 amino terminal residues deleted (AKAP 79/Met108), 159 amino terminal residues deleted (AKAP 79/Met159), or 247 amino terminal residues deleted (AKAP 79/Met247).

Rat brain CaN A (α form) was expressed in Sf9 cells using a baculovirus expression system according to the method of Perrino, et al. [*J. Biol. Chem.* 267:15965–15969 (1992)]. The CaN A expression construct was obtained from Vollum Institute, (Portland, Oreg.). When CaN A and CaN B were coexpressed in Sf9 cells, CaN phosphatase activity was detected, suggesting that the recombinant CaNA is catalytically active in the presence of the regulatory CaN B subunit.

In co-immunoprecipitation experiments, recombinant CaN A was incubated for 1 hour in the presence or absence of full length TRX-AKAP 79 (see Example 8) in a buffer containing 5% milk and 0.2% Tween 20. Polyclonal sera to AKAP 79 was added and after further incubation, antibody-antigen complexes were precipitated with Protein A Sepharose beads (Sigma, St. Louis). Nonspecific proteins were removed from the beads with repeated washing in buffer containing 10 mM HEPES, 150 mM NaCl, 1% Triton X-100. Specific proteins were removed from the beads, using stop solution containing SDS, separated by SDS/PAGE, and transferred to nitrocellulose.

An overlay assay with biotinylated calmodulin (Bio-CaM) was used to detect the presence of CaN A on the nitrocellulose filter. The filter was incubated with Bio-CaM according to a method previously described [Billingsley, et al., *Meth. Enzymol.* 184:451–467 (1990)] except that Bio-CaM was detected using streptavidin-HRP (Pierce, Rockford, Ill.). Briefly, protein separated using SDS-PAGE was transferred by standard techniques to nitrocellulose filters. The filters were blocked for one hour at room temperature in buffer containing 10 mM Tris, 150 mM NaCl and 10% non-fat dry milk. The blot was further incubated with 0.5 μg/ml biotinylated calmodulin (Veritas, Potomac, Md.) in buffer containing 10% non-fat dry milk and 0.2 mM $CaCl_2$. After incubation for thirty minutes, unbound calmodulin was removed with washing first with TBS containing 0.2 mM $CaCl_2$, followed by washing with TBS containing 0.2 mM $CaCl_2$, and finally with TBS containing 0.2 mM $CaCl_2$ and 0.05% Tween 20. After washing, the blot was incubated with a 1:4000 dilution of streptavidin-HRP (Pierce, Rockford, Ill.) in 100 mM Tris, pH 8.5, 0.2 M NaCl, 0.2 mM $CaCl_2$ and 0.05% Tween 20. Unbound streptavidin was removed with washing as described above. An enhanced chemiluminescence (ECL) kit (Amersham, Arlington Heights, Ill.) was used to detect binding between biotinylated protein and streptavidin-HRP complex on the nitrocellulose.

Results indicated that Bio-CaM bound predominately to CaN A, and that binding of Bio-CaM to full length AKAP 79 was insignificant compared to the binding of Bio-CaM to CaN A. In the absence of AKAP 79, CaN A was not immunoprecipitated by polyclonal sera to AKAP 79. However, when CaN A was incubated with AKAP 79, polyclonal sera to AKAP 79 precipitated CaN A and AKAP 79 as a complex, as detected by Bio-CaM binding to the complex in the overlay assay described above. Since no CaN B subunit was present, these results were consistent with previous observations from yeast dihybrid screening which indicated that the interaction between AKAP 79 and CaN A can be detected in the absence of the regulatory CaN B subunit.

B. ELISA and Modified ELISA

In a second examination of AKAP 79/CaN A interaction, in vitro binding of AKAP 79 to immobilized CaN A was demonstrated using ELISA or a specific modification thereof. Two different capture methods were used. In one method, CaN A was first captured on plates by passive coating, AKAP 79 or biotinylated AKAP 79 was added, and complex formation detected by either ELISA or by streptavidin-HRP. In another method, rabbit anti-mouse antibodies were first captured on plates, mouse anti-TRX antibodies added and captured, and TRX-AKAP 79 added and captured. This method was similar to the capture method used for AKAP 79/$^3$H-RII SPA. Biotinylated CaN A was then added, and the complex detected by streptavidin-HRP.

Specifically, in the first method, recombinant CaN A, expressed as described above, was added to wells of Immulon plates (Dynatech) in a 35 mM sodium bicarbonate/15 mM sodium carbonate buffer, pH 9.6. Proteins bound to the surface of the wells by plastic/protein interaction. As a positive control, RII, and a negative control, bovine serum albumin (BSA) were separately and similarly captured in individual wells and assayed in this method. Nonspecific sites in the wells were blocked with a buffer containing 2.5% milk in 50 mM sodium citrate and 145 mM sodium chloride. Full length TRX-AKAP 79 was added in a final volume of 100 μl and after up to 2 hours incubation, free and non-specific proteins were removed with several washes with PBS/0.5% Tween 20. A mouse anti-AKAP 79 monoclonal antibody, generated against recombinant AKAP 79, was added to each well, followed by addition of a horse radish peroxidase (HRP)-conjugated goat anti-mouse antibody. HRP substrate tetramethylbenzidine (TMB) was added and absorbance at 450 nm determined using a Dynatech 96 well plate reader.

In the modified ELISA, standard ELISA techniques were employed except that HRP-conjugated streptavidin was used to detect bound biotinylated AKAP 79 instead of an anti-AKAP 79 monoclonal antibody. Briefly, after incubation of immobilized CaN A with biotinylated AKAP 79, HRP-conjugated streptavidin was added for 30 minutes. Unbound protein was removed with multiple washes of PBS/0.05% Tween 20. Bound streptavidin was detected with HRP substrate TMB and absorbance measured at 450 nm using a Dynatech 96 well plate reader. As in the ELISA described above, RII was immobilized and assayed as a positive control, and BSA as a negative control.

Both ELISA methods demonstrated that full length AKAP 79 bound to immobilized CaN A, but not to immobilized control protein bovine serum albumin (BSA). In addition, truncation AKAP 79/M108 showed saturable binding to CaN A with a $k_d$ estimated between 20–200 nM. Truncations AKAP 79/Met159 and AKAP 79/Met247 showed no specific binding to CanA, but immobilized RII was specifically recognized by AKAP 79/M108, AKAP 79/M159, and AKAP 79/Met247. Wells coated with BSA had negligible binding. The results were the same whether a soluble fraction of bacterial lysate expressing the specific construct was used or if a purified biotinylated AKAP 79 was used. These results suggested that the amino terminal 108 residues of AKAP 79 are not essential for CaN A binding, but that residues between amino acid 109 and amino acid 159 do participate in CaN A binding.

In order to more precisely characterize the site of AKAP 79 binding on CaN A, a putative AKAP 79 binding site in CaN A is deleted and the deletion mutant form of CaN A is used in the assays described above in place of full length CaN A. A properly chosen CaN A deletion mutant is expected to lose its ability to bind AKAP 79, but still be catalytically active when combined with the CaN B regulatory subunit.

C. AKAP 79/Biotinylated CaN A Binding

In another assay, captured AKAP 79 was used to bind biotinylated CaN A. CaN A was biotinylated endogenously after being subcloned by PCR into the modified Pinpoint vector, described above in Example 13. When bacteria grown in the presence of biotin are transfected with the bioCaN-A #3 construct, the expressed protein is endogenously biotinylated and can be purified to homogeneity using a soft-link avidin agarose purification kit (Promega, Madison, Wis.).

In order to examine the interaction of biotinylated CaN A with AKAP 79, a TRX-AKAP 79/mouse anti-TRX antibody complex was first captured onto plates pre-coated with anti-mouse antibody as previously described. Saturation binding was examined by adding biotinylated CaN A in PBS/0.2% BSA over a concentration range of 0 to 2 μM. Incubation was permitted for 1 to 2 hours after which non-specifically bound proteins were removed with repeated washes with PBS/0.05% Tween 20. Specific complex formation was detected with streptavidin-HRP as described in the modified ELISA above.

To increase the sensitivity and the range of signal detection, time-resolved fluorometry, DELFIA® (Wallac, Finland), was used. The technology is based on the use of lanthanide chelate labels with unique fluorescence properties. In this instance, streptavidin-europium diluted 1:1000 in assay buffer (Wallac) was employed to detect biotinylated CaN A/AKAP 79 complexes. After washing with PBS/0.05% Tween 20 to remove non-specifically bound proteins, Enhancement Solution (Wallac) diluted 1:1 in water was added and release of europium measured by increased fluorescence using a DELFIA® Research Fluorometer (Model 1232, Wallac). With this system, a signal to noise ratio of 8–10:1 was generally obtained.

Both methods of detection showed that biotinylated CaN A bound to TRX-AKAP 79 with a $k_{d\ of\ approximately}$ 90 to 120 nM. Negligible binding was detected in wells wherein TRX alone was captured.

EXAMPLE 16

AKAP 79 Binding Site on CaN A 11.1

A. Yeast Di-Hybrid Analysis

Previous mutational studies have indicated that two distinct regions on calcineurin A (CaN A) are necessary for AKAP 79 binding and that calcineurin B is not required for CaN A/AKAP 79 interaction. An amino terminal region between residues 30 and 99 in CaN A was shown to be necessary for AKAP 79 binding, along with a carboxy terminal region located at amino acid 336. Three point mutants in which wild type calcineurin A was mutated at $Cys^{335}$, $Ser^{336}$ and $Pro^{339}$ did not effect binding.

In order to more precisely identify the carboxy terminal region required for AKAP 79 binding, alanine scanning mutants were constructed as described below and analyzed using the dihybrid assay as described in Example 4. In this method, a region of interest in a protein is chosen, and a mutant is constructed wherein three consecutive amino acids in the chosen region are substituted to alanine. A single mutant is constructed for every three consecutive amino acids across the region of interest and changes in wild type protein activity are assessed for each mutant. To more precisely define the CaN A region required for AKAP 79 binding, mutants were designed to scan a region from amino acid 311 to 334 in CaN A.

Scanning alanine mutants were constructed by ligating calcineurin clone 11.1 into the XhoI site of pBlue Script SK + (Stratagene). Using this parent clone, a series of eight (MH138-MH145) mutants were generated using Kunkel mutagenesis [Kunkel, Proc.Natl.Acad.Sci. (USA). 82:488 (1985) and Kunkel et al, Methods in Enzymology 54:367 (1987)]. Oligonucleotides synthesized and used to each of the eight mutants are set out in Table 2.

TABLE 2

Oligonucleotides to Generate Alanine Mutants

| MUTANT | OLIGONUCLEOTIDE | SEQ ID NO |
|---|---|---|
| MH138 | 5'GCTTTATTATTGTAAGCAGCAGC-GTAATTAGGTGCCG3' | 59 |
| MH139 | 5'GTACAGCAGCTTTAGCAGCAGCGA-CATCTAAGTAATTAGG3' | 60 |
| MH140 | 5'CATACTTTAGTACAGCAGCAGCA-TTATTGTAGACATCTAAG3' | 61 |
| MH141 | 5'CACATTATTTTCATAAGCAGCAGC-AGCAGCTTTATTATTGTAGAC3' | 62 |
| MH142 | 5'CGAATGTTCATCACATTAGCAG-CAGCCTTTAGTACAGCAGC3' | 63 |
| MH143 | 5'GCAATTAAACTGTCGAATGTTA-GCAGCAGCATTTTCATACTTTAG3' | 64 |
| MH144 | 5'GGAGAGCAATTAAACTGAGCAG-CAGCCATCACATTATTTTCATAC3' | 65 |
| MH145 | 5'GGATGTGGAGAGCAAGCAG-CAGCTCGAATGTTCATC3' | 66 |

Mutants were identified by sequence analysis and subcloned into the XhoI site of the "prey" plasmid, pACT, of the dihybrid system. These mutants were transformed into y190a pAS1 AKAP 79 and y153b pAS1 AKAP 79 as described in Example 4 and β-galactosidase filter assays were performed as described in Example 4.

Of the eight mutants, two were still able to interact with AKAP 79, mutant MH138 ($Leu^{311}$, $Asp^{312}$, $Val^{313}$→Ala, Ala, Ala) and mutant MH139 ($Tyr^{314}$, $Asn^{315}$, $Asn^{316}$→Ala, Ala, Ala) indicating these residues are not critical for AKAP 79 binding. Mutants MH140 ($Lys^{317}$, $Ala^{318}$, $Ala^{319}$→Ala, Ala, Ala) and MH142 ($Tyr^{323}$, $Glu^{324}$, $Asn^{325}$→Ala, Ala, Ala demonstrated a diminished ability to interact. With the remaining four mutants MH141 ($Val^{320}$, $Leu^{321}$, $Lys^{322}$→Ala, Ala, Ala), MH143 ($Asn^{326}$, $Val^{327}$, $Met^{328}$→Ala, Ala, Ala), MH144 ($Asn^{329}$, $Ile^{330}$, $Arg^{331}$→Ala, Ala, Ala) and MH145 ($Gln^{332}$, $Phe^{333}$, $Asn^{334}$→Ala, Ala, Ala) binding was abolished indicating these residues are required for the calcineurin/AKAP 79 interaction. All mutants gave identical results in both the $CNB^+$ strain (y190a) and the $CNB^-$ strain (y153b).

Results from this analysis demonstrated that amino acids 320–332 and 326–334 are necessary for AKAP 79 binding and this AKAP 79 binding domain is dissimilar to that of the FK506/FKBP binding domain [Griffith, et al, Cell, 82:507–522 (1995) and Villafranca, et al, Nature 378:641–644 (1995)].

B. AKAP 79/CaN A Mutant Binding

In order to confirm results from the yeast dihybrid screening, one of the CaN A mutants was assayed for an ability to bind AKAP 79. In the yeast dihybrid studies described above, the binding of AKAP 79 to mouse CaN A mutant MH144 ($Asn^{329}$, $Ile^{330}$, $Arg^{331}$→Ala, Ala, Ala) was abolished. Since a high throughput screening assay was developed exploiting direct protein binding between AKAP 79 and wild type rat brain CaN A, and because of previous problems expressing mouse CaN A clone 11.1 protein in *E. Coli*, an equivalent mutation in a rat brain CaN A was generated wherein amino acids $Asn^{330}$, $Ile^{331}$, $Arg^{332}$ were each changed to alanine. The mutant was designated CaN A/NIR and the recombinant protein was expressed as a biotinylated derivative. Purified biotinylated rat CaN A/NIR was used in the AKAP 79 binding assay in place of the wild type rat biotinylated CaN A to determine if its binding to AKAP 79 was abolished as observed in di-hybrid assays using mouse CaN A MH144.

To generate the rat brain CaN A/NIR mutant, amino acids 330 through 332 in rat brain CaN A were each changed to alanine using PCR-assisted site directed mutagenesis of the rat brain CaN A gene, (Vollum Institute, Portland, Oreg.). The gene was removed from vector pVL1393 (Invitrogen) as a BamHI/EcoRI fragment and subdloned into pFAST-BAC vector (Gibco/BRL) previously digested with BamHI and StuI. The resulting expression construct was used in all subsequent manipulations.

The method for PCR-assisted site directed mutagenesis of the gene followed the protocol outlined by Hu et al. [*Gene* 77:51–59 (1989)]. Two DNA fragments were initially generated having overlapping nucleotide sequences in common, the common overlapping region containing a desired mutated sequence. The two DNA fragments were synthesized in separate PCRs using specific combinations of constant outer oligos and internal mutagenic oligos.

Example 15. Protein from *E. Coli* expressing either the wild type or the CaN A/NIR mutant was purified using Soft-Link agarose (Promega, Madison, Wis.) or Calmodulin-Sepharose (Sigma), after which the purified protein was separated on SDS/PAGE. Coomassie blue staining showed that both protein migrated at a molecular weight of approximately 68 kD. The separated proteins were transferred to nitrocellulose and an immunoblot analysis was carried out using a polyclonal to CaN A (Chemicon, Temecula, Calif.). Immunoreactive proteins in the immunoblot confirmed the 68 kD molecular weight for each protein. When the nitrocellulose was incubated with Streptavidin-HRP (1:4000, Pierce, Rockford, Ill.) to detect biotinylated proteins, and the signal developed with an ECL kit (Amersham, Arlington Heights, Ill.), proteins of the same molecular weight were detected.

In AKAP 79 binding studies using wild type biotinylated CaN A as ligand, specific and saturable binding to TRX-AKAP 79 was observed (see Example 15). Nonspecific binding was defined as binding of the biotinylated CaN A to plates captured with lysates from *E. coli* expressing a control expression vector which did not encode AKAP 79. When biotinylated CaN A/NIR mutant was used as a ligand, one preparation showed no specific AKAP 79 binding, while a second preparation showed 50–80% reduction in specific binding compared to wild type CaN A. The results were therefore consistent with those obtained from the yeast di-hybrid studies, suggesting that the mutated amino acid sequence (amino acids 330 through 332) on CaN A is critical for binding to AKAP 79.

```
96-48
5' CONSTANT        AGG ACG CAG GGT ACC GCA TGT ACA GGA AAA GCC   SEQ ID NO: 69

96-49
3' CONSTANT        CTC CGC TGG GGA GCA TGC CAG TCG GGG TCA       SEQ ID NO: 70

96-50
MUTAGENIC PRIMER GAA CTG CGC GGC GGC CAT CAC CTT GTT CTC GTA    SEQ ID NO: 71

96-51
MUTAGENIC PRIMER CGT GAT GGC CGC CGC GCA GTT CAA CTG CTC C      SEQ ID NO: 72
```

The constant outer primers span an area of CaN A DNA containing unique KpnI and SphI restriction sites; digestion of the rat CaN A gene with these enzymes creates a fragment of approximately 430 base pairs. The internal mutagenic oligos contain the nucleotide sequence that creates the mutation and the overlap. After the overlapping fragments were synthesized, a third DNA fragment was amplified spanning the KpnI and SphI sites and containing the mutated nucleotide sequence. PCR to amplify the mutated fragment was carried out in a manner identical to that described above except that the template DNA consisted of the two overlapping fragments synthesized as previously discussed. The final 430 base pair amplification product containing the desired mutation flanked by unique KpnI and SphI restriction sites was ligated into the rat CaN A gene following removal of the wild type sequence with KpnI and SphI digestion. Insertion of the mutated nucleotide sequence was by confirmed by sequencing.

The rat brain CaN A/NIR mutant was then subcloned into the arabioSpec2 vector to produce biotinylated mutated CaN A/NIR.

The biotinylated wild type and mutated CaN A were used as ligand in the AKAP 79/CaN A binding assay described in In order to determine if the mutated CaN A protein retained phosphatase activity, a CaN holo-enzyme was reconstituted. One micromole of purified wild type or mutant CaN A was incubated with equal molar amount of purified CaN B (Chemicon), and calmodulin (Sigma) in 50 mM Hepes, pH 7.5, 1 mM $MnCl_2$, 0.5 mM EDTA, 1 mM DDT, and 2 mg/ml BSA, for 24 hours at 4° C., after which 33 nM of the reconstituted complex was used in a calcineurin phosphatase assay using $^{32}P$-inhibitor 1 as substrate as described in Example 14.

In association with CaN B, both wild type CaN A and mutant CaN A showed the same level (33%) of dephosphorylation of substrate after a ten minute incubation at room temperature, suggesting that the mutant CaN A maintained enzymatic activity. As a control, CaN A in buffer alone and no CaNB produced no phosphatase activity.

To further examine the functionality of the mutant, purified wild type and mutant CaN A proteins are tested for the ability to bind FKBP12 in the following assay. Initially FKBP12 was cloned as follows.

DNA encoding FKBP12 (FK506BP) was amplified from a macrophage cDNA library as a 327 base pair fragment using primers MH99 and MH101.

```
         NcoI
MH 99:   5' CCGCCGCCATGGGAGTGCAGTGG 3'        SEQ ID NO: 73

MH 101:  5' GGAGGCCACATTCCAGTTTTAGAAGCTCC 3'  SEQ ID NO: 74
```

The amplification product was purified over a C6LB column, digested with NcoI and BamHI. isolated on a 0.8% LMA gel and subcloned into the vector arabio1b previously digested with NcoI and BglII. Several positive clones were determined to contain a 327 base pair insert. Miniprep (MP) #2 was sequenced and verified to be the correct. The resulting plasmids was designated bioFKBP12. In order to keep the parameters of binding as similar to that for TRX-AKAP 79 binding to CaN A as described in Examples 8 and 15, FKBP12 was expressed as a TRX fusion protein which could captured on anti-mouse ScintiStrip plates.

An NcoI-BglII/BamHI fragment from plasmid bioP-KBP22 was ligated into the TRX Nco expression plasmid (described in Example 8) previously digested with NcoI and HindIII to give resulting plasmid TRXFKBP12. After transformed E. coli with this plasmid, FKBP12 can be isolated in the soluble fraction as a TRX fusion protein.

In order to insure that the CaN A/NIR mutant maintained the ability to bind other proteins, for example, FKBP12, a binding assay was developed to assess the capacity of CaN A/NIR to bind TRXFKBP12. The FKBP12 fusion protein was captured onto ScintiStrip plates in a manner similar to capture of TRX-AKAP 79. Briefly, bacterial cell lysate (5 $\mu$g protein/ml), from E. coli previously transformed with plasmid TRXFKBP12, was mixed with 2.5 $\mu$g/ml mouse anti-TRX monoclonal antibody in buffer containing PBS and 0.2% BSA. The mixture was added to the ScintiStrip plates previously coated with anti-mouse antibodies and blocked with 2.5% milk in 50 mM sodium citrate and 145 mM sodium chloride. Biotinylated wild type CaN A or the CaN A/NIR mutant (0 to 1 $\mu$M) was added to the wells in buffer containing 50 mM Tris, pH 7.5, 1 mM DTT, 1 mM $CaCl_2$, 0.5 mM $MnCl_2$, 3 $\mu$g/ml calmodulin, 500 ng/ml FK506 (Fugisawa, Japan) and two times molar excess of CaN B (Chemicon). Incubation was carried out for 1 to 2 hours at 37° C. Non-specifically bound proteins were removed with repeated washes with PBS containing Streptavidin-Eu/DELFIA® as described in Example 15. The $B_{max}$ of the NIR mutant was 120% of that of the wild type protein, with $K_d$ for CaN A binding between 60 and 113 nM values for the mutant and wild type proteins. The results suggest that both the wild type and NIR Can A mutants have a high binding affinity for FKBP12 despite the observed diminished binding of the NIR mutant to TRX-AKAP 79.

EXAMPLE 17

RI And CaN A Clone 11.1 Binding Sites On AKAP 79

In order to determine the binding domains for RI and CaN A on AKAP 79, a series of AKAP 79 amino- and carboxy-terminal deletion mutants were constructed and analyzed in the dihybrid system. Mutants were constructed employing the Promega Erase-a-Base System according to the method of Heinkoff [Gene 28:357 (1984)]. To use this system, the "bait" plasmid, pAS1 AKAP 79, was modified by introducing a KpnI restriction enzyme site 5' to the AKAP 79 initiating methionine to facilitate cloning of amino terminal deletions. For this construct, two complementary oligonucleotides, MH136 and MIH137 (SEQ ID NOs: 67 and 68) were designed which contained the pAS1 polylinker sequence with an additional KpnI site. The oligonucleotides were annealed, digested with NdeI and BamHI, and ligated into pAS1. AKAP 79 was then subcloned into the NcoI/BamHI site of the modified vector.

```
MH136  TATGGGTACCGCTGCTGCTGCTGCCATGGAGGCCCCGGG      SEQ ID NO: 67

MH137  GATCCCCGGGGCCTCCATGGCAGCAGCAGCAGCGGTACCCA    SEQ ID NO: 68
```

A second modified expression construct was created by introducing a KpnI site 3' to the AKAP 79 stop codon in order to facilitate cloning of carboxy terminal deletions. This construct was created by amplifying an AKAP 79 fragment and introducing a KpnI site at the 3' end of the coding sequence. The fragment was digested and cloned into the NcoI/SalI site of pAS1 and the construct verified by automated sequencing.

In all, seven carboxy terminal and five amino terminal mutants were produced. These mutants were verified by automated sequencing and transformed into y190α along with pACT (negative control), pACT RII (positive control), pACT CaN A 11.1 and pACT RI by previously described methods. β-galactosidase filter assays were performed on these transformants as previously described.

Only one amino terminal deletion encoding amino acids 52–427 could be analyzed in the dihybrid method because all other amino terminal truncations activated β-galactosidase reporter gene expression in the presence of the negative control. The 52–427 mutant was shown to bind RII, RI and CaN A 11.1. Of the carboxy terminal deletions, which individually deleted residues carboxy to amino acids 146, 236, 280, 334, 370, 378 and 396 were negative for both RI and RII binding suggesting RI may share the same amphipathic alpha helix which binds RII (amino acids 388 to 409) [Car, et al J.Biol. Chem. 266:14188–14192 (August 1991)]. A region of importance to the CaN A binding site was located between amino acid 236–280 as indicated by the observations that truncations 280, 334, 370 and 396 could interact with CaN A while truncations 146 and 236 could not bind.

EXAMPLE 18

The previous demonstration that AKAP 79 binds calcineurin is relevant in view of the fact that calcineurin is the target of two potent and clinically useful immunosuppressive, cyclosporin and FK506, both of which inhibit calcineurin activity. As described below, both cyclosporin and FK506 are useful in treatment of a variety of diseases, but have significant limiting side effects.

Presumably, factors which modulate anchoring protein/ calcineurin binding may ultimately modulate calcineurin activity in a manner similar to the activities of cyclosporin or FK506. Identification of such a modulator, particularly with fewer side effects than those observed with other immunosuppressants, would possibly have widespread therapeutic use treatment of a multitude of disease currently treated with cyclosporin or FK506.

Numerous clinical indications of cyclosporin and FK506 have been reported. For example, cyclosporin has defined the standard for post-transplant immunosuppression, making possible liver, lung, intestine, and pancreas transplants, even though FK506 is generally believed to be a stronger immunosuppressive. Transplant patients who do not tolerate or fail on either cyclosporin or FK506 are sometimes successfully changed to the other drug.

As another example, inflammatory bowel disease (IBD) is a common term for two diseases having different clinical appearances, Crohn's disease and ulcerative colitis (UC). Cyclosporin has been successfully used to treat Crohn's disease, with statistically significant results of treatment having been demonstrated in at least one index of disease activity [Brynskov, Dan.Med.Bull. 41:332–344 (1994)]. Other indices, however, that correlate best with resolution of acute exacerbations showed non-significant trends toward improvement. Cyclosporin has also shown activity in severe acute steroid-resistant UC (the data are not significant as the trial was stopped for ethical reasons). Another trial of patients with sclerosing cholangitis and UC demonstrated borderline significance toward a milder course of UC. Relapse was common after withdrawal and treatment has been limited by concern for toxicity [Choi and Targan, Dig.Dis. and Sci. 39:1885–1892 (1994)]. In addition, other immunosuppressives have been used successfully in IBD, such as methotrexate, azathioprine, and 6-MP.

As another example, cyclosporin has been demonstrated to be effective in treating rheumatoid arthritis in several trials when used as a second or third line therapy of the disease, i.e., in patients that have failed other established therapies and have severe disease. In these trails, cyclosporin was found to be generally as effective and toxic as other second-line agents, such as gold, antimalarials, azathioprine, D-penicillamine, and methotrexate [Wells and Tugwell, Br.J.Rheum., 32(suppl 1):51–56 (1993); Forre et al., Arth.Rheum., 30:88–92 (1987)]. The trials only report treatment of "very severe, refractory active RA" because of cyclosporin's "potentially irreversible toxicity" [Dougados and Torley, Br.J.Rheum., 32(suppl 1):57–59 (1993)]. The renal toxicity is thought to have been primarily mediated through renal vasoconstriction that exacerbates NSAID nephrotoxicity and renal disease inherent in rheumatoid arthritis [Leaker and Cairns, Br.J.Hosp.Med., 52:520–534 (1994); Sturrock et al., Nephrol.Dial. Transplant, 9:1149–1156 (1994); Ludwin and Alexopolulou, Br.J.Rheum., 32(suppl 1):60–64 (1993)]. About 10% of renal biopsies from RA patients treated with cyclosporin showed morphological features of cyclosporin toxicity [International Kidney Biopsy Registry of Cyclosporin in Autoimmune Diseases, Br.J.Rheum., 32(suppl 1):65–71 (1993)].

As still another example, cyclosporin has been reported to be effective for treatment of steroid-dependent asthma. In one trial, a small number of patients were randomized to cyclosporin or placebo, and the cyclosporin group exhibited increased airflow and FVC as well as fewer rescue courses of prednisolone.

As another example, cyclosporin was shown to be effective in the treatment of steroid-dependent minimal change disease nephrotic syndrome. Patients in this trial were shown to have lower steroid requirements on low dose cyclosporin, but all relapsed when cyclosporin was discontinued. Steroid-resistant forms of nephrotic syndrome have only a 20–30% response rate to cyclosporin [Meyrier, Nephrol.Dial. Transplant, 9:596–598 (1994); Hulton et al., Pediatr.Nephrol., 8:401–403 (1994)].

With regard to treatment of systemic lupus erythematosus (SLE), one study reported significant decrease of SLE activity indices in a prospective non-randomized, non-controlled study [Tokuda et al.,Arthr.Rheumat., 37:551–558 (1994)]. Other studies, however, have not demonstrated efficacy in SLE.

As another example, cyclosporin has been shown to induce remission in insulin-dependent diabetes mellitus when instituted early after initial presentation. Remissions averaged about one year, although some were extended up to 850 days [Jenner et al., Diabetologia, 35:884–888 (1992); Bougneres et al., Diabetes, 39:1264–1272 (1990)]. No long-lasting effect of cyclosporin was noted in extended follow-up of one study [Martin et al., Diabetologia, 34:429–434 (1991)]. In another study, however, renal function deteriorated during treatment for 12–18 months and did not return completely to placebo level indicating that some chronic renal injury may have occurred [Feldt-Rasmussen et al., Diabetes Medicine, 7:429–433 (1990)]. Earlier intervention would be needed to enhance the effect of immunosuppressive therapy on the course of insulin-dependent diabetes mellitus. Some investigators are screening first degree relatives and successfully prophylactically treating those with diabetic markers [Elliott and Chase, Diabetologia, 34:362–365 (1991)].

As still another example, psoriasis has been effectively treated by cyclosporin [Cuellar et al., Balliere's Clin. Rheum., 8:483–498 (1994); Ellis et al., JAMA 256:3110–3116 (1986)]. High dose therapy was effective for treatment of psoriatic arthritis, a particularly serve form of destructive arthritis, and discontinuation of therapy was generally followed by exacerbation of skin and joint disease. In view of the potential side effects and the need for continuous long term treatment, cyclosporin is only indicated for refractory psoriatic arthritis that is not adequately treated by other means.

In addition, cyclosporin has been demonstrated to be effective for treatment of severe atopic dermatitis in placebo-controlled and double-blinded studies [Van Joost et al., Br.J.Derm., 130:634–640 (1994); Cooper, J.Invest.Derm., 102:128–137 (1994)]. Side effects of nausea, abdominal discomfort, paresthesias, cholestasis, and renal insufficiency from the drug were preferred by patients to their untreated disease. Another randomized double-blind, placebo-controlled study found that cyclosporin treatment significantly increased the quality of life for patients with severe atopic dermatitis [Salek et al., Br.J.Derm., 129:422–430 (1993)]. Skin lesions quickly relapsed following cessation of cyclosporin, but quality of life remained improved.

As still another example, cyclosporin has been used in treatment of chronic dermatitis of the hands, a disease with a reported prevalence of 4–22%, and typically treated with topical steroids to which many patients, however, do not respond. Low dose cyclosporin has been shown to effectively treated 6/7 patients in an open study [Reitamo and Granlund, Br.J.Derm., 130:75–78 (1994)]. Approximately half of the patients relapsed after cyclosporin was discontinued.

As still another example, cyclosporin has been utilized in treatment of urticaria and angioedema, idiopathic skin diseases that present as hives and subcutaneous swelling. The pathology is related to mast cells, and treatment is often ineffective. In one trial, three patients with refractory urticaria and angioedema were treated with cyclosporin and all symptoms resolved within one week [Fradin et al., *J.Am.Acad.Derm.*, 25:1065–1067 (1991)]. All patients had to stop therapy because of side effects, and symptoms recurred after therapy was discontinued.

With regard to other rheumatological diseases, studies report effective cyclosporin treatment of other less common autoimmune diseases, including Behcet's Disease [Pacor et al., *Clin.Rheum.*, 13:224–227 (1994)], Wegner's Granulomatosis [Allen et al., *Cyclosporin A Therapy for Wegner's Granulomatosis* in ANCA-Associated Vasculitides: Immunological and Clinical Aspects, Gross ed. Plenum Press (1993)], and immune-mediated thrombocytopenia [Schultz et al., *Blood* 85:1406–1408 (1995)].

In many of the trials described above, use of cyclosporin or FK506 was associated with many undesired side effects. In general, increased risk of infection and malignancy are associated with general immunosuppression, and it is unlikely that an anchoring protein-related immunosuppressive would not have similar risks. Other side effects may be avoided or reduced, however, by anchoring protein tissue specificity. The most common serious side effect of both cyclosporin and FK506 is nephrotoxicity, which at least to some degree is dose related and occurs in most patients, generally in the form of a decrease in the glomerular filtration rate during treatment. This side effect, however, is at least partially reversible when the drug is discontinued [Leaker and Cairns, supra]. Typically, progressive renal insufficiency does not develop, although more follow-up is needed for definitive evaluation. Chronic injury has also been observed in patients receiving low dose cyclosporin (3–4 mg/kg/d), about 40% of biopsies of these patients showed changes of interstitial fibrosis, tubular atrophy, and arteriolopathy [Svarstad et al., *Nephrol.Dial.Transplant*, 9:1462–1467 (1994); Young et al., *Kidney International*, 46:1216–1222 (1994)]. Changes in endothelial cells were also apparent in histological sections [Kahan, *N.Engl.J.Med.*, 321:1725–1748 (1989)]. The nephrotoxicity was postulated to have resulted primarily due to arteriolar vasoconstriction and chronic low-grade ischemia [Leaker and Carins, supra], although the drugs were also shown to be directly toxic to tubular cells and vascular interstitial cells [Platz et al., *Transplantation*, 58:170–178 (1994)]. Some reports indicate that the incidence and severity of nephrotoxicity may be slightly higher with FK506 [Platz et al., supra].

Another reported significant toxicity of both cyclosporin and FK506 was neurotoxicity, with clinical manifestations including seizures, confusion, blindness, coma, headache, ataxia, Parkinson's syndrome, paresthesias, psychosis, focal deficits, akinetic mutism, tremors, neuropathy, and sleep disturbances [Shimizu et al., *Pediatr. Nephrol.*, 8:483–385 (1994); Wilson et al., *Muscle and Nerve*, 17:528–532 (1994); Reece et al., *Bone Marrow Transpl.*, 8:393–401 (1991); Eidelman et al., *Transpl.Proc.*, 23:3175–3178 (1991); de Groen et al., *N.Engl.J.Med.*, 317:861–566 (1987)]. Following liver transplantation, moderate to severe neurotoxicity has been shown to occur in 10–20% of patients treated with FK506 and 3–12% of patients treated with cyclosporin. Neurotoxicity has also been associated with serum lipid abnormalities and liver dysfunction.

Other side effects of cyclosporin and/or FK506 include hepatotoxicity, glucose intolerance, hypertension, hirsutism, gastrointestinal symptoms, venous thrombosis, pancreatitis, and gingival hyperplasia [Morris, *J.Heart Lung Transplant*, 12:S275–S286 (1993); Fung et al., *Transpl. Proc.*, 23:3105–3108 (1991); Mason, *Pharmacol. Rev.*, 42:423–434 (1989); Kahan, *N.Engl.J.Med.*, 321:1725–1738 (1989); Thomason et al., *Renal Failure*, 16:731–745 (1994)]. Therefore, in view of the widespread utilization of cyclosporin and PK506 and the inherent side effects of their use, development of alternative immunosuppressives could be extremely beneficial.

For example, it is possible that delocalization of calcineurin from a putative T cell anchoring protein might inhibit calcineurin activity in T cell activation, and thereby providing a T cell-specific immunosuppressive having the utility of cyclosporin or FK506, but fewer side effects. The previous observation that delocalization of PKA from a T cell anchoring protein enhanced IL-2 expression in stimulated cells indicated that anchoring protein-localized PKA in some way contributes to a regulatory role in IL-2 expression during T cell activation. T cell-specific delocalization of PKA may therefore provide a means for enhancing IL-2 secretion in vivo, thereby mimicking recombinant IL-2 administration and possibly reducing previously reported toxicity of IL-2 treatment as described below.

IL-2 has been approved for treatment of metastatic renal carcinoma and approximately 15–20% of patients with metastatic renal cell carcinoma or malignant melanoma respond to IL-2 therapy. Some of these responses are durable, lasting more than 66 months [Dillman, *Cancer Biotherapy*, 9:183–209 (1994); Whittington and Faulds, *Drugs* 46:446–514 (1993)]. While high dose bolus therapy has been associated with several severe side effects (as described below), low dose subcutaneous or continuous infusion therapy produced a modest response rate (12%) while reducing toxicity [Vogelzang et al., *J.Clin.Oncol.*, 11:1809–1816 (1993)].

IL-2 therapy (with and without interferon-α and other agents) has been investigated in the treatment of other malignancies. For example, sustained clinical responses, but no cures, have been obtained in direct application of IL-2 to tumor beds following glioma resection [Merchant et al., *J.Neuro.*, 8:173–188 (1990)]. In still other trials, limited efficacy has been reported in lymphoma [Dillman, supra], colorectal carcinoma [Whittington and Faulds, supra], limited AML [Bruton and Koeller, *Pharmacotherapy*, 14:635–656 (1994)], ovarian cancer and early bladder cancer [Whittington and Faulds, supra.]. The number of participants in each of these studies was too small to permit significant conclusions regarding effectiveness, however.

IL-2 has also been used in combination with adoptive immunotherapy, and been demonstrated to be effective for treatment of metastatic renal carcinoma [Pierce et al., *Sem. Oncol.*, 22:74–80 (1995); Belldegrun et al., *J. Urol.*, 150:1384–1390 (1993)]. In addition, IL-2 may also be effective for treatment of certain infectious diseases, by decreasing skin bacterial load and levels of antigen in patients with leprosy following by intradermal injection [Kaplan, *J.Infect.Dis.*, 167(suppl 1):S18–22 (1993)]. Also it has been observed that, as compared to PPD-positive healthy controls, lymphocytes from patients with tuberculosis produce lower levels of IL-2 [Sanchez et al., *Inf.Immun.*, 62:5673–5678 (1994)], suggesting that IL-2 therapy may be of value in treatment of mycobacterial infections.

Despite the potential therapeutic value of IL-2, the cytokine is also associated with significant toxicity [unless otherwise noted, sources are Whittington and Faulds, Dillman and Bruton and Koeller, supra]. The major treatment-limiting side effects is capillary leak syndrome. IL-2 administration increases vascular permeability causing interstitial and pulmonary edema, with patients developing hypotension with a substantial number requiring pressors. Vigorous fluid resuscitation can cause life-threatening pulmonary edema. Up to 20% of patients may require intubation and mechanical ventilation. High does bolus administration causes more severe leak than low dose or slow continuous infusions, and in some regiments, 100% of patients require ICU support during IL-2 treatment. Myocarditis, cardiomyopathies and cardiac arrhythmias have also been observed. Acute renal failure may occur as a result of the capillary leak syndrome-induced hypotension.

IL-2 can also cause severe diarrhea with electrolyte imbalances, cholestasis, thyroid abnormalities, and acute pancreatitis. Anemia requiring transfusions occurs in 15–20% of treated patients [MacFarlane et al., *Cancer* 75:1030–1037 (1995)]. Thrombocytopenia with hemorrhage can occur and coagulation pathway defects are common. Over 70% of patients experience changes in mental status, including paranoid delusions, hallucinations, loss of interest, sleep disturbances, and drowsiness. Coma, visual defects, transient ischemic attacks, and paresthesias have also been reported. These drawbacks associated with exogenous with exogenous IL-2 suggest that alternatives, wherein, for example, endogenous IL-2 production can be modulated and thus eliminate the requirement for exogenous IL-2 treatment, should be explored as potential therapeutics.

In addition to providing possible means to identify immunosuppressive drugs and modulators of IL-2 production, identification of anchoring proteins makes regulation of other cellular activity possible in view of the diverse metabolic pathways in which anchoring proteins have been shown to participate. For example, AKAP 79 is important in regulation of glutamate receptor-regulated ion channels in the post-synaptic density of neurons, presumably via binding PKA, PKC, and calcineurin. PKA regulates activity of AMPA receptor-regulated channels, and delocalization or inhibition of PKA attenuates AMPA ion channel activity. PKC regulates activity of NMDA receptor-regulated channels, and calcineurin has been shown to desensitize the NMDA receptor to stimuli. These observations indicate that localized kinases (PKA and PKC) may regulate activity of glutamate receptors in neurons. Dephosphorylation by calcineurin is the counter-regulatory mechanism of the NMDA receptors. This model agrees physiologically with evidence of seizures induced by cyclosporin or FK506.

In addition, glutamate receptors have been implicated in many neurological diseases. Glutamate and other excitatory amino acids can produce excitotoxicity in neurons, and excessive stimulation of postsynaptic glutamate receptors has been shown to be toxic to the neurons, causing acute neuronal degeneration. Hypoxia (such as following stroke or cardiac arrest) and CNS trauma have been shown to cause a marked outpouring of glutamate into the extracellular space, which then interacts with glutamate receptors and triggers the excitotoxic cascade. Anti-excitatory agents have been shown to protect against brain injury in animals models [Olney, *Neurobiology of Aging*, 15:259–260 (1994)]. Interestingly, NMDA antagonists are toxic to some types of neurons indicating that glutamate may inhibit other excitatory pathways in those cells. Macrolide antibodies, such as FK506, have also been shown to protect against NMDA, but not kainate, excitotoxicity in cultured neurons [Manev, et al., *Brain Res.*, 624:331–335 (1993)].

Glutamate has also been implicated in Parkinson's Disease. NMDA antagonists protect dopaminergic neurons in substantia nigra in monkeys exposed to MPTP, a chemical that induces Parkinson's syndrome in humans and other primates. Amantidine and memantine are NMDA antagonists and have been used in Europe to treat Parkinson's disease, however, both have been shown to cause psychosis in some patients. There is also some evidence that glutamatergic neurons may be hyperactive in Parkinson's disease and inhibition could decrease the motor symptom's of the disease [Lange and Riederer, *Life Sciences*, 55:2067–2075 (1994)].

Glutamate also plays a role in seizure disorders, participating in initiation, spread, and maintenance of seizure activity. NMDA and non-NMDA antagonists are potent anticonvulsants [Meldrum, *Neurology*, 44(suppl 8):S14–S23 (1994)]. AMPA receptors have also been implicated in ALS and a trial of a receptor antagonist is currently in progress.

In view of the total of these observations, it is not surprising that numerous other immunosuppressants are in clinical trials. The following information regarding such trials was obtained from Haydon and Haynes, *Balliere's Clin. Gastroentero.*, 8:455–464 (1994); Thomason and Starzi, *Immunol.Rev.* 1993, 71–98 (1993); and Morris *J.Heart Lung Transplant.*, 12:S275–S286 (1993). For example, azaspirane is an SKB compound that suppresses graft cellular infiltrates and induction of IL-2R, and also abolishes IL-2 and IFN-γ production. Apparently azaspirane induces some type of suppressor cell and there is some evidence of synergistic effects with cyclosporin.

As another example, mycophenolate mofetial is a Syntex compound which inhibits purine synthesis and has a T and B cell-selective antiproliferative effect. It depletes antibodies. Mycophenolate mofetial may also deplete adhesion molecules from cell surfaces. While the drug apparently has low toxicity, it may cause leukopenia, and has been used to treat psoriasis for 20 years.

As another example, mizoribine in a Sumitomo compound which inhibits DNA synthesis. The mechanism of action is identical to mycophenolate.

As another example, brequinar is a DuPont-Merck compound which inhibits pyrimidine synthesis by blocking dihydoorate dehydrogenase. Full reports of clinical trials are awaited. The drug has been reported to act synergistically with cyclosporin, but can cause thrombocytopenia, dermatitis and mucositis.

As still another example, 15-Deoxyspergualin is a Nippon-Kayaku compound which predominantly affects monocyte/macrophage function, including inhibition of oxidative metabolism, lysosomal enzyme synthesis, IL-1 production, and cell surface expression of MHC class II antigens. It is 70–90% effective in refractory kidney rejection, but bone marrow toxicity may occur at higher doses.

As another example, leflunomide is a Hoechst compound which inhibits cytokine action, blocks T cell activation and antibody synthesis. It is not toxic to the kidneys or bone marrow.

As another example, rapamycin is a Wyeth-Ayerst compound that is related to FK506. It is a prodrug that must bind an immunophillin to be active and does no inhibit calcineurin or block T cell cytokine production. By an unknown mechanism, rapamycin blocks G1 to S transition.

Numerous modifications and variations in the invention as set forth in the above illustrative examples are expected to occur to those skilled in the art. Consequently only such limitations as appear in the appended claims should be placed on the invention.

Numerous modifications and variations in the invention as set forth in the above illustrative examples are expected to occur to those skilled in the art. Consequently only such limitations as appear in the appended claims should be placed on the invention.

What is claimed is:

1. A calcineurin deletion mutant which binds AKAP79 selected from the group of the calcineurin polypeptides consisting of amino acids 1–400, 1–375, 1–354, 30–375, 1–347, 1–340, 1–338, and 1–336 of SEQ ID NO:7.

* * * * *

UNITED STATES PATENT AND TRADEMARK OFFICE
CERTIFICATE OF CORRECTION

PATENT NO. : 6,107,104
DATED : August 22, 2000
INVENTOR(S) : Lockerbie et al.

It is certified that error appears in the above-identified patent and that said Letters Patent is hereby corrected as shown below:

Column 10,
Line 14, please delete "MATα" and add -- MATE --.

Column 12,
Line 23, please delete "defme" and add -- define --.

Column 13,
Line 21, please delete "y190 a" and add -- y190a --.

Column 16,
Line 61, please delete "XhaI" and add -- XbaI --.

Column 22,
Line 12, please delete "ben" and add -- been --.

Column 24,
Line 43, please delete "Plasmid Plasmid" and add -- Plasmid. Plasmid --.

Column 33,
Line 39, please delete "fmally" and add -- finally --.

Column 35,
Line 37, please delete "$_{of\ approximately}$" and add -- approximately --.

Column 37,
Line 19, please delete "subdloned" and add -- subcloned --.

Column 39,
Lines 19 and 20, please delete "bioPKBP22" and add -- bioFKP12 --.

UNITED STATES PATENT AND TRADEMARK OFFICE
CERTIFICATE OF CORRECTION

PATENT NO. : 6,107,104
DATED : August 22, 2000
INVENTOR(S) : Lockerbie et al.

It is certified that error appears in the above-identified patent and that said Letters Patent is hereby corrected as shown below:

Column 47,
Line 3, please delete "no" and add -- not --.

Column 77,
Line 13, please delete "63 base pairs" and add -- 64 base pairs --.

Signed and Sealed this

Twenty-fifth Day of December, 2001

*Attest:*

*Attesting Officer*

JAMES E. ROGAN
*Director of the United States Patent and Trademark Office*

```
                           SEQUENCE LISTING (1) GENERAL INFORMATION:

(iii) NUMBER OF SEQUENCES: 74

(2) INFORMATION FOR SEQ ID NO:1:

(i) SEQUENCE CHARACTERISTICS:
          (A) LENGTH: 13 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:1:

Arg Arg Lys Arg Ser Gln Ser Ser Lys Glu Glu Lys Pro
1               5                  10

(2) INFORMATION FOR SEQ ID NO:2:

(i) SEQUENCE CHARACTERISTICS:
          (A) LENGTH: 15 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:2:

Arg Arg Lys Arg Ser Gln Ser Ser Lys Glu Glu Lys Pro Leu Gln
1               5                  10                  15

(2) INFORMATION FOR SEQ ID NO:3:

(i) SEQUENCE CHARACTERISTICS:
          (A) LENGTH: 15 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:3:

Arg Arg Lys Arg Ser Gln Ser Ser Lys Glu Glu Lys Pro Phe Lys
1               5                  10                  15

(2) INFORMATION FOR SEQ ID NO:4:

(i) SEQUENCE CHARACTERISTICS:
          (A) LENGTH: 24 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:4:
```

```
Asp Leu Ile Glu Glu Ala Ala Val Ser Arg Ile Val Asp Ala Val Ile
1               5                  10                 15

Glu Glu Val Lys Ala Ala Gly Ala
            20
```

(2) INFORMATION FOR SEQ ID NO:5:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Gly Arg Arg Asn Ala Ile His Asp Ile
1               5
```

(2) INFORMATION FOR SEQ ID NO:6:

(i) SEQUENCE CHARACTERISTICS:
        (A) LENGTH: 2257 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1461

(xi) SEQUENCE DESCRIPTION: SEQ ID NO:6:

```
CCG CCC CCG CCC CCG CCC CCA CCG CCC CCT CTC GGG GCC GAC CGC GTC        48
Pro Pro Pro Pro Pro Pro Pro Pro Pro Pro Leu Gly Ala Asp Arg Val
1               5                   10                  15

GTC AAA GCT GTT CCT TTT CCC CCA ACT CAT CGG CTG ACA TCT GAA GAA        96
Val Lys Ala Val Pro Phe Pro Pro Thr His Arg Leu Thr Ser Glu Glu
                20                  25                  30

GTG TTT GAT ATG GAT GGG ATA CCC AGG GTT GAT GTT CTG AAG AAC CAC       144
Val Phe Asp Met Asp Gly Ile Pro Arg Val Asp Val Leu Lys Asn His
            35                  40                  45

TTG GTA AAA GAA GGG CGG GTG GAT GAA GAA ATT GCA CTA AGA ATT ATC       192
Leu Val Lys Glu Gly Arg Val Asp Glu Glu Ile Ala Leu Arg Ile Ile
        50                  55                  60

AAT GAG GGT GCT GCC ATA CTT CGG CGG GAG AAA ACC ATG ATA GAA GTA       240
Asn Glu Gly Ala Ala Ile Leu Arg Arg Glu Lys Thr Met Ile Glu Val
65                  70                  75                  80

GAA GCT CCA ATT ACA GTG TGT GGT GAC ATC CAT GGC CAA TTT TTT GAT       288
Glu Ala Pro Ile Thr Val Cys Gly Asp Ile His Gly Gln Phe Phe Asp
                85                  90                  95

CTG ATG AAA CTT TTT GAA GTA GGA GGA TCA CCT GCT AAT ACA CGA TAC       336
Leu Met Lys Leu Phe Glu Val Gly Gly Ser Pro Ala Asn Thr Arg Tyr
            100                 105                 110

CTT TTT CTT GGT GAT TAT GTG GAC AGA GGT TAT TTT AGT ATA GAG TGT       384
Leu Phe Leu Gly Asp Tyr Val Asp Arg Gly Tyr Phe Ser Ile Glu Cys
        115                 120                 125

GTC TTA TAT TTA TGG GTC TTG AAG ATT CTA TAC CCA AGC ACA TTA TTC       432
Val Leu Tyr Leu Trp Val Leu Lys Ile Leu Tyr Pro Ser Thr Leu Phe
    130                 135                 140

CTT CTG AGA GGC AAC CAT GAA TGC AGA CAC CTT ACT GAA TAT TTT ACC       480
Leu Leu Arg Gly Asn His Glu Cys Arg His Leu Thr Glu Tyr Phe Thr
145                 150                 155                 160
```

```
TTT AAG CAG GAA TGT AAA ATT AAA TAT TCA GAA AGA GTC TAT GAA GCT        528
Phe Lys Gln Glu Cys Lys Ile Lys Tyr Ser Glu Arg Val Tyr Glu Ala
                165                 170                 175

TGT ATG GAG GCT TTT GAC AGC TTG CCC CTT GCT GCA CTT CTA AAC CAA        576
Cys Met Glu Ala Phe Asp Ser Leu Pro Leu Ala Ala Leu Leu Asn Gln
            180                 185                 190

CAA TTT CTT TGT GTT CAT GGT GGA CTT TCA CCA GAA ATA CAC ACA CTG        624
Gln Phe Leu Cys Val His Gly Gly Leu Ser Pro Glu Ile His Thr Leu
                195                 200                 205

GAT GAT ATT AGG AGA TTA GAT AGA TTT AAA GAG CCA CCT GCA TTT GGA        672
Asp Asp Ile Arg Arg Leu Asp Arg Phe Lys Glu Pro Pro Ala Phe Gly
210                 215                 220

CCA ATG TGT GAC TTG CTA TGG TCT GAT CCT TCT GAA GAC TTT GGA AAT        720
Pro Met Cys Asp Leu Leu Trp Ser Asp Pro Ser Glu Asp Phe Gly Asn
225                 230                 235                 240

GAA AAA TCA CAA GAA CAT TTT AGT CAT AAT ACA GTT CGA GGA TGT TCT        768
Glu Lys Ser Gln Glu His Phe Ser His Asn Thr Val Arg Gly Cys Ser
                245                 250                 255

TAT TTT TAT AAC TAT CCA GCA GTG TGT GAA TTT TTG CAA AAC AAT AAT        816
Tyr Phe Tyr Asn Tyr Pro Ala Val Cys Glu Phe Leu Gln Asn Asn Asn
                260                 265                 270

TTG TTA TCG ATT ATT AGA GCT CAT GAA GCT CAA GAT GCA GGC TAT AGA        864
Leu Leu Ser Ile Ile Arg Ala His Glu Ala Gln Asp Ala Gly Tyr Arg
                275                 280                 285

ATG TAC AGA AAA AGT CAA ACT ACA GGG TTT CCT TCA TTA ATA ACA ATT        912
Met Tyr Arg Lys Ser Gln Thr Thr Gly Phe Pro Ser Leu Ile Thr Ile
290                 295                 300

TTT TCG GCA CCT AAT TAC TTA GAT GTC TAC AAT AAT AAA GCT GCT GTA        960
Phe Ser Ala Pro Asn Tyr Leu Asp Val Tyr Asn Asn Lys Ala Ala Val
305                 310                 315                 320

CTA AAG TAT GAA AAT AAT GTG ATG AAC ATT CGA CAG TTT AAT TGC TCT       1008
Leu Lys Tyr Glu Asn Asn Val Met Asn Ile Arg Gln Phe Asn Cys Ser
                325                 330                 335

CCA CAT CCT TAT TGG TTG CCC AAT TTT ATG GAT GTC TTT ACA TGG TCC       1056
Pro His Pro Tyr Trp Leu Pro Asn Phe Met Asp Val Phe Thr Trp Ser
                340                 345                 350

TTA CCA TTT GTT GGA GAA AAA GTG ACA GAA ATG TTG GTA AAT GTT CTG       1104
Leu Pro Phe Val Gly Glu Lys Val Thr Glu Met Leu Val Asn Val Leu
                355                 360                 365

AGT ATT TGT TCT GAT GAT GAA CTA ATG ACA GAA GGT GAA GAC CAG TTT       1152
Ser Ile Cys Ser Asp Asp Glu Leu Met Thr Glu Gly Glu Asp Gln Phe
370                 375                 380

GAT GTA GGT TCA GCT GCA GCC CGG AAA GAA ATC ATA AGA AAC AAG ATC       1200
Asp Val Gly Ser Ala Ala Ala Arg Lys Glu Ile Ile Arg Asn Lys Ile
385                 390                 395                 400

CGA GCA ATT GGC AAG ATG GCA AGA GTC TTC TCT GTT CTC AGG GAG GAG       1248
Arg Ala Ile Gly Lys Met Ala Arg Val Phe Ser Val Leu Arg Glu Glu
                405                 410                 415

AGT GAA AGC GTG CTG ACA CTC AAG GGC CTG ACT CCC ACA GGG ATG TTG       1296
Ser Glu Ser Val Leu Thr Leu Lys Gly Leu Thr Pro Thr Gly Met Leu
                420                 425                 430

CCT AGT GGA GTG TTG GCT GGA GGA CGG CAG ACC TTG CAA AGT GGT AAT       1344
Pro Ser Gly Val Leu Ala Gly Gly Arg Gln Thr Leu Gln Ser Gly Asn
            435                 440                 445

GAT GTT ATG CAA CTT GCT GTG CCT CAG ATG GAC TGG GGC ACA ACT CAC       1392
Asp Val Met Gln Leu Ala Val Pro Gln Met Asp Trp Gly Thr Thr His
450                 455                 460

TCT TTT GCT AAC AAT ACA CAT AAT GCA TGC AGG GAA CTC CTT CTG CTT       1440
Ser Phe Ala Asn Asn Thr His Asn Ala Cys Arg Glu Leu Leu Leu Leu
465                 470                 475                 480
```

-continued

```
TTT AGT TCC TGT CTT AGC AGC TGACATATGC AGGGTATTAT GTGATAGGCA          1491
Phe Ser Ser Cys Leu Ser Ser
              485

TCTGATTAGT ACCTGGCCAG GGCATAATAT TGATAGAACA AGTTGTCTTT TAACTGAAAA     1551

TAACAATCAG TTTCCCAGAT TTTCATAAGG TGATATGGGG AGCAGCTCAT GTCATAATTC     1611

CGAAATATTT ATTCATTTGT TTAATGCACC CCTTTCTTTC AAAAGCCTCA GTCAAGAATG     1671

TGAATCAGGG ATATATCTAT ATATCTATTT ACACACATAC ATAAATATAT ATAACTAAAA     1731

TGGAAATGTA ATTCCGAGTT TCTTACTTTT AAAATTTACG TAATTGTATT AGATTTTGCT     1791

TATGTTTTCA AGTATTTATT TTTTGAGTTA AAATTCTGCT TAGGCCCCAA AACTTCCTTT     1851

ATGCACTCAT TTGCCAAAAG ATTTATGCTA AATTTTGTAC CCTGGTAAAT GATTAGAGTT     1911

TGTTTTCTGT GGTGTTTGTC AAACGTTCTA TGTATAATTG ACTGTCTGTA ACATGCTGTT     1971

TCCTTCCTCT GCAGATATAG CTGCTTTCCT AAATCTGTCT GTCTTTCTTT AGGATAGCTG     2031

TATGTCTGTA AATATATGTT CAATTAAATT ACTCTATCAG ACGCTTGTCT GTCTTTTGAT     2091

GTAGAAGCAA CTTTGTAGCA CCTTGATTTT AGGTTTGCTG CATTTGTTGC TGCACTTGGT     2151

TCAGTCTGAA TATGAATGTA ACATTAGATA TTGAGCTATT GTTATAAAGG GTTGAATTTA     2211

AATCATGTAA GTCAAAATTG AAAGGGTGTT ATAAAGTGTG CCTTTA                    2257
```

(2) INFORMATION FOR SEQ ID NO:7:

(i) SEQUENCE CHARACTERISTICS:
       (A) LENGTH: 487 amino acids
       (B) TYPE: amino acid
       (D) TOPOLOGY: linear (ii) MOLECULE TYPE: protein (xi) SEQUENCE DESCRIPTION: SEQ ID NO:7:

```
Pro Pro Pro Pro Pro Pro Pro Pro Leu Gly Ala Asp Arg Val
  1               5                  10                  15

Val Lys Ala Val Pro Phe Pro Thr His Arg Leu Thr Ser Glu Glu
              20                  25                  30

Val Phe Asp Met Asp Gly Ile Pro Arg Val Asp Val Leu Lys Asn His
              35                  40                  45

Leu Val Lys Glu Gly Arg Val Asp Glu Glu Ile Ala Leu Arg Ile Ile
          50                  55                  60

Asn Glu Gly Ala Ala Ile Leu Arg Arg Glu Lys Thr Met Ile Glu Val
 65                  70                  75                  80

Glu Ala Pro Ile Thr Val Cys Gly Asp Ile His Gly Gln Phe Phe Asp
                  85                  90                  95

Leu Met Lys Leu Phe Glu Val Gly Gly Ser Pro Ala Asn Thr Arg Tyr
                 100                 105                 110

Leu Phe Leu Gly Asp Tyr Val Asp Arg Gly Tyr Phe Ser Ile Glu Cys
             115                 120                 125

Val Leu Tyr Leu Trp Val Leu Lys Ile Leu Tyr Pro Ser Thr Leu Phe
         130                 135                 140

Leu Leu Arg Gly Asn His Glu Cys Arg His Leu Thr Glu Tyr Phe Thr
145                 150                 155                 160

Phe Lys Gln Glu Cys Lys Ile Lys Tyr Ser Glu Arg Val Tyr Glu Ala
                 165                 170                 175

Cys Met Glu Ala Phe Asp Ser Leu Pro Leu Ala Ala Leu Leu Asn Gln
             180                 185                 190
```

-continued

```
Gln Phe Leu Cys Val His Gly Gly Leu Ser Pro Glu Ile His Thr Leu
            195                 200                 205

Asp Asp Ile Arg Arg Leu Asp Arg Phe Lys Glu Pro Pro Ala Phe Gly
210                 215                 220

Pro Met Cys Asp Leu Leu Trp Ser Asp Pro Ser Glu Asp Phe Gly Asn
225                 230                 235                 240

Glu Lys Ser Gln Glu His Phe Ser His Asn Thr Val Arg Gly Cys Ser
            245                 250                 255

Tyr Phe Tyr Asn Tyr Pro Ala Val Cys Glu Phe Leu Gln Asn Asn Asn
            260                 265                 270

Leu Leu Ser Ile Ile Arg Ala His Glu Ala Gln Asp Ala Gly Tyr Arg
            275                 280                 285

Met Tyr Arg Lys Ser Gln Thr Thr Gly Phe Pro Ser Leu Ile Thr Ile
290                 295                 300

Phe Ser Ala Pro Asn Tyr Leu Asp Val Tyr Asn Asn Lys Ala Ala Val
305                 310                 315                 320

Leu Lys Tyr Glu Asn Asn Val Met Asn Ile Arg Gln Phe Asn Cys Ser
            325                 330                 335

Pro His Pro Tyr Trp Leu Pro Asn Phe Met Asp Val Phe Thr Trp Ser
            340                 345                 350

Leu Pro Phe Val Gly Glu Lys Val Thr Glu Met Leu Val Asn Val Leu
            355                 360                 365

Ser Ile Cys Ser Asp Asp Glu Leu Met Thr Glu Gly Glu Asp Gln Phe
370                 375                 380

Asp Val Gly Ser Ala Ala Arg Lys Glu Ile Ile Arg Asn Lys Ile
385                 390                 395                 400

Arg Ala Ile Gly Lys Met Ala Arg Val Phe Ser Val Leu Arg Glu Glu
            405                 410                 415

Ser Glu Ser Val Leu Thr Leu Lys Gly Leu Thr Pro Thr Gly Met Leu
            420                 425                 430

Pro Ser Gly Val Leu Ala Gly Gly Arg Gln Thr Leu Gln Ser Gly Asn
            435                 440                 445

Asp Val Met Gln Leu Ala Val Pro Gln Met Asp Trp Gly Thr Thr His
450                 455                 460

Ser Phe Ala Asn Asn Thr His Asn Ala Cys Arg Glu Leu Leu Leu Leu
465                 470                 475                 480

Phe Ser Ser Cys Leu Ser Ser
                485

(2) INFORMATION FOR SEQ ID NO:8:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Ser Ile Lys Arg Leu Val Thr Arg Arg Lys Arg Ser Glu Ser Ser Lys
1               5                   10                  15

Gln Gln Lys Pro Phe Lys Ala Lys Leu Gln Ser Glu
            20                  25

(2) INFORMATION FOR SEQ ID NO:9:
```

(i) SEQUENCE CHARACTERISTICS:
    (A) LENGTH: 24 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:9:

Asp Leu Ile Glu Glu Ala Ala Ser Arg Ile Val Asp Ala Val Ile Glu
 1               5                  10                  15

Gln Val Lys Ala Ala Gly Ala Tyr
            20

(2) INFORMATION FOR SEQ ID NO:10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

GTATTAGCAG GAGATCTTCC TACTTC                                    26

(2) INFORMATION FOR SEQ ID NO:11:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

GTGTGTGTAG ATCTGGTGAA AGTCC                                     25

(2) INFORMATION FOR SEQ ID NO:12:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

ATTGTAGAGA TCTAAGTAAT TAGGTGCCG                                 29

(2) INFORMATION FOR SEQ ID NO:13:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

GCCAATTGCT CAGATCTTGT TTCTTATG                                  28

(2) INFORMATION FOR SEQ ID NO:14:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

GGAATTCGGA TCCTCGAGAG ATCTCGCCG                                      29

(2) INFORMATION FOR SEQ ID NO:15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

CCACTTTGAG ATCTCTACCG TCCTCCAGCC                                     30

(2) INFORMATION FOR SEQ ID NO:16:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

CCCTGAGATC TTCAGCTGCT AAGAC                                          25

(2) INFORMATION FOR SEQ ID NO:17:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

GGCTGAGATC TGGCAGACCT TGCAAAGTGG                                     30

(2) INFORMATION FOR SEQ ID NO:18:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

GTGATGAAGA TCTTACAGTT TAATTGCTCT CC                                  32

(2) INFORMATION FOR SEQ ID NO:19:

(i) SEQUENCE CHARACTERISTICS:
        (A) LENGTH: 26 base pairs
        (B) TYPE: nucleic acid
        (C) STRANDEDNESS: single (D) TOPOLOGY: linear (ii) MOLECULE TYPE: cDNA (xi) SEQUENCE DESCRIPTION: SEQ ID NO:19:

TTCTCCAGAT CTTGGTAAGG ACCATG                                              26

(2) INFORMATION FOR SEQ ID NO:20:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:20:

CACCTTCTGT AGATCTTTCA TCATCAGAAC                                          30

(2) INFORMATION FOR SEQ ID NO:21:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:21:

CATCGGCAGA TCTCTGAAGA AGTG                                                24

(2) INFORMATION FOR SEQ ID NO:22:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:22:

CCATGGCCAA TTTTAGATCT CGATGAAAC                                           29

(2) INFORMATION FOR SEQ ID NO:23:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:23:

GGACCATGAG ATCTAATCCA TAAAATTGGG                                          30

(2) INFORMATION FOR SEQ ID NO:24:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:24:

AAATGGGAGA TCTAATAAGG ATGTGGAGAG C                                31

(2) INFORMATION FOR SEQ ID NO:25:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

GGAGAGCAAT TAAAGACTTA AATGTTCATC AC                               32

(2) INFORMATION FOR SEQ ID NO:26:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

TTTTCATAGA TCTATACAAG CAGCTTT                                     27

(2) INFORMATION FOR SEQ ID NO:27:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

CAACCAGATC TAATGTGGAG AGCAATTAAA CTGTCG                           36

(2) INFORMATION FOR SEQ ID NO:28:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

CCAATAAGAG ATCTAAGAGC AATTAAACTG TCG                              33

(2) INFORMATION FOR SEQ ID NO:29:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

GGATGTGAGA TCTAATTAAA CTGTCGAATG TTCATCAC                         38

(2) INFORMATION FOR SEQ ID NO:30:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

```
GGAGAGCAGA TCTACTGTCG AATGTTCATC AC                             32
```

(2) INFORMATION FOR SEQ ID NO:31:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

```
AAGGATAGAT CTAGCAATTA AACTGTCGAA TGTTCATCAC                     40
```

(2) INFORMATION FOR SEQ ID NO:32:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:32:

```
TACAACTAGT ACCATGGTCG ATGGTCGACA GATCTCTCGA AAGCTTAGC TAGC       54
```

(2) INFORMATION FOR SEQ ID NO:33:

(i) SEQUENCE CHARACTERISTICS:
        (A) LENGTH: 981 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

```
CAGAGTATCG ATGAAATCTA CAAATATGAC AAAAAACAAC AACAAGAAAT CCTGGCGGCG    60
AAACCCTGGA CTAAGGATCA CCACTACTTT AAATACTGCA AAATCTCAGC ATTGGCTCTA   120
CTGAAAATGG TGATGCATGC CAGGTCAGGA GGCAACTTGG AAGTGATGGG TTTGATGCTC   180
GGGAAAGTCG ACGGCGAGAC CATGATCATC ATGGACAGTT TCGCTTTGAC TGTAGAGGGC   240
ACAGAAACTC GAGTAAATGC TCAAGCTGCT GCGTATGAGT ATATGGCTGC ATACATAGAA   300
AATGCCAAAC AGGTTGGCCG CCTTGAGAAT GCAATCGGTT GGTATCATAG CCACCCTGGT   360
TATGGCTGCT GGCTCTCCGG GATTGATGTT AGTACACAGA TGCTGAACCA GCAGTTTCAA   420
GAACCATTTG TAGCAGTGGT GATTGATCCA ACCAGAACAA TCTCTGCAGG AAAAGTGAAT   480
CTTGGCGCCT TTAGGACATA TCCAAAGGGC TACAAACCTC CTGATGAAGG ACCTTCTGAG   540
TACCAGACTA TCCCACCTTA ATAAAATAGA AGATTTGGGC GTGCACTGAA ACAATATTAT   600
GCCTTAGAAG TCTCATATTT CAAATCATCT TGGATCGTAA ACTACTTGAG CTTTGGTGGA   660
```

```
ATAAATACTG GGTGAATACC CTGAGTCCTC TAGCTTGCTT ACTAATGCAG ACTACACCAC     720

AGGCCAGGTG TTGATTTGTC TGAGAAGTTA GAGCAGTCGG AAGCCCAACT GGGACGTGGC     780

AGTTTCATGT TGGGCTTAGA AACACATGAC CGCAAGTCGG AAGACAAACT TGCCAAAGCT     840

ACTAGAGACA GCTGTAAAAC CACCATAGAA GCCACCATGG ACTGATGTCT CAGGTTATTA     900

AGGATAAACT GTTTAATCAG ATTAACGTTG TTAGTTACCA CCACGTACTT CTCAAAGTGG     960

TGTGTGGAAG GAAAAGAGCT C                                              981

(2) INFORMATION FOR SEQ ID NO:34:

(i) SEQUENCE CHARACTERISTICS:
        (A) LENGTH: 919 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

AAACCCTGGA CTAAGGATCA CCACTACTTT AAATACTGCA AAATCTCAGC ATTGGCTCTA      60

CTGAAAATGG TGATGCATGC CAGGTCAGGA GGCAACTTGG AAGTGATGGG TTTGATGCTC     120

GGGAAAGTCG ACGGGGAGAC CATGATCATC ATGGACAGTT TCGCTTTGCT GTAGAGGGCA     180

CAGAAACTCG AGTAAATGCT CAAGCTGCTG CGTATGAGTA TATGGCTGCA TACATAGAAA     240

ATGCCAAACA GGTTGGCCGC CTTGAGAATG CAATCGGTTG GTATCATAGC CACCCTGGTT     300

ATGGCTGCTG GCTCTCCGGG ATTGATGTTA GTACACAGAT GCTGAACCAG CAGTTTCAAG     360

AACCATTTGT AGCAGTGGTG ATTGATCCAA CCAGAACAAT CTCTGCAGGA AAAGTGAATC     420

TTGGCGCCTT TAGGACATAT CCAAAGGGCT ACAAACCTCC GATGAAGGAC CTTCTGAGTA     480

CCAGACTATC CCACCTTAAT AAAATAGAAG ATTTGGGCGT GCACTGAAAC AATATTATGC     540

CTTAGAAGTC TCATATTTCA AATCATCTTG GATCGTAAAC TACTTGAGCT TTGGTGGAAT     600

AAATACTGGG TGAATACCCT GAGTCCTCTA GCTTGCTTAC TAATGCAGAC TACACCACAG     660

GCCAGGTGTT GATTTGTCTG AGAAGTTAGA GCAGTCGGAA GCCCAACTGG ACGTGGCAG     720

TTTCATGTTG GCTTAGAAA CACATGACCG CAAGTCGGAA GACAAACTTG CCAAAGCTAC     780

TAGAGACAGC TGTAAAACCA CCATAGAAGC CACCATGGAC TGATGTCTCA GGTTATTAAG     840

GATAAACTGT TTAATCAGAT TAACGTTGTT AGTTACCACC ACGTACTTCT CAAAGTGGTG     900

TGTGGAAGGA AAAGAGCTC                                                 919

(2) INFORMATION FOR SEQ ID NO:35:

(i) SEQUENCE CHARACTERISTICS:
        (A) LENGTH: 541 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

GACCACCGAG ATGCCAATTC CAGTGTCATG AGATTTCTGC GAGACCTCAT CCACACAGGA      60

GTAGCCAATG ATTTATCTGT TTTCTTACAG CATGAAGAAG ATTTTGTTGC GGAAGGAACT     120

AATTGGACAG GTGATGAGCC AGCTTGGGCA GCAACTTGTC AGCCAGCTGC TCCACACATG     180

CTGCTTTTGG TTCCCCCCTA CACCCTACCC GACGTGGTTG AAGTGCTCTG GGAGATCATG     240
```

```
CAGGTTGACA GACCGACTTT CTGTCGGTGG CTAGAGAATT CCTTGAAAGG TTTGCCAAAA          300

GAGACCACAG TGGGAGCTGT CACAGTGACA CATAAACAAC TTACAGATTT CCACAAGCAA          360

GTCACTAGTG CCGAGGAATG TAAGCAAGTT TGCTGGGCCT TGAGAGACTT CACCAGGTTG          420

TTTCGATAGC TCAAGCTCAC ACTCCTGCAC TGTGCCTGTC ATCCAGGAAT GTCTTTTTTT          480

ATTAGAAGAC AGGAAGAAAA CAACCCAGAC TGTGTCCCAC AATCAGAAAC CTCTGTTGTG          540

G                                                                          541

(2) INFORMATION FOR SEQ ID NO:36:

(i) SEQUENCE CHARACTERISTICS:
            (A) LENGTH: 519 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:36:

CGAGATGCCA ATTCCAGTGT CATGAGATTT CTGCGAGACC TCATCCACAC AGGAGTAGCC           60

AATGATCATG AAGAAGATTT TGAATTGCGG AAGGAACTAA TTGGACAGGT GATGAGCCAG          120

CTTGGCCAGC AACTTGTCAG CCAGCTGCTC CACACATGCT GCTTTTGTCT TCCCCCTACA          180

CCCTACCCGA CGTGGTTGAA GTGCTCTGGG AGATCATGCA GGTTGACAGA CCGACTTTCT          240

GTCGGTGGCT AGAGAATTCC TTGAAAGGTT TGCCAAAAGA GACCACAGTG GGAGCTGTCA          300

CAGTGACACA TAAACAACTT ACAGATTTCC ACAAGCAAGT CACTAGTGCC GAGGAATGTA          360

AGCAAGTTTG CTGGGCCTTG AGAGACTTCA CCAGGTTGTT TCGATAGCTC AAGCTCACAC          420

TCCTGCACTG TGCCTGTCAT CCAGGAATGT CTTTTTTTAT TAGAAGACAG GAAGAAAACA          480

ACCCAGACTG TGTCCCACAA TCAGAAACCT CTGTTGTGG                                 519

(2) INFORMATION FOR SEQ ID NO:37:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:37:

Phe Lys Arg Arg Lys Lys Ala Ala Lys Ala Leu Ala Pro Lys
1               5                   10

(2) INFORMATION FOR SEQ ID NO:38:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:38:

Phe Ala Ala Arg Lys Lys Ala Ala Lys Ala Leu Ala Pro Lys
1               5                   10

(2) INFORMATION FOR SEQ ID NO:39:

(i) SEQUENCE CHARACTERISTICS:
```

(A) LENGTH: 14 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:39:

Phe Lys Arg Ala Ala Ala Ala Ala Lys Ala Leu Ala Pro Lys
1               5                  10

(2) INFORMATION FOR SEQ ID NO:40:

(i) SEQUENCE CHARACTERISTICS:
          (A) LENGTH: 14 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:40:

Phe Ala Ala Ala Ala Ala Ala Ala Lys Ala Leu Ala Pro Lys
1               5                  10

(2) INFORMATION FOR SEQ ID NO:41:

(i) SEQUENCE CHARACTERISTICS:
          (A) LENGTH: 14 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:41:

Phe Lys Arg Arg Lys Lys Ala Ala Ala Ala Leu Ala Pro Ala
1               5                  10

(2) INFORMATION FOR SEQ ID NO:42:

(i) SEQUENCE CHARACTERISTICS:
          (A) LENGTH: 14 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:42:

Phe Ala Ala Ala Ala Ala Ala Ala Ala Ala Leu Ala Pro Ala
1               5                  10

(2) INFORMATION FOR SEQ ID NO:43:

(i) SEQUENCE CHARACTERISTICS:
          (A) LENGTH: 29 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:43:

TACAGAATTC TTATTCACAT CCGGCCCTG                                    29

(2) INFORMATION FOR SEQ ID NO:44:

(i) SEQUENCE CHARACTERISTICS:

(A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:44:

TACATCTAGA CTCCATCCAG AAAAACAGGT ATGG                                34

(2) INFORMATION FOR SEQ ID NO:45:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:45:

TCTAGAGTCG ACCTGCAGGC ATGCAAGCTT                                     30

(2) INFORMATION FOR SEQ ID NO:46:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:46:

TCTAGACCAT GGTCGACCTG CAGGCATGCA GATCTCTCGA GAAGCTT                  47

(2) INFORMATION FOR SEQ ID NO:47:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:47:

CTAGACCATG GTCGACCTGC AGGCATGCAG ATCTCTCGAG A                        41

(2) INFORMATION FOR SEQ ID NO:48:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:48:

AGCTTCTCGA GAGATCTGCA TGCCTGCAGG TCGACCATGG T                        41

(2) INFORMATION FOR SEQ ID NO:49:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:49:

TACATCTAGA ATTATGAAAC TGAAGGTAAC AGTCAACGGC                                    40

(2) INFORMATION FOR SEQ ID NO:50:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:50:

TACAAGATCT GCATGCCATG GTGCGACCTT CGATGAGCTC G                                  41

(2) INFORMATION FOR SEQ ID NO:51:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:51:

TACAACCATG GCAATAAATG CTGAGGC                                                  27

(2) INFORMATION FOR SEQ ID NO:52:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:52:

CACAGGAAAC AGCTATGACC                                                          20

(2) INFORMATION FOR SEQ ID NO:53:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:53:

TACAACCATG GCTGAAATTT TGGATATAC                                                29

(2) INFORMATION FOR SEQ ID NO:54:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:54:

```
TACAACCATG GCAAGCCCAC TTGAAACTTC                                      30

(2) INFORMATION FOR SEQ ID NO:55:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:55:

GCGACTCTCT ACTGTTTCTC                                                 20

(2) INFORMATION FOR SEQ ID NO:56:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:56:

TACAAGATCT GCATGCCTGC AGGTCGACAC TAGTGCGTAC CTTCGATGAG CTCGAGACTA     60

AGG                                                                  63

(2) INFORMATION FOR SEQ ID NO:57:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:57:

ACAACTAGTA TGTCCGAGCC CAAGGCGATT GATCCC                               36

(2) INFORMATION FOR SEQ ID NO:58:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:58:

ATGTAGATCT TCACTGAATA TTGCTGCTAT TACTGCCGTT GCT                       43

(2) INFORMATION FOR SEQ ID NO:59:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:59:

GCTTTATTAT TGTAAGCAGC AGCGTAATTA GGTGCCG                              37
```

(2) INFORMATION FOR SEQ ID NO:60:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:60:

GTACAGCAGC TTTAGCAGCA GCGACATCTA AGTAATTAGG                40

(2) INFORMATION FOR SEQ ID NO:61:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:61:

CATACTTTAG TACAGCAGCA GCATTATTGT AGACATCTAA G               41

(2) INFORMATION FOR SEQ ID NO:62:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:62:

CACATTATTT TCATAAGCAG CAGCAGCAGC TTTATTATTG TAGAC           45

(2) INFORMATION FOR SEQ ID NO:63:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:63:

CGAATGTTCA TCACATTAGC AGCAGCCTTT AGTACAGCAG C               41

(2) INFORMATION FOR SEQ ID NO:64:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:64:

GCAATTAAAC TGTCGAATGT TAGCAGCAGC ATTTTCATAC TTTAG           45

(2) INFORMATION FOR SEQ ID NO:65:

(i) SEQUENCE CHARACTERISTICS:
    (A) LENGTH: 45 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:65:

GGAGAGCAAT TAAACTGAGC AGCAGCCATC ACATTATTTT CATAC        45

(2) INFORMATION FOR SEQ ID NO:66:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:66:

GGATGTGGAG AGCAAGCAGC AGCTCGAATG TTCATC        36

(2) INFORMATION FOR SEQ ID NO:67:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:67:

TATGGGTACC GCTGCTGCTG CTGCCATGGA GGCCCCGGG        39

(2) INFORMATION FOR SEQ ID NO:68:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:68:

GATCCCCGGG GCCTCCATGG CAGCAGCAGC AGCGGTACCC A        41

(2) INFORMATION FOR SEQ ID NO:69:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:69:

AGGACGCAGG GTACCGCATG TACAGGAAAA GCC        33

(2) INFORMATION FOR SEQ ID NO:70:

(i) SEQUENCE CHARACTERISTICS:
        (A) LENGTH: 30 base pairs
        (B) TYPE: nucleic acid
        (C) STRANDEDNESS: single -continued (D) TOPOLOGY: linear (ii) MOLECULE TYPE: cDNA (xi) SEQUENCE DESCRIPTION: SEQ ID NO:70:

CTCCGCTGGG GAGCATGCCA GTCGGGGTCA                                       30

(2) INFORMATION FOR SEQ ID NO:71:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:71:

GAACTGCGCG GCGGCCATCA CCTTGTTCTC GTA                                   33

(2) INFORMATION FOR SEQ ID NO:72:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:72:

CGTGATGGCC GCCGCGCAGT TCAACTGCTC C                                     31

(2) INFORMATION FOR SEQ ID NO:73:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:73:

CCGCCGCCAT GGGAGTGCAG TGG                                              23

(2) INFORMATION FOR SEQ ID NO:74:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:74:

GGAGGCCACA TTCCAGTTTT AGAAGCTCC                                        29